(12) United States Patent
Takahasi

(10) Patent No.: US 7,901,594 A0
(45) Date of Patent: Mar. 8, 2011

(54) POLYACENE DERIVATIVES AND PRODUCTION THEREOF

(75) Inventor: Tamotsu Takahasi, Sapporo (JP)

(73) Assignee: Japan Science and Technology Corporation, Saitama (JP)

( * ) Notice: Subject to any disclaimer, the term of this patent is extended or adjusted under 35 U.S.C. 154(b) by 471 days.

(21) Appl. No.: 10/220,013

(22) PCT Filed: Feb. 28, 2001

(86) PCT No.: PCT/JP01/01479
§ 371 (c)(1),
(2), (4) Date: Aug. 26, 2002

(87) PCT Pub. No.: WO01/64611
PCT Pub. Date: Sep. 7, 2001

(65) Prior Publication Data
US 2003/0116755 A1    Jun. 26, 2003

(30) Foreign Application Priority Data

Feb. 29, 2000    (JP) ................................. 2000-054666
Aug. 25, 2000   (WO) ....................... PCT/JP00/05768

(51) Int. Cl.
C09K 3/00      (2006.01)
C07C 50/12    (2006.01)
H01L 51/54    (2006.01)
H01B 1/12      (2006.01)

(52) U.S. Cl. .............. 252/500; 252/301.35; 252/301.36; 252/700; 257/40; 313/504; 313/505; 428/690; 428/917; 438/99; 568/58; 568/632; 568/633; 568/634; 570/183; 564/387; 564/426; 585/320; 585/322; 585/324; 585/26; 552/208; 552/268; 552/271

(58) Field of Classification Search .................. 252/500, 252/511, 301.16, 301.35; 585/400, 632, 585/26, 21; 313/504, 506; 257/40; 552/208, 552/267; 570/101
See application file for complete search history.

(56) References Cited

U.S. PATENT DOCUMENTS 3,326,852 A * 6/1967 Thomas ........................ 528/169
(Continued)

FOREIGN PATENT DOCUMENTS

JP    63-66130 A    3/1988
(Continued)

OTHER PUBLICATIONS

Hart et al, "Tetrahalobenzenes as Di-Aryne Equivalents in Polycyclic Arene synthesis," Tetrahedron, 1987, 43(22), pp. 5203-5224.*
(Continued)

Primary Examiner — Stanley Silverman
Assistant Examiner — Kallambella Vijayakumar
(74) Attorney, Agent, or Firm — Foley & Lardner LLP

(57) ABSTRACT

The present invention relates to polyacene derivatives represented by general formula (I) below:

(wherein $R^1$ to $R^{10}$, etc. each represents hydrogen atom, hydrocarbon group, or an alkoxy group; $A^1$ and $A^2$ are hydrogen atom, a halogen atom, a hydrocarbon group, an alkoxy group, cyano group, etc.; n is an integer of not less than 1; $R^6$ and $R^7$ may be linked to each other to form a ring); and a process for preparing the polyacene derivatives from polyhydro compounds as well as electrically conductive materials comprising the polyacene derivatives. According to the process for preparing the polyacene derivatives of the present invention, optional substituents can be introduced into any carbon atoms of the polyacene, and the number of aromatic rings can be increased.

40 Claims, 6 Drawing Sheets

U.S. PATENT DOCUMENTS

| | | | |
|---|---|---|---|
| 3,557,233 | A | 1/1971 | Zweig et al. |
| 3,729,426 | A | 4/1973 | Zweig et al. |
| 3,912,931 | A * | 10/1975 | Gravisse et al. ........... 250/458.1 |
| 4,762,943 | A | 8/1988 | Ramachandran et al. |
| 5,077,142 | A | 12/1991 | Sakon et al. |
| 5,206,390 | A * | 4/1993 | Baumann et al. ............. 549/214 |
| 6,121,727 | A * | 9/2000 | Kanai et al. .................... 313/504 |
| 6,165,383 | A * | 12/2000 | Chou ...................... 252/301.16 |
| 6,203,933 | B1 * | 3/2001 | Nakaya et al. ................ 428/690 |
| 6,285,039 | B1 | 9/2001 | Kobori et al. |
| 6,344,284 | B1 * | 2/2002 | Chou ........................... 428/690 |
| 6,465,116 | B1 * | 10/2002 | Ishikawa et al. ............. 428/690 |
| 6,489,046 | B1 * | 12/2002 | Ikeda et al. ................... 428/690 |
| H2084 | H * | 10/2003 | Picciolo et al. ............... 428/690 |

FOREIGN PATENT DOCUMENTS

| | | | |
|---|---|---|---|
| JP | 04-335087 A | | 11/1992 |
| JP | 06-136360 A | | 5/1994 |
| JP | 11-354277 | * | 12/1999 |
| JP | 11-354277 A | | 12/1999 |
| JP | 2000-021571 A | | 1/2000 |
| JP | 2000-026339 | * | 1/2000 |
| JP | 2000-026339 A | | 1/2000 |
| JP | 2000-299188 A | | 10/2000 |
| WO | WO 98/08360 A1 | | 2/1998 |
| WO | WO 00/03565 A1 | | 1/2000 |
| WO | 00/56933 A1 | | 9/2000 |
| WO | WO 00/56933 A1 | | 9/2000 |

OTHER PUBLICATIONS

Lepage, "Conversion of naphthalenes to anthracene and naphthacenes," Chem. Abst, 6332 b-f.*

Takashi et al, "Straightforward Method for Synthesis of Highly Alkyl-Substituted Naphthacene and Pentacene Derivatives by Homologation," J. Am. Chem. Soc., 2000, 122, pp. 12876-12877.*

Herndon, "Resonance Theory. VIII. Reactivities of Benzenoid Hydrocarbons," J. Org. Chem, 1975, 40(24), pp. 3583-3586.*

"Conversion of Naphthalenes to Anthracenes and to Naphthacenes", <1, 4, 5, 7, 10, 12-Hexaphenylnaphthacene Compounds, Chemical Abstracts, vol. 59, 6332b-f.

Harold Hart et al., "Tetrahalobenzenes as Di-Aryne Equivalents in Polycyclic Arene Synthesis," Tetrahedron, vol. 43, No. 22, pp. 5203 to 5224, (1987).

Shyi-Long Lee et al., "Theoretical Studies of the Molecular Second-Order Hyperpolarizabilities of Polycyclic Aromatics," International Journal of Quantum Chemistry, Quantum Chemistry Symposium 29, pp. 509 to 522, (1985).

Takahashi et al., "Coupling Reaction of Zirconacyclopentadienes with Dihalonaphthalenes and Dihalopyridines: A New Procedure for the Preparation of Substituted Anthracenes, Quinolines, and Isoquinolines," Journal of the American Chemical Society, vol. 124, No. 4, pp. 576-582, (2002).

Takahashi et al., "Straightforward Method for Synthesis of Highly Alkyl-Substituted Naphthacene and Pentacene Derivatives by Homologation," Journal of the American Chemical Society, vol. 122, No. 51, pp. 12876-12877, (2000).

Luo et al., "Linear Acene Derivatives, New Routes to Pentacene and Naphthacene and the First Synthesis of a Triptycene with Two Anthracene Moieties," J. Org. Chem., Oct. 30, 1987, 52(22), 4833-4836.

Reetz et al., "Deprotonation-hydride elimination as method for dehydrogenation," Angew. Chem., 1978, 90(4), 285-286, with English translation.

Thummel et al., "Diels-Alder Approach to Naphthocyclobutenes and Anthrocyclobutenes," J. Org. chem.., 1978, 43(12), 2473-2477.

Brzezinski et al., "An intramolecular chain of four hydrogen bonds in the 1,11,12,13,14- pentahydroxymethylpentacene tetrabutylammonium salt," Chemical Physics Letters, Mar. 22, 1991, 178(2,3):138-140.

Cosmo et al., "Dehydrogenation of 4,5-disubstituted 9,10-dihydrophenanthrenes," Abstract of Australian Journal of Chemistry, 1987, 40(12):2137-2142 (four pages).

Herndon, William O., "Resonance Theory. VIII. Reactivities of Benzenoid Hydrocarbons," J. Org. Chem., 1975, 40(24):3583-3586.

Herr, M.L., "Quantum Chemistry Studies Equilibria in Some Acene Derivatives," Tetrahedron, 1972, 28:5139-5147.

Sangaiah et al., "Synthesis of New cyclopenta-Fused PAH Isomers of Cata-Annelated Benzenoid Systems," J. Org. Chem., 1987, 52:3205-3211.

Sen, Li, "The Quantitative Sequence of Conjugative Effect of the Even Benzenoid Hydrocarbons," Tongji Daxue Xuebao, Ziran Kexueban, 1982, (4), 11-17, with English abstract.

Yamamoto et al., "Metacyclophanes and related compounds. Part 16. Preparation of 8-fluoro-tert- butyl[2.2]metacyclophanes and their treatment with aluminum chloride-nitromethane in benzene," Abstract of the Journal of the Chemical Society, Perkin Transactions 1: Organic and Bio-Organic Chemistry (1972-1999) (1987), (1):1-7, four pages.

Office Action dated Mar. 24, 2009, in corresponding European Application 01 908 120.7, 5 pages.

Maulding et al., Electronic Absorption and Fluorescence of Phenylethynyl-Substitute Acenes, J. Org. Chem., 1969, 34(6):1734-1736.

Database CA Chemical Abstracts Service, retrieved from STN accession No. 44:20038, 3 pages (abstract of CLAR, E., Aromatic hydrocarbons. LIV. Anellation principle and resonance in aromatic hydrocarbons, Chemische Berichte, 1949, 82:495-514, accessed Mar. 17, 2009).

Baudouy et al., "Synthese de bis-allenes conjugues," Tetrahedron Letters, 1974, 17:1593-1596.

Berlin et al., "Synthesis of 1,2,3,4-Tetrahydrocarbazoles with Large Groups - Aromatization to Carbazoles," Proc. of the Okla. Accad. Of Sci. for 1966, Physical Sciences, 215-220.

Berris et al., "A New Approach to the Construction of Biphenylenes by the Cobalt-Catalyzed Cocyclization of o-Diethynylbenzenes with Alkynes. Application to an Iterative Approach to [3]Phenylene, the First Member of a Novel Class of enzocyclobutadienoid Hydrocarbons," J. Am. Chem. Soc., 1985, 107:5670-5687.

Hiemstra et al,. "Silicon Directed N-Acyliminium Ion Cyclizations. Highly Selective Syntheses of (±)- Isoretronecanol and (±)-Epilupinine," J. Org. Chem., 1985, 50:4014-4020.

March, Jerry, Ed., Advanced Organic Chemistry, Reactions, Mechanisms, and Structure, $3^{rd}$ Edition, 1985, 382-384, 429, 694-497, 775, 1052-1052.

Observations on European Patent Application No. 01908120, Feb. 11, 2009, 15 pages.

Takahashi et al., "Carbon-Carbon Bond Formation Reaction of Zirconacyclopentadienes with Alkynes in the Presence of Ni(II)-complexes," J. Am. Chem. Soc., 1999, 121:11093-11100.

Trost et al., "Carbonyl Reductions," Org. Syn., 1991, 8:105-108.

World Health Organization International Agency for Research on Cancer, IARC Monographs on the Evaluation of Carcinogenic Risks to Humans, Some Antiviral and Antineoplastic Drugs, and Other Pharmaceutical Agents, "Mitoxantrone," 2000, 76:289-315.

Zhang et al., "Versatile Synthesis of Dihydroquinolines and Quinoline Quinones Using Cyclobutenediones. Construction of the Pyridoaridine Ring System," J. Org. Chem., 1997, 62:4330-4338.

"Conversion of Naphthalenes to Anthracenes and to Naphthacenes", 1, 4, 5, 7, 10, 12- Hexaphenylnaphthacene Compounds, Chemical Abstracts, vol. 59, 6332b-f. (1963) .

Harold Hart et al., "Tetrahalobenzenes as Di-Aryne Equivalents in Polycyclic Arene Synthesis," Tetrahedron, vol. 43, No. 22, pp. 5203 to 5224, (1987).

Shyi-Long Lee et al., "Theoretical Studies of the Molecular Second-Order Hyperpolarizabilities of Polycyclic Aromatics," International Journal of Quantum Chemistry, Quantum Chemistry Symposium 29, pp. 509 to 522, (1985).

Takahashi et al., "Coupling Reaction of Zirconacyclopentadienes with Dihalonaphthalenes and Dihalopyridines: A New Procedure for the Preparation of Substituted Anthracenes, Quinolines, and Isoquinolines," Journal of the American Chemical Society, vol. 124, No. 4, pp. 576-582, (2002).

Takahashi et al., "Straightforward Method for Synthesis of Highly Alkyl-Substituted Naphthacene and Pentacene Derivatives by Homologation," Journal of the American Chemical Society, vol. 122, No. 51, pp. 12876-12877, (2000).

* cited by examiner

POLYACENE DERIVATIVES AND PRODUCTION THEREOF

FIELD OF THE INVENTION

The present invention relates to polyacene derivatives and a process of producing the same.

BACKGROUND ART

It is known that conductive materials are obtained by doping electron donating molecules or electron accepting molecules into conjugated polymers as organic conductive materials, including polyacetylene, polypyrrole, polyallylenevinylene, polythienylenevinylene, etc. It is also known that electron transfer complexes formed by the combination of electron donating molecules such as tetrathiafulvalene, bisethylenedithiotetrathiafulvalene, etc. and electron accepting molecules such as tetracyanoquinodimethane, tetracyanoethylene, etc. exhibit a conductive property. Some of these organic conductive materials show high conductivity but can form a thin film only with difficulty. Furthermore, these conductive materials involve a problem in terms of stability, since they are readily oxidized in the air.

Since condensed polycyclic aromatic compounds like polyacenes such as anthracene, naphthacene, pentacene, etc. are conjugated polymers, it is known that these compounds exhibit a conductive property by doping electron donating molecules or electron accepting molecules into these compounds. It has thus been expected to use these compounds as electronic industry materials. Also, as the number of condensed benzene rings in polyacenes increases, the band gap between HOMO and LUMO decreases theoretically so that it is expected to increase the conductive property of polyacenes. Therefore, even if the concentration of dopants is low, it is likely to exhibit a sufficient conductive property.

Condensed polycyclic aromatic compounds such as polyacenes, however, have a very poor solubility and are hardly soluble, when no substituent is introduced therein. For this reason, there is a limit to synthesis methods using such condensed polycyclic aromatic compounds, and it was extremely difficult to process these compounds. It has thus been desired to introduce substituents on the side chains of condensed polycyclic aromatic compounds to improve the solubility strikingly, and to produce polyacenes suitable for easy synthesis and processing. In particular, any process for synthesis of sequentially increasing the number of condensed benzene rings while introducing substituents therein was unknown.

Heretofore, a means for introducing optional substituents at optional positions of polyacenes such as anthracene, naphthacene, pentacene, etc. has been limited to the Diels-Alder reaction.

For example, a process of producing decamethylanthracene is described in Harold Hart, et al., "Decamethylanthracene and its 10-'Dewar' Isomer," Tetrahedron Letter, No. 36, pp. 3143-3146. According to this process, the Diels-Alder reaction was applied to introduce methyl group into anthracene. Likewise in Tetrahedron, Vol. 43, No. 22, pp. 5403-5214, methyl group or the like was introduced into polyacenes by using the Diels-Alder reaction.

In the Diels-Alder reaction, there was a limit to substituents that can be introduced onto side chains. With respect to carbon atoms that can be substituted onto side chains, their latitude was limited as well. Further in the Diels-Alder reaction, it is impossible to increase the number of condensed benzene rings sequentially. In the Diels-Alder reaction, it is necessary to design a scheme of synthesis, respectively, considering the individual structures of target compounds.

JPA Nos. H4-335087, H6-167807, H6-330032 and H10-36832 disclose substituted naphthacenes, and JPA No. H11-354277 discloses substituted pentacenes. However, these compounds were all synthesized based on classic methods of synthesis, and substituents that could be introduced or positions at which substituents could be introduced were limited. And any process of synthesis for sequentially increasing the number of condensed benzene rings while introducing substituents was not disclosed, either.

DISCLOSURE OF THE INVENTION

In one aspect of the present invention, it is an object to introduce optional substituents into polyacenes at optional carbon atoms thereby to improve the solubility. By introducing substituents on the side chains of polyacenes, not only the solubility can be improved but further synthesis can be readily performed by introducing desired substituents so that the side chains of the polyacenes can be modified in various ways. Thus, the number of condensed aromatic rings can be increased sequentially while introducing substituents on the side chains of polyacenes.

It is described in K. P. C. Vollhardt et al., Journal of American Chemical Society, 1985, 107, 5670 that 1,2-bis(trimethylsilyl)acetylene is reacted with 1,2-diethynylbenzene in the presence of a catalyst such as cyclopentadienylbiscarbonylcobalt, etc. to simultaneously form the two rings of 4-membered ring condensed to benzene and benzene ring condensed to this 4-membered ring. That is, 3 rings are formed, taking into account the benzene ring originally present. Since two trimethylsilyl groups are present on the ortho-position on the 3 ring-product, it is described that iodine chloride (ICl) is reacted with the product followed by reacting with trimethylsilylacetylene under basic conditions in the presence of palladium catalyst. There is described such a scheme that the reaction is similarly repeated as such to increase the number of condensed rings two at a time.

In one aspect of the present invention, there is provided a polyacene derivative represented by general formula (I) below:

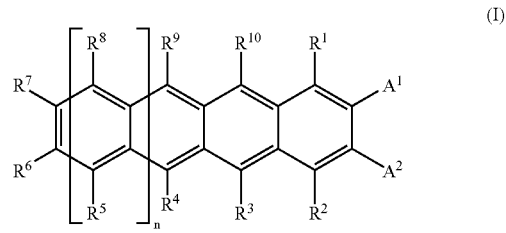

(wherein:

each of $R^1$, $R^2$, $R^3$, $R^4$, $R^5$, $R^6$, $R^7$, $R^8$, $R^9$ and $R^{10}$, which may be the same or different, independently represents hydrogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; an amino group which may optionally be substituted; a hydroxy group; or a silyl group which may optionally be substituted; provided that $R^6$ and $R^7$ may be cross-bridged with each other to form a $C_4$-$C_{40}$ saturated or unsaturated ring, and the saturated or unsaturated ring may be intervened by oxygen atom, sulfur atom or a group shown by formula: —N($R^{11}$)— (wherein $R^{11}$ is hydrogen atom or a hydrocarbon group), or may optionally be substituted;

each of $A^1$ and $A^2$, which may be the same or different, independently represents hydrogen atom; a halogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; a $C_7$-$C_{40}$ alkylaryloxy group which may optionally be substituted; a $C_2$-$C_{40}$ alkoxycarbonyl group which may optionally be substituted; a $C_7$-$C_{40}$ aryloxycarbonyl group which may optionally be substituted; cyano group (—CN); carbamoyl group (—C(=O)$NH_2$); a haloformyl group (—C(=O)—X, wherein X represents a halogen atom); formyl group (—C(=O)—H); isocyano group; isocyanate group; thiocyanate group or thioisocyanate group; provided that $A^1$ and $A^2$ may be cross-bridged with each other to form a ring shown by formula: —C(=O)—B—C(=O)— (wherein B is oxygen atom or a group shown by formula —N($B^1$)— (wherein $B^1$ is hydrogen atom, a $C_1$-$C_{40}$ hydrocarbon group or a halogen atom));

n is an integer of not less than 1;

with proviso that, except for the case wherein $R^1$, $R^2$, $R^3$, $R^4$, $R^5$, $R^6$, $R^7$, $R^8$, $R^9$, $R^{10}$, $A^1$ and $A^2$ are all hydrogen atoms;

when n is 1, at least $R^1$, $R^2$, $R^4$ and $R^9$ are groups other than hydrogen atom, or at least $R^3$, $R^5$, $R^8$ and $R^{10}$ are groups other than hydrogen atom; and, the cases of (a), (b), (c) and (d) below are excluded:

(a) when $R^1$, $R^2$, $R^3$, $R^4$, $R^5$, $R^6$, $R^7$, $R^8$, $R^9$, $R^{10}$, $A^1$ and $A^2$ are all methyl groups;

(b) when $R^3$, $R^4$, $R^9$ and $R^{10}$ are all aryl groups that may optionally be substituted;

(c) when $R^1$, $R^2$, $R^4$ and $R^9$ are all alkoxy or aryloxy groups, and $R^3$, $R^5$, $R^6$, $R^7$, $R^8$, $R^{10}$, $A^1$ and $A^2$ are all hydrogen atoms;

(d) when $R^3$, $R^5$, $R^8$ and $R^{10}$ are all alkoxy or aryloxy groups, and $R^1$, $R^2$, $R^4$, $R^6$, $R^7$, $R^9$, $A^1$ and $A^2$ are all hydrogen atoms;

and, when n is 2, the cases of (a'), (b'), (c') and (d') below are excluded:

(a') a pentacene derivative represented by formula (Ia) below:

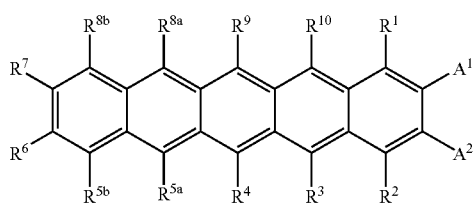

(Ia)

wherein $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are all methyl groups; or $R^1$, $R^2$, $R^3$, $R^4$, $R^{5a}$, $R^{5b}$, $R^{8a}$, $R^{8b}$, $R^9$ and $R^{10}$ are all hydrogen atoms and at least one of $R^6$, $R^7$, $A^1$ and $A^2$ is an aryl group; or at least one of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ is a diarylamine group;

(b') a pentacene derivative represented by formula (Ib) below:

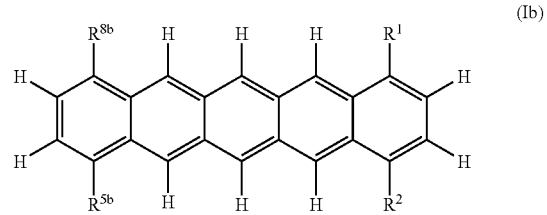

(Ib)

wherein $R^1$, $R^2$, $R^{5b}$ and $R^{8b}$ are all alkoxy or aryloxy groups;

(c') a pentacene derivative represented by formula (Ic) below:

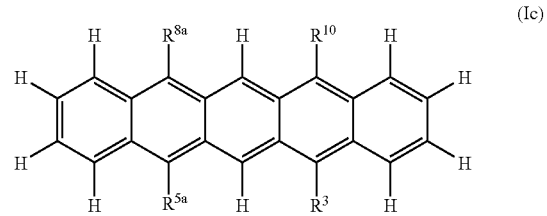

(Ic)

wherein at least 2 of $R^3$, $R^{5a}$, $R^{8a}$ and $R^{10}$ are aryl or arylalkynyl groups; or at least one of $R^3$, $R^{5a}$, $R^{8a}$ and $R^{10}$ is an arylalkenyl group; or $R^3$, $R^{5a}$, $R^{8a}$ and $R^{10}$ are all alkoxy or aryloxy groups;

(d') a pentacene derivative represented by formula (Id) below:

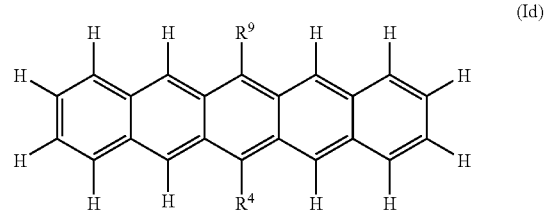

(Id)

wherein $R^4$ and $R^9$ are hydrogen atom, a hydrocarbon group, an alkoxy group, an aryloxy group, a halogen atom or hydroxy group.)

In a further aspect of the present invention, preferably at least 5 of $R^1$, $R^2$, $R^3$, $R^4$, $R^5$, $R^6$, $R^7$, $R^8$, $R^9$, $R^{10}$, $A^1$ and $A^2$ are groups other than hydrogen atom, and more preferably at least 6 of $R^1$, $R^2$, $R^3$, $R^4$, $R^5$, $R^6$, $R^7$, $R^8$, $R^9$, $R^{10}$, $A^1$ and $A^2$ are groups other than hydrogen atom.

The polyacene derivative described above is preferably a pentacene derivative represented by formula (Ia):

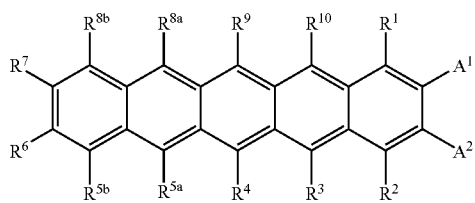

(wherein:
each of $R^1$, $R^2$, $R^3$, $R^4$, $R^{5a}$, $R^{5b}$, $R^6$, $R^7$, $R^{8a}$, $R^{8b}$, $R^9$ and $R^{10}$, which may be the same or different, independently represents hydrogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; an amino group which may optionally be substituted; a hydroxy group; or a silyl group which may optionally be substituted; provided that $R^6$ and $R^7$ may be cross-bridged with each other to form a $C_4$-$C_{40}$ saturated or unsaturated ring, and the saturated or unsaturated ring may be intervened by oxygen atom, sulfur atom or a group shown by formula: —N($R^{11}$)— (wherein $R^{11}$ is hydrogen atom or a hydrocarbon group), or may optionally be substituted;

each of $A^1$ and $A^2$, which may be the same or different, independently represents hydrogen atom; a halogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; a $C_7$-$C_{40}$ alkylaryloxy group which may optionally be substituted; a $C_2$-$C_{40}$ alkoxycarbonyl group which may optionally be substituted; a $C_7$-$C_{40}$ aryloxycarbonyl group which may optionally be substituted; cyano group (—CN); carbamoyl group (—C(=O)NH$_2$); a haloformyl group (—C(=O)—X, wherein X represents a halogen atom); formyl group (—C(=O)—H); isocyano group; isocyanate group; thiocyanate group or thioisocyanate group; provided that $A^1$ and $A^2$ may be cross-bridged with each other to form a ring shown by formula: —C(=O)—B—C(=O)— (wherein B is oxygen atom or a group shown by formula —N($B^1$)— (wherein $B^1$ is hydrogen atom, a $C_1$-$C_{40}$ hydrocarbon group or a halogen atom)), and at least 5 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom, more preferably at least 6 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom, further more preferably at least 7 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom, much more preferably at least 8 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom, further much more preferably at least 9 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom, and most preferably at least 10 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom.

In one aspect of the present invention, any one of the combinations of $R^1$ and $R^2$, $R^3$ and $R^{10}$, $R^4$ and $R^9$, $R^5$ and $R^8$, $R^6$ and $R^7$, and $A^1$ and $A^2$ are preferably the same substituents; in one aspect of the present invention wherein the polyacene derivative is the pentacene derivative represented by the formula (Ia) above, any one of the combinations of $R^1$ and $R^2$, $R^3$ and $R^{10}$, $R^4$ and $R^9$, $R^{5a}$ and $R^{8a}$, $R^{5b}$ and $R^{8b}$, $R^6$ and $R^7$, and $A^1$ and $A^2$ are preferably the same substituents.

In one aspect of the present invention, any one of $R^1$, $R^2$, $R^3$, $R^4$, $R^5$, $R^6$, $R^7$, $R^8$, $R^9$ and $R^{10}$ is preferably a $C_1$-$C_{40}$ hydrocarbon group which may optionally be substituted, a $C_1$-$C_{40}$ alkoxy group which may optionally be substituted, or a $C_6$-$C_{40}$ aryloxy group which may optionally be substituted; in one aspect of the present invention, when the polyacene derivative is the pentacene derivative represented by the formula (Ia) above, any one of $R^1$, $R^2$, $R^3$, $R^4$, $R^{5a}$, $R^{5b}$, $R^6$, $R^7$, $R^{8a}$, $R^{8b}$, $R^9$ and $R^{10}$ is preferably a $C_1$-$C_{40}$ hydrocarbon group which may optionally be substituted, a $C_1$-$C_{40}$ alkoxy group which may optionally be substituted, or a $C_6$-$C_{40}$ aryloxy group which may optionally be substituted.

In one aspect of the present invention, when n is 1, $A^1$ and $A^2$ may be an alkoxycarbonyl group, and $R^1$, $R^2$, $R^4$ and $R^9$ may be an alkyl or aryl group; or when n is 1, $A^1$, $A^2$, $R^1$, $R^2$, $R^4$ and $R^9$ may be an alkyl or aryl group; or further when n is 1, $A^1$ and $A^2$ may be a halogen atom and $R^3$, $R^5$, $R^6$, $R^7$, $R^8$ and $R^{10}$ may be an alkyl or aryl group.

In one aspect of the present invention, when the polyacene derivative is the pentacene derivative represented by the formula (Ia) above, $A^1$ and $A^2$ may be an alkoxycarbonyl group and $R^1$, $R^2$, $R^4$, $R^{5b}$, $R^6$, $R^7$, $R^{8b}$ and $R^9$ may be an alkyl or aryl group; or when the polyacene derivative is the pentacene derivative represented by the formula (Ia) above, $A^1$, $A^2$, $R^1$, $R^2$, $R^4$, $R^{5b}$, $R^6$, $R^7$, $R^{8b}$ and $R^9$ may be an alkyl or aryl group; or, when the polyacene derivative is the pentacene derivative represented by the formula (Ia) above, $A^1$ and $A^2$ may be a halogen group and $R^3$, $R^{5a}$, $R^{8a}$ and $R^{10}$ may be an alkyl or aryl group.

In another aspect of the present invention, there is provided a process of producing the polyacene derivative represented by formula (I) below:

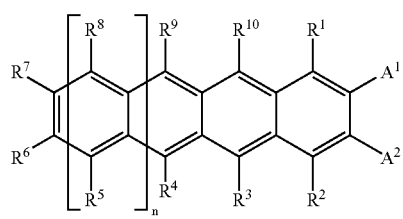

(wherein:
each of $R^1$, $R^2$, $R^3$, $R^4$, $R^5$, $R^6$, $R^7$, $R^8$, $R^9$ and $R^{10}$, which may be the same or different, independently represents hydrogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; an amino group which may optionally be substituted; a hydroxy group; or a silyl group which may optionally be substituted; provided that $R^6$ and $R^7$ may be cross-bridged with each other to form a $C_4$-$C_{40}$ saturated or unsaturated ring, and the saturated or unsaturated ring may be intervened by oxygen atom, sulfur atom or a group shown by formula: —N($R^{11}$)— (wherein $R^{11}$ is hydrogen atom or a hydrocarbon group), or may optionally be substituted;

each of $A^1$ and $A^2$, which may be the same or different, independently represents hydrogen atom; a halogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; a $C_7$-$C_{40}$ alkylaryloxy group which may optionally be substituted; a $C_2$-$C_{40}$ alkoxycarbonyl group which may optionally be substituted; a $C_7$-$C_{40}$ aryloxycarbonyl group which may optionally be substituted; cyano group (—CN); carbamoyl group (—C(=O)NH$_2$); a haloformyl group (—C(=O)—X, wherein X represents a halogen atom); formyl group (—C(=O)—H); isocyano group; isocyanate group; thiocyanate group or thioisocyanate group; provided that $A^1$ and $A^2$ may be cross-bridged with each other to form a ring shown by formula: —C(=O)—B—C(=O)— (wherein B is oxygen atom or a group shown by formula —N(B$^1$)— (wherein B$^1$ is hydrogen atom, a $C_1$-$C_{40}$ hydrocarbon group or a halogen atom)); and, n is an integer of not less than 1),
which comprises aromatizing hydrocarbon condensed rings represented by formula (II) below:

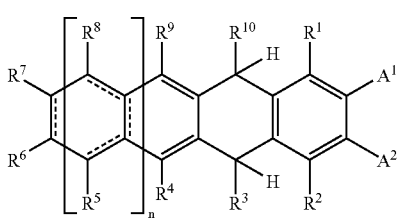

(II)

(wherein $R^1$, $R^2$, $R^3$, $R^4$, $R^5$, $R^6$, $R^7$, $R^8$, $R^9$, $R^{10}$, $A^1$, $A^2$ and n have the same significance as defined above;

the bond shown by formula below represents a single bond or a double bond;

≡ provided that when the bond is a single bond, hydrogen atom is further bound directly to the carbon atoms which are directly bound to $R^5$, $R^6$, $R^7$ and $R^8$);

in the presence of a dehydrogenation reagent.

In one embodiment of the present invention, the dehydrogenation reagent is a combination of a lithium dopant and a lithium-removing reagent. It is preferred to add first the lithium dopant to the hydrocarbon condensed rings and then add the lithium-removing reagent. Preferably, the lithium dopant is an alkyl lithium and the lithium-removing reagent is an alkyl halide.

In another embodiment of the present invention, the dehydrogenation reagent described above is preferably a compound represented by formula (III) given below:

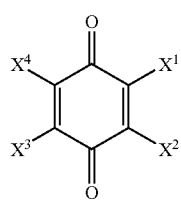

(III)

(wherein each of $X^1$, $X^2$, $X^3$ and $X^4$, which may be the same or different, independently represents a halogen atom or cyano group).

In another embodiment of the present invention, the dehydrogenation reagent described above preferably contains palladium.

It is also preferred that at least 5 of $R^1$, $R^2$, $R^3$, $R^4$, $R^5$, $R^6$, $R^7$, $R^8$, $R^9$, $R^{10}$, $A^1$ and $A^2$ are groups other than hydrogen atom, more preferably, at least 6 of $R^1$, $R^2$, $R^3$, $R^4$, $R^5$, $R^6$, $R^7$, $R^8$, $R^9$, $R^{10}$, $A^1$ and $A^2$ are groups other than hydrogen atom.

It is also preferred that the polyacene derivative described above is the pentacene derivative shown by formula (Ia) below:

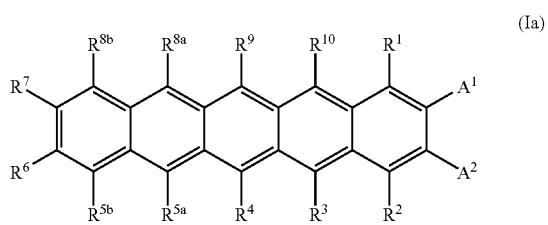

(Ia)

(wherein $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ have the same significance as defined above), and at least 5 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom. More preferably, at least 6 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom; further more preferably, at least 7 of $R^1$, $R^2$, $R^3$, $R^4$, $R^5$, $R^{5b}$, $R^6$, $R^7$, $R^{8a}$, $R^{8b}$, $R^{10}$, $A^1$ and $A^2$ are groups other than hydrogen atom; much more preferably, at least 8 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom; further much more preferably, at least 9 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom; and most preferably, at least 10 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom.

Or, any one of the combinations of $R^1$ and $R^2$, $R^3$ and $R^{10}$, $R^4$ and $R^9$, $R^5$ and $R^8$, $R^6$ and $R^7$, and $A^1$ and $A^2$ are preferably the same substituents; in another aspect of the present invention, when the polyacene derivative is the pentacene derivative represented by the formula (Ia) above, either the sets of $R^1$ and $R^2$, $R^3$ and $R^{10}$, $R^4$ and $R^9$, $R^{5a}$ and $R^{8a}$, $R^{5b}$ and $R^{8b}$, $R^6$ and $R^7$, or the set of $A^1$ and $A^2$ are preferably the same substituents.

Or, any one of $R^1$, $R^2$, $R^3$, $R^4$, $R^5$, $R^6$, $R^7$, $R^8$, $R^9$ and $R^{10}$ is preferably a $C_1$-$C_{40}$ hydrocarbon group which may optionally be substituted; a $C_1$-$C_{40}$ alkoxy group which may optionally be substituted; or a $C_6$-$C_{40}$ aryloxy group which may optionally be substituted; in one aspect of the present invention, when the polyacene derivative is the pentacene derivative represented by the formula (Ia) above, any one of $R^1$, $R^2$, $R^3$, $R^4$, $R^{5a}$, $R^{5b}$, $R^6$, $R^7$, $R^{8a}$, $R^{8b}$, $R^9$ and $R^{10}$ is preferably a $C_1$-$C_{40}$ hydrocarbon group which may optionally be substituted, a $C_1$-$C_{40}$ alkoxy group which may optionally be substituted, or a $C_6$-$C_{40}$ aryloxy group which may optionally be substituted.

In the formula (I) above, the case that $R^1$, $R^2$, $R^3$, $R^4$, $R^5$, $R^6$, $R^7$, $R^8$, $R^9$, $R^{10}$, $A^1$ and $A^2$ are all hydrogen atoms may be excluded.

In the formula (I) above, when n is 1, at least $R^1$, $R^2$, $R^4$ and $R^9$ may be groups other than hydrogen atom, or at least $R^3$, $R^5$, $R^8$ and $R^{10}$ may be groups other than hydrogen atom, and the cases of (a), (b), (c) and (d) below may be excluded.
(a) when $R^1$, $R^2$, $R^3$, $R^4$, $R^5$, $R^6$, $R^7$, $R^8$, $R^9$, $R^{10}$, $A^1$ and $A^2$ are all methyl groups;
(b) when $R^3$, $R^4$, $R^9$ and $R^{10}$ are all aryl groups that may optionally be substituted;
(c) when $R^1$, $R^2$, $R^4$ and $R^9$ are all alkoxy or aryloxy groups, and $R^3$, $R^5$, $R^6$, $R^7$, $R^8$, $R^{10}$, $A^1$ and $A^2$ are all hydrogen atoms;
(d) when $R^3$, $R^5$, $R^8$ and $R^{10}$ are all alkoxy or aryloxy groups, and $R^1$, $R^2$, $R^4$, $R^6$, $R^7$, $R^9$, $A^1$ and $A^2$ are all hydrogen atoms.

When the polyacene derivative is the pentacene derivative represented by formula (Ia) above, the cases of (a'), (b'), (c') and (d') below may be excluded:

(a') the pentacene derivative represented by formula (Ia) below:

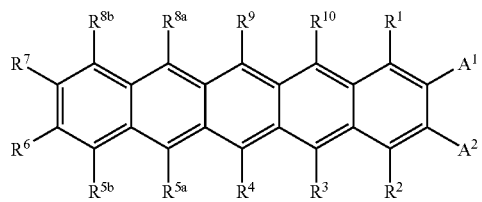

(Ia)

wherein $R^1, R^2, R^3, R^4, R^{5a}, R^{5b}, R^6, R^7, R^{8a}, R^{8b}, R^9, R^{10}, A^1$ and $A^2$ are all methyl groups; or $R^1, R^2, R^3, R^4, R^{5a}, R^{5b}, R^{8a}, R^{8b}, R^9$ and $R^{10}$ are all hydrogen atoms and at least one of $R^6, R^7, A^1$ and $A^2$ is an aryl group; or at least one of $R^1, R^2, R^3, R^4, R^{5a}, R^{5b}, R^6, R^7, R^{8a}, R^{8b}, R^9, R^{10}, A^1$ and $A^2$ is a diarylamine group;

(b') the pentacene derivative represented by formula (Ib) below:

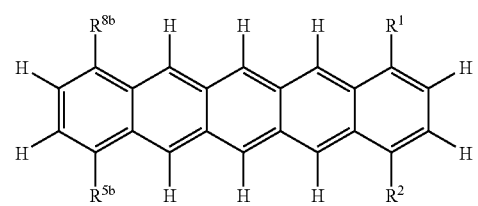

(Ib)

wherein $R^1, R^2, R^{5b}$ and $R^{8b}$ are all alkoxy or aryloxy groups;

(c') the pentacene derivative represented by formula (Ic) below:

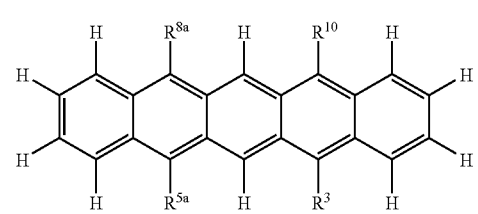

(Ic)

wherein at least 2 of $R^3, R^{5a}, R^{8a}$ and $R^{10}$ are aryl or arylalkynyl groups; or at least one of $R^3, R^{5a}, R^{8a}$ and $R^{10}$ is an arylalkenyl group; or $R^3, R^{5a}, R^{8a}$ and $R^{10}$ are (d') the pentacene derivative represented by formula (Id) below:

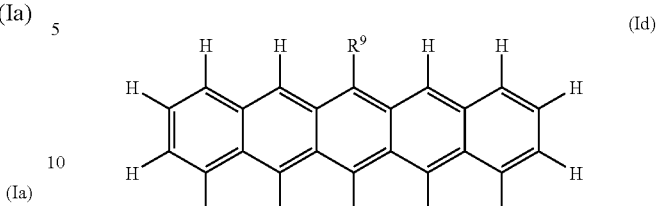

(Id)

wherein $R^4$ and $R^9$ are hydrogen atom, a hydrocarbon group, an alkoxy group, an aryloxy group, a halogen atom or hydroxy group.

Further in one aspect of the present invention, when n is 1, $A^1$ and $A^2$ may be an alkoxycarbonyl group, and $R^1, R^2, R^4$ and $R^9$ may be an alkyl or aryl group; or when n is 1, $A^1, A^2, R^1, R^2, R^4$ and $R^9$ may be an alkyl or aryl group; or further when n is 1, $A^1$ and $A^2$ may be a halogen atom and $R^3, R^5, R^6, R^7, R^8$ and $R^{10}$ may be an alkyl or aryl group.

Further in one aspect of the present invention, when the polyacene derivative is the pentacene derivative represented by the formula (Ia) above, $A^1$ and $A^2$ may be an alkoxycarbonyl group and $R^1, R^2, R^4, R^{5b}, R^6, R^7, R^{8b}$ and $R^9$ may be an alkyl or aryl group; or when the polyacene derivative is the pentacene derivative represented by the formula (Ia) above, $A^1, A^2, R^1, R^2, R^4, R^{5b}, R^6, R^7, R^{8b}$ and $R^9$ may be an alkyl or aryl group; or, when the polyacene derivative is the pentacene derivative represented by the formula (Ia) above, $A^1$ and $A^2$ may be a halogen group and $R^3, R^{5a}, R^{8a}$ and $R^{10}$ may be an alkyl or aryl group.

In another aspect of the present invention, there are provided conductive materials including the polyacene derivatives described above or the polyacene derivatives obtained by the process described above.

In another aspect of the present invention, there are provided resin compositions comprising the polyacene derivative described above or the polyacene derivative obtained by any process described above, and other synthetic organic polymers.

PREFERRED EMBODIMENTS OF THE INVENTION

Figure 1:
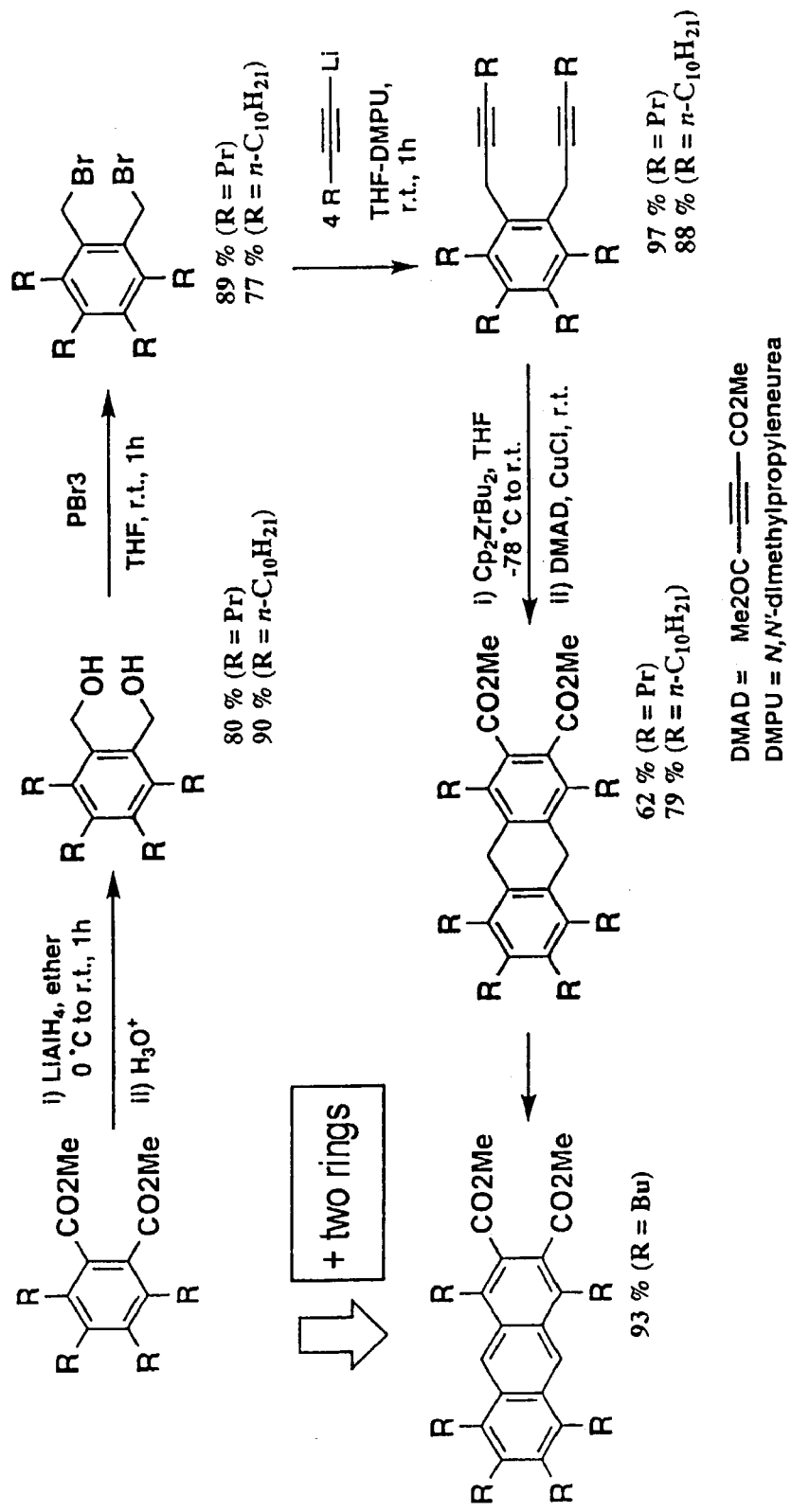
FIG. 1 illustrates an example of the synthesis scheme of polyacene derivatives in accordance with the present invention.

In one aspect of the present invention, there are provided polyacene derivatives represented by formula (I) described below:

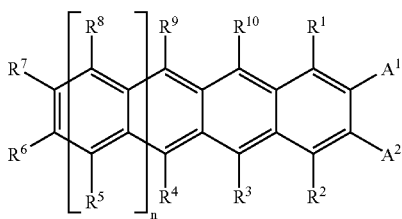

(I)

(wherein $R^1, R^2, R^3, R^4, R^5, R^6, R^7, R^8, R^9, R^{10}$, n, $A^1$ and $A^2$ have the same significance as defined above).

In the specification, the $C_1$-$C_{40}$ hydrocarbon group may be a saturated or unsaturated acyclic group, or a saturated or unsaturated cyclic group. Where the $C_1$-$C_{40}$ hydrocarbon group is acyclic, the group may be linear or branched. The $C_1$-$C_{40}$ hydrocarbon group includes a $C_1$-$C_{40}$ alkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like.

The $C_1$-$C_{40}$ alkyl group, $C_2$-$C_{40}$ alkenyl group, $C_2$-$C_{40}$ alkynyl group, $C_3$-$C_{40}$ allyl group, $C_4$-$C_{40}$ alkyldienyl group and $C_4$-$C_{40}$ polyenyl group are preferably a $C_1$-$C_{20}$ alkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group and a $C_4$-$C_{20}$ polyenyl group, respectively; and more preferably a $C_1$-$C_{10}$ alkyl group, a $C_2$-$C_{10}$ alkenyl group, a $C_2$-$C_{10}$ alkynyl group, a $C_3$-$C_{10}$ allyl group, a $C_4$-$C_{10}$ alkyldienyl group and a $C_4$-$C_{10}$ polyenyl group, respectively.

Examples of the alkyl group useful for practicing the present invention, which may optionally be substituted, are, but not limited thereto, methyl, ethyl, propyl, n-butyl, t-butyl, dodecanyl, trifluoromethyl, perfluoro-n-butyl, 2,2,2-trifluoroethyl, benzyl, 2-phenoxyethyl, etc.

Examples of the aryl group, which is useful for practicing the present invention, are, but not limited thereto, phenyl, 2-tolyl, 3-tolyl, 4-tolyl, naphthyl, biphenyl, 4-phenoxyphenyl, 4-fluorophenyl, 3-carbomethoxyphenyl, 4-carbomethoxyphenyl, etc.

Examples of the alkoxy group useful for practicing the present invention, which may optionally be substituted, are, but not limited thereto, methoxy, ethoxy, 2-methoxyethoxy, t-butoxy, etc.

Examples of the aryloxy group useful for practicing the present invention, which may optionally be substituted, are, but not limited thereto, phenoxy, naphthoxy, phenylphenoxy, 4-methylphenoxy, etc.

Examples of the amino group useful for practicing the present invention, which may optionally be substituted, are, but not limited thereto, amino, dimethylamino, methylamino, methylphenylamino, phenylamino, etc.

The silyl group useful for practicing the present invention, which may optionally be substituted, includes groups shown by formula: —Si($R^{12}$)($R^{13}$)($R^{14}$) (wherein each of $R^{12}$, $R^{13}$ and $R^{14}$, which may be the same or different, independently represents a $C_1$-$C_{40}$ alkyl group which may optionally be substituted with a halogen atom; a $C_6$-$C_{40}$ arylalkyl group which may optionally be substituted with a halogen atom; a $C_1$-$C_{40}$ alkoxy group which may optionally be substituted with a halogen atom; or a $C_6$-$C_{40}$ arylalkyloxy group which may optionally be substituted with a halogen atom).

Examples of the silyl group useful for practicing the present invention, which may optionally be substituted, are, but not limited thereto, trimethylsilyl, triethylsilyl, trimethoxysilyl, triethoxysilyl, diphenylmethylsilyl, triphenylsilyl, triphenoxysilyl, dimethylmethoxysilyl, dimethylphenoxysilyl, methylmethoxyphenyl, etc.

The $C_1$-$C_{40}$ hydrocarbon group, $C_1$-$C_{40}$ alkoxy group, $C_6$-$C_{40}$ aryloxy group, amino group, silyl group, etc. may optimally be substituted, and the substituents are, for example, a halogen atom, hydroxy group, amino group, etc.

Examples of the halogen atom include fluorine atom, chlorine atom, bromine atom and iodine atom. When the hydrogen atom(s) of the $C_1$-$C_{40}$ hydrocarbon group, $C_1$-$C_{40}$ alkoxy group, $C_6$-$C_{40}$ aryloxy group, etc. are substituted with fluorine atom(s), the solubility of the polyacene derivatives increases, which is preferred.

$R^6$ and $R^7$ may be cross-bridged with each other to form a $C_4$-$C_{40}$ saturated or unsaturated ring. The unsaturated ring may be an aromatic ring such as a benzene ring, etc. The ring formed by linking $R^6$ and $R^7$ together is preferably a 4-membered ring to a 16-membered ring, more preferably a 4-membered ring to a 12-membered ring. The ring may be an aromatic ring or an aliphatic ring. The ring may optionally be substituted with substituents such as a $C_1$-$C_{20}$ hydrocarbon group, a $C_1$-$C_{20}$ alkoxy group, a $C_6$-$C_{20}$ aryloxy group, an amino group, hydroxy group, a silyl group, etc.

The saturated or unsaturated ring described above may be intervened by oxygen atom, sulfur atom or the group shown by formula —N($R^{11}$)— (wherein $R^{11}$ is hydrogen atom or a hydrocarbon group). Preferably $R^{11}$ is hydrogen atom or a $C_1$-$C_6$ alkyl group, more preferably hydrogen atom or a $C_1$-$C_4$ alkyl group.

Each of $A^1$ and $A^2$, which may be the same or different, independently represents hydrogen atom; a halogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; a $C_7$-$C_{40}$ alkylaryloxy group which may optionally be substituted; a $C_2$-$C_{40}$ alkoxycarbonyl group which may optionally be substituted; a $C_7$-$C_{40}$ aryloxycarbonyl group which may optionally be substituted; cyano group (—CN); carbamoyl group (—C(=O)NH$_2$); a haloformyl group (—C(=O)—X, wherein X represents a halogen atom); formyl group (—C(=O)—H); isocyano group; isocyanate group; thiocyanate group or thioisocyanate group.

The cyano group (—CN); carbamoyl group (—C(=O) NH$_2$); haloformyl group (—C(=O)—X, wherein X represents a halogen atom); formyl group (—C(=O)—H); isocyano group; isocyanate group; thiocyanate group or thioisocyanate group can be converted from, e.g., an alkoxycarbonyl, in a conventional manner of the organic chemistry. The carbamoyl group (—C(=O)NH$_2$), haloformyl group (—C(=O)—X, wherein X represents a halogen atom), formyl group (—C(=O)—H) or the like can be converted into cyano group or the alkoxycarbonyl group, and vice versa.

$A^1$ and $A^2$ may be cross-bridged with each other to form a ring shown by formula: —C(=O)—B—C(=O)— (wherein B is oxygen atom or a group shown by formula —N($B^1$)— (wherein $B^1$ is hydrogen atom, a $C_1$-$C_{40}$ hydrocarbon group or a halogen atom). For example, when $A^1$ and $A^2$ are alkoxycarbonyl groups, the groups can be converted into the carboxy groups in a conventional manner of the organic chemistry, and the adjacent carboxyl groups can be dehydrated and thus converted into the carboxylic anhydride, namely, a ring shown by formula: —C(=O)—O—C(=O)—. Similarly, the carboxylic anhydride can be converted into the imide, i.e., a ring shown by formula: —C(=O)—N($B^1$)—C(=O)— (wherein $B^1$ has the same significance as defined above) in a conventional manner of the organic chemistry.

n is an integer of not less than 1. When n is 1 and 2, the polyacene derivative represents a 4-cyclic derivative and a 5-cyclic derivative, namely, a naphthacene derivative and a pentacene derivative, respectively.

Heretofore, as the number of aromatic rings in condensed polycyclic aromatic compounds increased, the solubility tended to become poor. In the present invention, however, the solubility can be maintained by introducing a variety of appropriate substituents therein. Thus, n is not limited to 1 and 2 but may be an integer of 3 or more, may be an integer of 4 or more, or may be an integer of 5 or more. For example, a 7 benzene ring-condensed polyacene derivative (which corresponds to the case wherein n is 4) has been produced.

n may be 200 or less, 100 or less, 80 or less, 50 or less, 30 or less, 20 or less, 15 or less, or 10 or less, because it is sufficient to simply repeat this scheme, since the number of n increases two at a time by applying the process of production later described. And, as described above, even though the number of n increases, the solubility can be maintained by appropriately introducing substituents and thus the number of n can be increased.

In the present invention, such compounds that $R^1$, $R^2$, $R^3$, $R^4$, $R^5$, $R^6$, $R^7$, $R^8$, $R^9$, $R^{10}$, $A^1$ and $A^2$ are all hydrogen atoms are not intended as the invention of product, since some of these compounds include those that can be isolated from coal or the like and are publicly known. However, the process of producing such compounds falls within the present invention.

In the present invention, when n is 1 in the formula (I) above, the compounds as the invention of product are intended to include those wherein at least $R^1$, $R^2$, $R^4$ and $R^9$ are groups other than hydrogen atom or at least $R^3$, $R^5$, $R^8$ and $R^{10}$ are groups other than hydrogen atom, but are not intended to include the cases of (a), (b), (c) and (d) described below.
  (a) when $R^1$, $R^2$, $R^3$, $R^4$, $R^5$, $R^6$, $R^7$, $R^8$, $R^9$, $R^{10}$, $A^1$ and $A^2$ are all methyl groups;
  (b) when $R^3$, $R^4$, $R^9$ and $R^{10}$ are all aryl groups that may optionally be substituted;
  (c) when $R^1$, $R^2$, $R^4$ and $R^9$ are all alkoxy or aryloxy groups, and $R^3$, $R^5$, $R^6$, $R^7$, $R^8$, $R^{10}$, $A^1$ and $A^2$ are all hydrogen atoms;
  (d) when $R^3$, $R^5$, $R^8$ and $R^{10}$ are all alkoxy or aryloxy groups, and $R^1$, $R^2$, $R^4$, $R^6$, $R^7$, $R^9$, $A^1$ and $A^2$ are all hydrogen atoms.

Naturally, the process of producing these compounds is within the present invention.

In the present invention, as the invention of product, the compounds of the formula (I) wherein n is 2 are not intended to include the cases of (a'), (b'), (c') and (d') described below. However, the process of producing these compounds is within the present invention.
  (a') the pentacene derivative represented by formula (Ia) below:

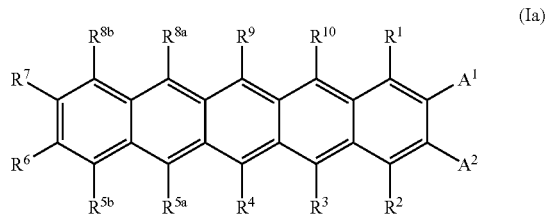

wherein $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are all methyl groups; or $R^1$, $R^2$, $R^3$, $R^4$, $R^{5a}$, $R^{5b}$, $R^{8a}$, $R^{8b}$, $R^9$, $R^{10}$, are all hydrogen atoms and at least one of $R^6$, $R^7$, $A^1$ and $A^2$ is an aryl group; or at least one of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ is a diarylamine group
  (b') the pentacene derivative represented by formula (Ib) below:

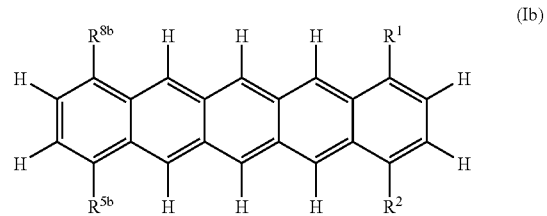

wherein $R^1$, $R^2$, $R^{5b}$ and $R^{8b}$ are all alkoxy or aryloxy groups;
  (c') the pentacene derivative represented by formula (Ic) below:

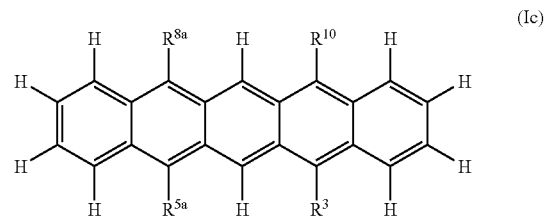

wherein at least 2 of $R^3$, $R^{5a}$, $R^{8a}$ and $R^{10}$ are aryl or arylalkynyl groups; or at least one of $R^3$, $R^{5a}$, $R^{8a}$ and $R^{10}$ is an arylalkenyl group; or $R^3$, $R^{5a}$, $R^{8a}$ and $R^{10}$ are all alkoxy or aryloxy groups;
  (d') the pentacene derivative represented by formula (Id) below:

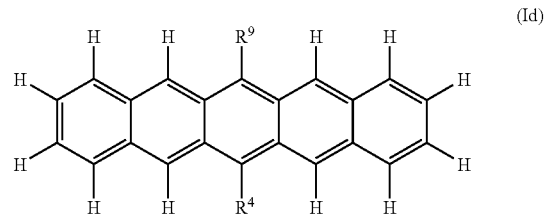

wherein $R^4$ and $R^9$ are hydrogen atom, a hydrocarbon group, an alkoxy group, an aryloxy group, a halogen atom or hydroxy group.

In the polyacene derivatives represented by formula (I), preferably at least 5 of $R^1$, $R^2$, $R^3$, $R^4$, $R^5$, $R^6$, $R^7$, $R^8$, $R^9$, $R^{10}$, $A^1$ and $A^2$ are groups other than hydrogen atom, more preferably at least 6 of $R^1$, $R^2$, $R^3$, $R^4$, $R^5$, $R^6$, $R^7$, $R^8$, $R^9$, $R^{10}$, $A^1$ and $A^2$ are groups other than hydrogen atom, much more preferably at least 8 of $R^1$, $R^2$, $R^3$, $R^4$, $R^5$, $R^6$, $R^7$, $R^8$, $R^9$, $R^{10}$, $A^1$ and $A^2$ are groups other than hydrogen atom, and most preferably at least 10 of $R^1$, $R^2$, $R^3$, $R^4$, $R^5$, $R^6$, $R^7$, $R^8$, $R^9$, $R^{10}$, $A^1$ and $A^2$ are groups other than hydrogen atom. This is because there is a tendency that as the number of hydrogen atom in $R^1$, $R^2$, $R^3$, $R^4$, $R^5$, $R^6$, $R^7$, $R^8$, $R^9$, $R^{10}$, $A^1$ and $A^2$ increases, the yield occasionally decreases when dehydrogenation is carried out using the combination of a lithium dopant and a lithium-removing reagent.

When the polyacene derivatives represented by formula (I) are the pentacene derivatives shown by formula (Ia) below:

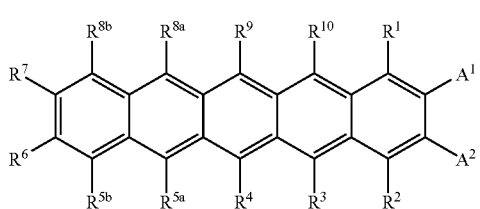

(wherein $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ have the same significance as defined above), preferably at least 5 of $R^1$, $R^2$, $R^3$, $R^4$, $R^{5a}$, $R^{5b}$, $R^6$, $R^7R^{8a}$, $R^{8b}$, $R^9$, $R^{10}$, $A^1$ and $A^2$ are groups other than hydrogen atom. More preferably, at least 6 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$, and $A^2$ are groups other than hydrogen atom; further more preferably, at least 7 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom; much more preferably, at least 8 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom; further much more preferably, at least 9 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom; and most preferably, at least 10 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom.

In one embodiment of the present invention, any one of the combinations of $R^1$ and $R^2$, $R^3$ and $R^{10}$, $R^4$ and $R^5$ and $R^6$ and $R^1$, and $A^1$ and $A^2$ are preferably the same substituents, and more preferably, $R^1$ and $R^2$ are the same substituents, $R^3$ and $R^{10}$ are the same substituents, $R^4$ and $R^9$ are the same substituents, $R^5$ and $R^8$ are the same substituents, $R^6$ and $R^7$ are the same substituents, and $A^1$ and $A^2$ are the same substituents. This is because it becomes easy to synthesize such polyacene derivatives with the improved yield.

For the same reason, in another aspect of the invention, when the polyacene derivatives described above are the pentacene derivatives shown by formula (Ia) above, any one of the combinations of $R^1$ and $R^2$, $R^3$ and $R^{10}$, $R^4$ and $R^9$, $R^{5a}$ and $R^{8a}$, $R^{5b}$ and $R^{8b}$, $R^6$ and $R^7$, and $A^1$ and $A^2$ are preferably the same substituents, and more preferably, $R^1$ and $R^2$ are the same substituents, $R^3$ and $R^{10}$ are the same substituents, $R^4$ and $R^9$ are the same substituents, $R^{5a}$ and $R^{8a}$ are the same substituents, $R^{5b}$ and $R^{8b}$ are the same substituents, $R^6$ and $R^7$ are the same substituents, and $A^1$ and $A^2$ are the same substituents. This is because it becomes easy to synthesize such polyacene derivatives with the improved yield.

Alternatively, from the viewpoints that the synthesis of the polyacene derivatives becomes easy and the yield is improved, $R^1$ and $R^2$ are preferably the same substituents, $R^3$ and $R^{10}$ are preferably the same substituents, $R^4$ and $R^9$ are preferably the same substituents, $R^5$ and $R^8$ ($R^{5a}$ and $R^{8a}$ or $R^{5b}$ and $R^{8b}$ when the polyacene derivatives described above are the pentacene derivatives shown by formula (Ia) above) are preferably the same substituents, $R^6$ and $R^7$ are preferably the same substituents, and $A^1$ and $A^2$ are preferably the same substituents.

In one embodiment of the invention, when n is 1, $A^1$ and $A^2$ may be an alkoxycarbonyl group, and $R^1$, $R^2$, $R^4$ and $R^9$ may be an alkyl or aryl group. Also, when n is 1, $A^1$, $A^2$, $R^1$, $R^2$, $R^4$ and $R^9$ may be an alkyl or aryl group. Further when n is 1, $A^1$ and $A^2$ are a halogen atom and $R^3$, $R^5$, $R^6$, $R^7$, $R^8$ and $R^{10}$ may be an alkyl or aryl group.

In one embodiment of the present invention, when the polyacene derivatives are the pentacene derivatives represented by the formula (Ia) above, $A^1$ and $A^2$ may be an alkoxycarbonyl group and $R^1$, $R^2$, $R^4$, $R^{5b}$, $R^6$, $R^7$, $R^{8b}$ and $R^9$ may be an alkyl or aryl group. Also, when the polyacene derivatives are the pentacene derivatives represented by the formula (Ia) above, $A^1$, $A^2$, $R^1$, $R^2$, $R^4$, $R^{5b}$, $R^6$, $R^7$, $R^{8b}$ and $R^9$ may be an alkyl or aryl group. Furthermore, when the polyacene derivatives are the pentacene derivatives represented by the formula (Ia) above, $A^1$ and $A^2$ may be a halogen atom and $R^3$, $R^{5a}$, $R^{8a}$ and $R^{10}$ may be an alkyl or aryl group.

In one aspect of the present invention, there is provided a process of producing the polyacene derivatives represented by formula (I) above, which comprises aromatizing the hydrocarbon condensed rings represented by formula (II) below:

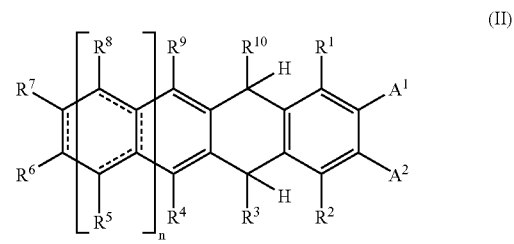

(wherein $R^1$, $R^2$, $R^3$, $R^4$, $R^5$, $R^6$, $R^7$, $R^8$, $R^9$, $R^{10}$, $A^1$, $A^2$ and n have the same significance as defined above;

the bond shown by formula below represents a single bond or a double bond;

═══), in the presence of a dehydrogenation reagent.

The hydrocarbon condensed rings shown by formula (II) above include, e.g., the following hydrocarbon condensed rings represented by (IIa), (IIb) and (IIc), depending upon the kind of bonding:

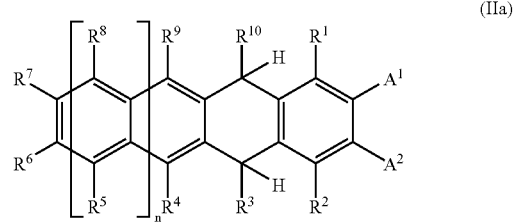

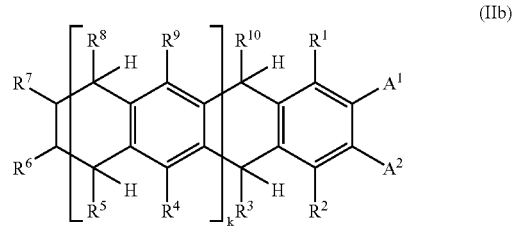

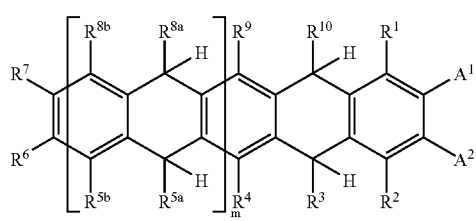

(IIc)

(wherein $R^1$, $R^2$, $R^3$, $R^4$, $R^5$, $R^{5a}$, $R^{5b}$, $R^6$, $R^7$, $R^8$, $R^{8a}$, $R^{8b}$, $R^9$, $R^{10}$, $A^1$, $A^2$ and n have the same significance as defined above).

When n represents an odd number and the hydrocarbon condensed rings shown by formula (II) described above are those shown by formula (IIb) above, k is an integer shown by (n+1)/2, and when n represents an even number and the hydrocarbon condensed rings shown by formula (II) described above are those shown by formula (IIc) above, m is an integer shown by n/2.

In the hydrocarbon condensed rings shown by formula (IIa), it turns out that one ring is aromatized. On the other hand, in the hydrocarbon condensed rings shown by formula (IIb) and formula (IIc), it turns out that two or more rings are aromatized.

As a matter of course, the hydrocarbon condensed rings shown by formula (II) also include the cases wherein the rings in a repeating unit being an aromatic ring and a non-aromatic ring are repeated at random.

In one embodiment of the invention, the dehydrogenation reagent is a combination of a lithium dopant and a lithium-removing reagent. It is preferred to add the lithium dopant first to the hydrocarbon condensed rings followed by adding the lithium-removing reagent.

This scheme is illustratively shown with the cases of the hydrocarbon condensed rings shown by formula (IIa), (IIb) and (IIc) below.

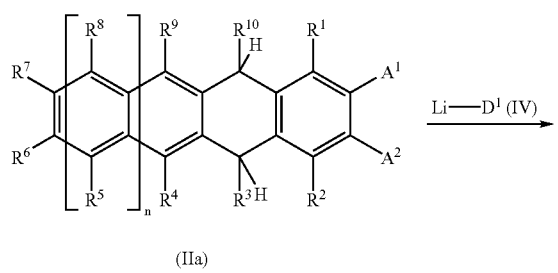

(IIa)

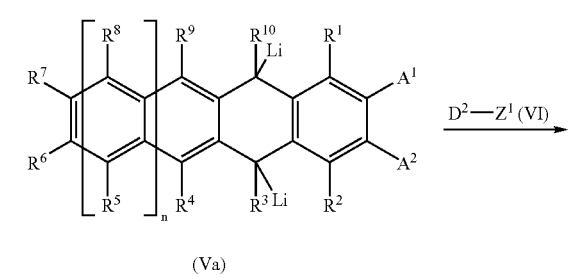

(Va)

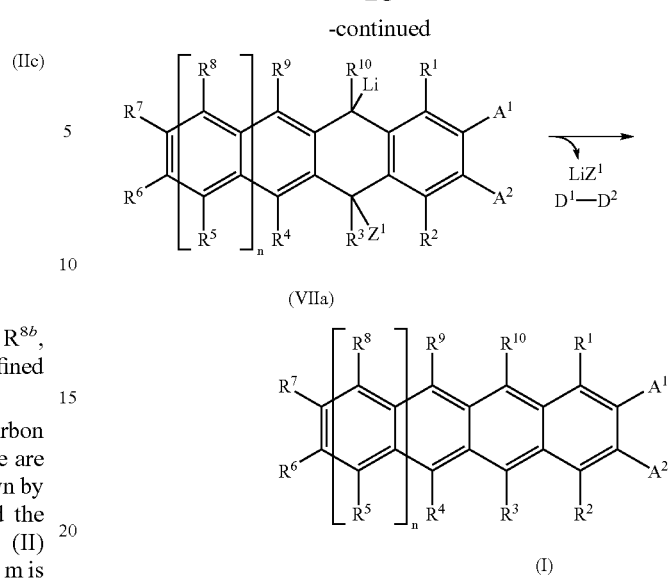

(VIIa)

(I)

(wherein $R^1$, $R^2$, $R^3$, $R^4$, $R^5$, $R^6$, $R^7$, $R^8$, $R^9$, $R^{10}$, $A^1$, $A^2$, and n the same significance as defined above; $D^1$ represents a nucleophilic group such as a $C_1$-$C_6$ alkyl group, etc.; $D^2$ represents a $C_1$-$C_{20}$ hydrocarbon group such as a $C_1$-$C_6$ alkyl group, etc.; and $Z^1$ represents an eliminable group such as a halogen atom, etc.).

In this reaction, $R^3$ and $R^{10}$ in formula (IIa) are preferably hydrogen atoms, in view of easy synthesis of the polyacene derivatives.

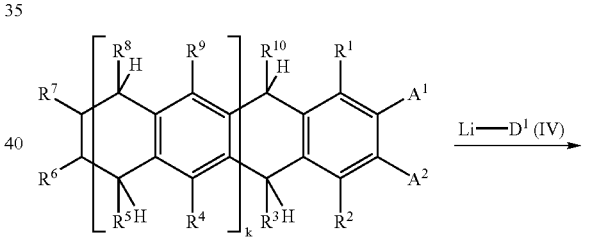

(IIb)

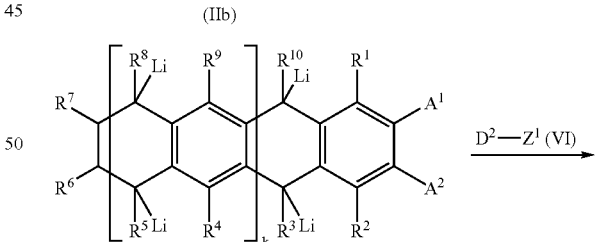

(Vb)

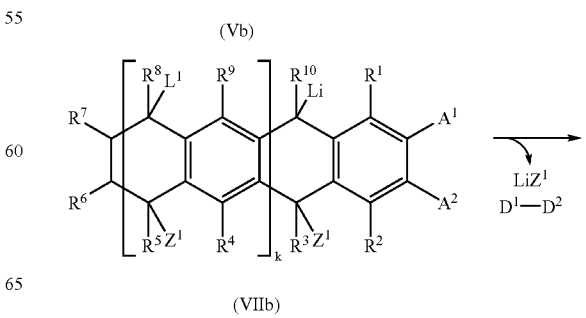

(VIIb)

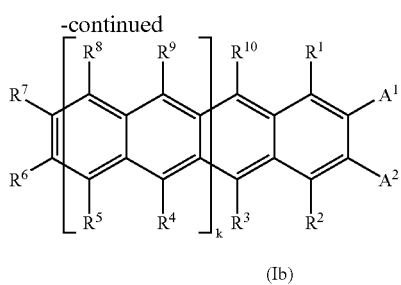

(Ib)

(wherein $R^1$, $R^2$, $R^3$, $R^4$, $R^5$, $R^6$, $R^7$, $R^8$, $R^9$, $R^{10}$, $A^1$, $A^2$ and k have the same significance as defined above; $D^1$ represents a nucleophilic group such as a $C_1$-$C_6$ alkyl group, etc.; $D^2$ represents a $C_1$-$C_{20}$ hydrocarbon group such as a $C_1$-$C_6$ alkyl group, etc.; and $Z^1$ represents an eliminable group such as a halogen atom, etc.).

In this reaction, $R^3$, $R^5$, $R^8$ and $R^{10}$ in formula (IIb) are preferably hydrogen atoms, atoms, in view of easy synthesis of the polyacene derivatives.

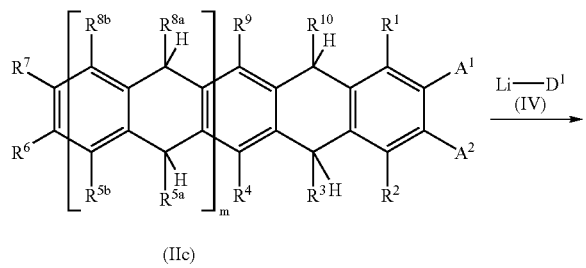

(IIc)

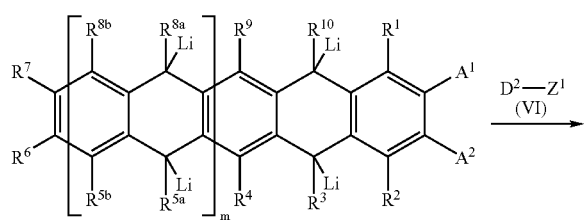

(Vc)

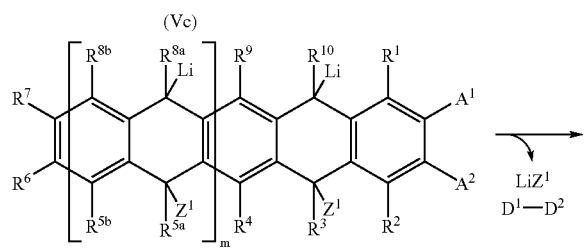

(VIIc)

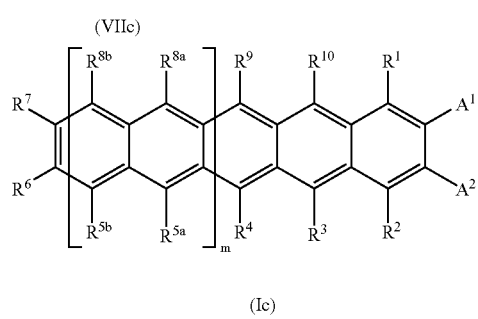

(Ic)

(wherein $R^1$, $R^2$, $R^3$, $R^4$, $R^5$, $R^6$, $R^7$, $R^8$, $R^9$, $R^{10}$, $A^1$, $A^2$ and m have the same significance as defined above; $D^1$ represents a nucleophilic group such as a $C_1$-$C_6$ alkyl group, etc.; $D^2$ represents a $C_1$-$C_{20}$ hydrocarbon group such as a $C_1$-$C_6$ alkyl group, etc.; and $Z^1$ represents an eliminable group such as a halogen atom, etc.).

In this reaction, $R^3$, $R^{5a}$, $R^{8a}$ and $R^{10}$ in formula (IIc) are preferably hydrogen atoms, in view of easy synthesis of the polyacene derivatives.

In the schemes described above, the hydrocarbon condensed rings represented by formula (IIa), (IIb) or (IIc) are employed, for the sake of explanation to clarify the carbon atoms on which the lithium dopant (IV) shown by Li-$D^1$ acts. It goes without saying that the dehydrogenation reagent in the combination of the lithium dopant and the lithium-removing reagent is widely applicable to the hydrocarbon condensed rings shown by formula (II) described above.

The lithium dopant (IV) is reacted with the hydrocarbon condensed rings represented by formulae (IIa), (IIb) and (IIc) to obtain the lithium-provided hydrocarbon condensed rings shown by formula (Va), (Vb) and (Vc), respectively. Preferred lithium dopants include a $C_1$-$C_{20}$ hydrocarbon lithium such as an alkyl lithium, an aryl lithium, etc. For example, a $C_1$-$C_6$ alkyl lithium such as butyl lithium, etc., a $C_6$-$C_{20}$ aryl lithium such as phenyl lithium, etc. are preferably used.

It is preferred that an activator of the lithium dopant co-exists together with the lithium dopant (IV). As the activator, tertiary amines are preferred and, N,N,N',N'-tetraalkylalkylenediamines such as N,N,N',N'-tetramethylethylene-diamine (TMEDA), are employed. It is likely that the alkyl lithium would be present in a solution as an oligomer like a tetramer. When a tertiary amine is co-present, it is assumed that the nitrogen atom of the amine would be coordinated on the lithium atom of the alkyl lithium to cleave the oligomer structure, whereby the lithium atom in the alkyl lithium would be exposed to the solution to improve the reactivity.

A preferred solvent is an organic solvent. In particular, a non-polar organic solvent is employed. For example, an alkane such as hexane, etc. and an aromatic compound such as benzene, etc. are preferred.

A preferred reaction temperature is from 0° C. to 200° C., more preferably 20° C. to 100° C., and most preferably 30° C. to 80° C.

When the lithium-removing reagent (VI) is reacted with the hydrocarbon condensed rings shown by formulae (Va), (Vb) and (Vc), it is surmised to form the intermediates shown by formulae (VIIa), (VIIb) and (VIIc), respectively. The intermediates are decomposed to give the polyacene derivatives shown by formula (I), (Ib) or (Ia).

As the lithium-removing reagent (VI), for example, alkyl halides are advantageously used. Preferred examples of alkyl halides are alkyl halides having 6 or less carbon atoms, such as methyl iodide, ethyl bromide, etc.

Where the lithium dopant (IV) and the lithium-removing reagent (VI) having less carbon atoms, such as, butyl lithium and methyl iodide are used as the lithium dopant (IV) and the lithium-removing reagent (VI), respectively, lithium iodide and hexane will be split off. Hexane can be removed at the same time when the solvent is removed. Lithium iodide can be removed by washing the resulting reaction mixture with water. Thus, the combination of the lithium dopant and the lithium-removing reagent renders purification of the reaction mixture extremely easy and is desirable.

When a large number of hydrogen atoms are introduced on $R^1$, $R^2$, $R^3$, $R^4$, $R^5$, $R^6$, $R^7$, $R^8$, $R^9$, $R^{10}$, $A^1$ and $A^2$, e.g., when at least 8 of these groups are hydrogen atoms, the yield of the polyacene derivative shown by formula (I) based on the hydrocarbon condensed rings of formula (IIa) is approximately 50%. On the other hand, when at least 6, especially 8 or more groups other than hydrogen atom are introduced on $R^1$, $R^2$, $R^3$, $R^4$, $R^5$, $R^6$, $R^7$, $R^8$, $R^9$, $R^{10, 41}$ and $A^2$, there is a tendency that the yield increases. For example, the yield occasionally reaches 90% or more, or sometimes becomes 95% or more.

In another embodiment of the present invention, the dehydrogenation reagent described above is preferably a compound shown by formula (III) below:

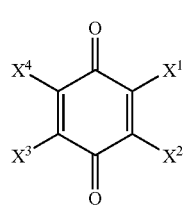

(III)

(wherein each of $X^1$, $X^2$, $X^3$ and $X^4$, which may be the same or different, independently represents a halogen atom or cyano group).

The quinones shown by formula (III) above are reacted with the compounds represented by formula (II) above to become 1,4-dihydroxy-cyclohexane derivatives.

In the quinines shown by formula (III) above, the halogen atom is preferably chlorine atom, bromine atom or iodine atom, more preferably chlorine atom or bromine atom, and most preferably chlorine atom.

For example, all of $X^1$, $X^2$, $X^3$ and $X^4$ may be chlorine atoms. That is, the quinone may be chloranil. Or, $X^1$ and $X^2$ may be cyano group, and $X^3$ and $X^4$ may be chlorine atoms. That is, it may be 2,3-dichloro-5,6-dicyanoquinone. Or again, $X^1$, $X^2$, $X^3$ and $X^4$ may all be cyano groups. That is, it may be 2,3,5,6-tetracyanoquinone.

When the quinones shown by formula (III) above are used, the quinones shown by formula (III) above may occasionally undergo Diels-Alder reaction with the polyacene derivative products to produce by-products. If desired, the by-products are removed by column chromatography, etc.

In order to prevent the production of such by-products, the quinones shown by formula (III) above are used preferably in 0.9 to 1.2 equivalents, more preferably 0.9 to 1.15 equivalents, and most preferably 0.95 to 1.05 equivalents, based on the compounds shown by formula (II) described above.

As the solvent, an organic solvent is preferred, and an aromatic compound such as benzene, etc. is particularly preferred.

The reaction temperature is preferably between –80° C. to 200° C., more preferably 0° C. to 100° C., and most preferably 10° C. to 80° C. If desired, the reaction may be performed under light shielding.

In other embodiment of the present invention, it is preferred that the dehydrogenation reagent described above includes palladium. For example, palladium carried on carbon such as activated carbon, which is commercially available as so-called palladium carbon, may preferably be employed. Pd/C is a catalyst that has been widely used for dehydrogenation, and can be used in the present invention as in a conventional manner. The reaction temperature is, e.g., from 200° C. to 500° C. Of course, the reaction temperature may appropriately be set forth, depending upon various conditions such as starting materials, etc.

The hydrocarbon condensed rings can be obtained, e.g., by the following scheme.

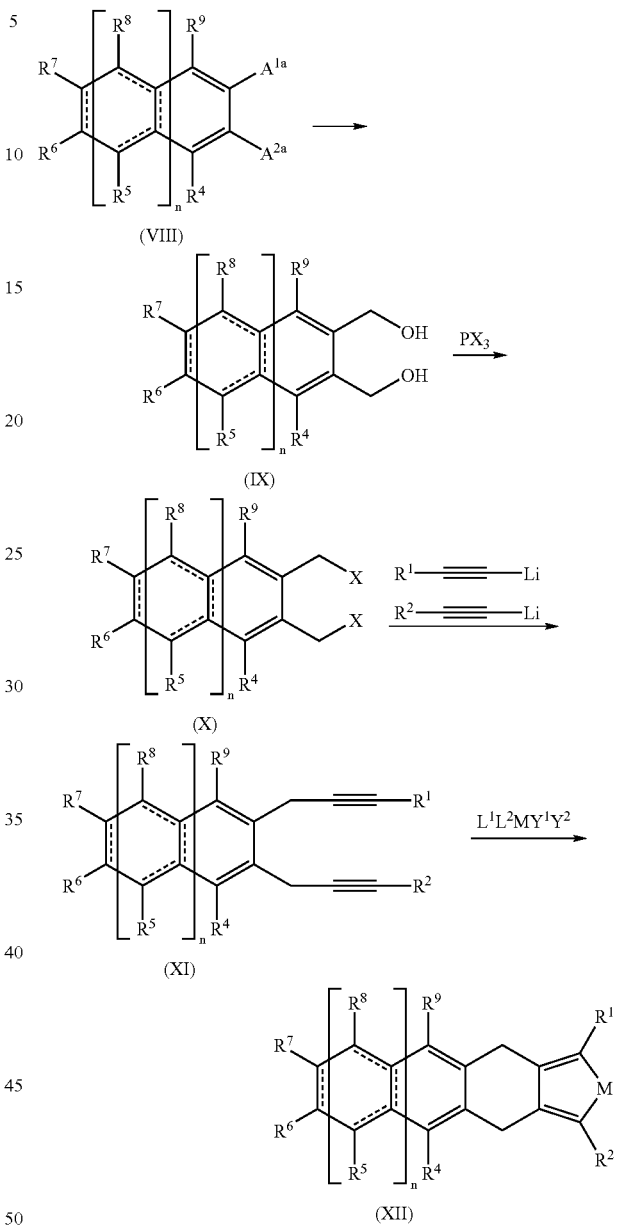

(wherein $R^1$, $R^2$, $R^4$, $R^5$, $R^6$, $R^7$, $R^8$, $R^9$ and n have the same significance as defined above; each of $A^{1a}$ and $A^{2a}$, which may be the same or different, independently represents a $C_6$-$C_{40}$ alkoxycarbonyl group which may optionally be substituted with a substituent comprising a halogen atom, or a $C_6$-$C_{40}$ aryloxycarbonyl group which may optionally be substituted a substituent comprising with a halogen atom; and X is an eliminable group such as a halogen atom, etc.;

the bond shown by formula below represents a single bond or a double bond;

-----

M represents a metal belonging to Group III to Group V or a lanthanide metal;

each $L^1$ and $L^2$, which may be the same or different, independently represents an anionic ligand, provided that $L^1$ and $L^2$ may be cross-bridged with each other; and, each of $Y^1$ and $Y^2$, which may be the same or different, independently represents an eliminable group).

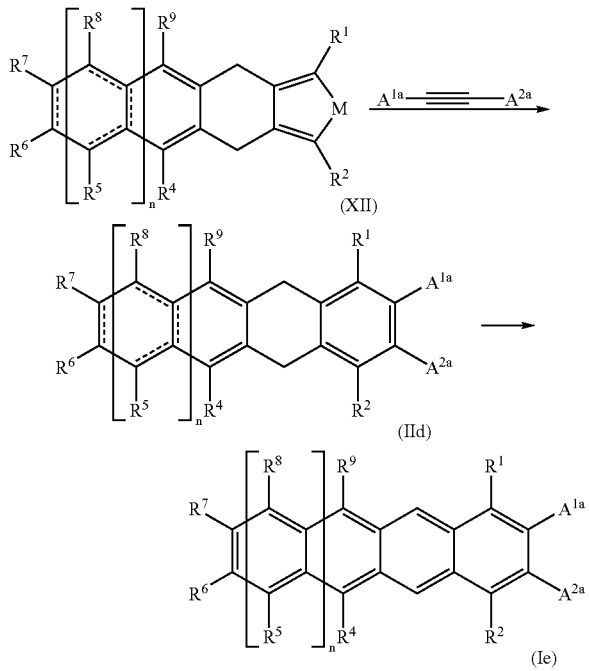

(wherein $R^1$, $R^2$, $R^4$, $R^5$, $R^6$, $R^7$, $R^8$, $R^9$, n, $A^{1a}$ and $A^{2a}$ have the same significance as defined above;
the bond shown by formula below represents a single bond or a double bond;
╤╤╤╤).

First, the diester (VIII) is reduced with a reducing agent to give the diol (IX). As the reducing agent, lithium aluminum hydride can be used. As a solvent, an organic solvent is preferably used, and a polar organic solvent may be used. For example, an ether such as diethyl ether, THF, etc. may be used.

The reaction temperature is preferably between −80° C. and 200° C., more preferably between −50° C. and 100° C., and most preferably between −20° C. and 80° C. After the reducing agent is added, the reaction may be quenched by adding water, a weak acid, etc.

If desired, the diester (VIII) may be hydrated under acidic or alkaline conditions to convert into the dicarboxylic acid, the dicarboxylic acid may be reduced to the diketone and then the diketone may be reduced to the diol.

Subsequently, the diol (IX) is reacted with a phosphorus trihalide such as phosphorus tribromide, etc., or with $SOCl_2$, etc. to convert into the dihalogen (X). It is preferred to use an organic solvent as the solvent, wherein a polar organic solvent may be used. For example, an ether such as THF may be used. The reaction temperature is preferably between −80° C. and 200° C., more preferably between −50° C. and 100° C., and most preferably between −20° C. and 80° C.

Next, an alkynyl lithium is reacted with the dihalogen (X) to give the dialkyne (XI). Preferably, the coupling reaction is carried out in the co-presence of a stabilizer such as N,N'-dimethylpropyleneurea, hexamethylphosphamide, etc. As a solvent, it is preferred to use an organic solvent, in which a polar organic solvent is preferably employed. For example, an ether such as THF may be used. The reaction temperature is preferably between −80° C. and 200° C., more preferably between −50° C. and 100° C., and most preferably between −20° C. and 80° C.

The dialkyne (XI) is reacted with an organic metal compound shown by $L^1L^2MY^1Y^2$ such as a biscyclopentadienylzirconium dialkyl to form the metallacyclopentadiene (XII). The formation of a metallacyclopentadiene from an organic metal compound shown by $L^1L^2MY^1Y^2$ is described in, e.g., T. Takahashi, et al., J. Org. Chem., 1995, 60, 4444, and the reaction proceeds under the same conditions as the literature, or under conditions closely similar to the literature.

As a solvent, either an aliphatic or aromatic solvent is used, preferably a polar solvent. An ethereal solvent, e.g., tetrahydrofuran or diethyl ether; a halogenated hydrocarbon such as methylene chloride; a halogenated aromatic hydrocarbon such as o-dichlorobenzene; an amide such as N,N-dimethylformamide, etc., a sulfoxide such as dimethyl sulfoxide, etc., are used. Alternatively, an aromatic hydrocarbon such as benzene, toluene, xylene, etc. may be used as the aromatic solvent.

The reaction is preferably carried out at a temperature ranging from −80° C. to 300° C., more preferably from 0° C. to 150° C. The pressure is within 0.1 bar to 2500 bars, preferably within 0.5 bar to 10 bars. The reaction may be carried out continuously or batch-wise, in one step or a multiple step, in a solution or in a suspension, in a gaseous phase or in a supercritical medium.

M represents a metal belonging to Group III to Group V or a lanthanide metal. Preferred examples of M include metals of Group IV or the lanthanide group in the Periodic Table, more preferably, the metals of Group IV, namely, titanium, zirconium and hafnium.

Each $L^1$ and $L^2$, which may be the same or different, independently represents an anionic ligand.

The anionic ligand above is preferably a non-localized cyclic $\eta^5$-coordinated ligand, a $C_1$-$C_{20}$ alkoxy group, a $C_6$-$C_{20}$ aryloxy group or a diakylamide group.

$L^1$ and $L^2$ is preferably a non-localized cyclic $\eta^5$-coordinated ligand. The non-localized cyclic $\eta^5$-coordinated ligand includes unsubstituted cyclopentadienyl group and a substituted cyclopentadienyl group. Examples of the substituted cyclopentadienyl group are methylcyclopentadienyl, ethylcyclopentadienyl, isopropylcyclopentadienyl, n-butylcyclopentadienyl, t-butylcyclopentadienyl, dimethylcyclopentadienyl, diethylcyclopentadienyl, diisopropylcyclopentadienyl, di-t-butylcyclopentadienyl, tetramethylcyclopentadienyl, indenyl, 2-methylindenyl, 2-methyl-4-phenylindenyl, tetrahydroindenyl, benzindenyl, fluorenyl, benzofluorenyl, tetrahydrofluorenyl and octahydrofluorenyl.

In the non-localized cyclic $\eta^5$-coordinated ligand, one or more atom(s) in the non-localized cyclic $\pi$ system may be substituted with a hetero atom(s). In addition to hydrogen, the hetero atoms may include one or more hetero atoms such as the elements of Group XIV of the Periodic Table and/or the elements of Groups XV, XVI and XVII of the Periodic Table.

The non-localized cyclic $\eta^5$-coordinated ligand, e.g., cyclopentadienyl group, may form a ring together with the central metal, or may be cross-bridged by one or more cross-bridging ligands. Examples of the cross-bridging ligands are $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $(C_6H_5)_2Ge$, $(C_6H_5)_2Sn$, $(CH_2)_4Si$, $CH_2Si(CH_3)_2$, o-$C_6H_4$ or 2,2'-$(C_6H_4)_2$.

Two or more non-localized cyclic $\eta^5$-coordinated ligands, e.g., cyclopentadienyl groups, may be cross-bridged by one or more cross-bridging groups which may contains ring(s). Examples of the cross-bridging groups include $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $(C_6H_5)_2Ge$, $(C_6H_5)_2Sn$, $(CH_2)_4Si$, $CH_2Si(CH_3)_2$, o-$C_6H_4$ or 2,2'-$(C_6H_4)_2$.

The metallacyclopentadiene further includes compounds containing two or more metallacyclopentadiene moieties. Such compounds are known as a polynuclear metallocene. The polynuclear metallocene may take any mode of substitution or any cross-bridged form. In the independent metallocene moiety of the polynuclear metallocene above, the respective moieties may be the same or different. Examples of the polynuclear metallocene are described in, e.g., EP-A No. 632,063, JPA Nos. H4-80214 and H4-85310 and EP-A No. 654,476.

Each of $Y^1$ and $Y^2$, which may be the same or different, independently represents an eliminable group. Examples of the eliminable group include a halogen atom such as F, Cl, Br or I, a $C_1$-$C_{20}$ alkyl group such as n-butyl, etc., a $C_6$-$C_{20}$ aryl group such as phenyl, etc.

The reaction described above is carried out preferably at a temperature ranging from −120° C. to 50° C., more preferably from −120° C. to 0° C.

Next, in one embodiment of the present invention, the metallacyclopentadiene (XII) is reacted with an alkyne to form a benzene ring, whereby the hydrocarbon condensed rings (IId). Typically, an alkyne is added to the reaction mixture, without isolating the metallacyclopentadiene (XII).

A metallacyclopentadiene such as zirconacyclopentadiene is reacted with an alkyne in the presence of CuCl to form a benzene ring, which is described in T. Takahashi, et al., J. Am. Chem. Soc., 1998, 120, 1672-1680. The reaction can be proceeded under the same conditions as the literature, or under conditions closely similar to the literature.

Not only CuCl but a metal compound may also be used. Preferably, the metal compound is the metal compound of Groups IV through XV in the Periodic Table. The metal compound above may be a salt like CuCl or may be an organic metal complex.

Examples of the salt include a metal salt such as CuX, $NiX_2$, $PdX_2$, $ZnX_2$, $CrX_2$, $CrX_3$, $CoX_2$ or $BiX_3$ (wherein X represents a halogen atom such as chlorine atom, bromine atom, etc.).

As the metal compound, there may be employed an organic metal complex, especially a nickel complex. As the organic metal complex, there are employed those wherein ligands such as phosphines; aromatic amines, e.g., pyridine, bipyridine, etc., halogen atoms, or the like are coordinated to the central metals of Groups III through XI of the Periodic Table, preferably to the central metals of Groups VI to XI of the Periodic Table. The central metals are preferably so-called 4- to 6-coordinated, and the metals of Group X in the Periodic Table are particularly preferred. Phosphines include triphenylphosphine, methyldiphenylphosphine, etc. and are not particularly limited. Examples of the organic metal complex include bis(triphenylphosphine)dichloronickel, dichloro(2, 2'-bipyridyl)nickel and $PdCl_2$(2,2'-bipyridine). It is described in T. Takahashi, et al., J. Am. Chem. Soc., Vol. 121, No. 48, 1999, 11095 that a metallacyclopentadiene such as zirconacyclopentadiene is reacted with an alkyne in the presence of a nickel phosphine complex to form a benzene ring.

The reaction is carried out preferably at a temperature ranging from −80° C. to 300° C., more preferably from 0° C. to 150° C. The pressure is within 0.1 bar to 2500 bars, preferably within 0.5 bar to 10 bars. The reaction may be carried out continuously or batch-wise, in one step or a multiple step, in a solution or in a suspension, in a gaseous phase or in a supercritical medium.

As a solvent, an aliphatic or aromatic solvent is used, preferably a polar solvent. An ethereal solvent, e.g., tetrahydrofuran or diethyl ether; a halogenated hydrocarbon such as methylene chloride; a halogenated aromatic hydrocarbon such as o-dichlorobenzene; an amide such as N,N-dimethylformamide, etc., a sulfoxide such as dimethyl sulfoxide, etc., are used.

The reaction is carried out preferably in the presence of a stabilizer, which stabilizes the metal compound in the solvent. Especially when the metal compound is a metal salt and the solvent is an organic solvent, the stabilizer can stabilize the metal salt in the organic solvent. Examples of the stabilizer include N,N'-dimethylpropyleneurea, hexamethylphosphoamide, tec.

Then, the hydrocarbon condensed rings (IId) are aromatized through the aromatizing reaction described above to give the polyacene derivative (Ie).

According to the scheme described above, the polyacene derivative (Ie) wherein $R^3$ and $R^{10}$ are hydrogen atoms can be produced. The polyacene derivative wherein $R^3$ and $R^{10}$ are groups other than hydrogen atom can be produced, e.g., by the following scheme.

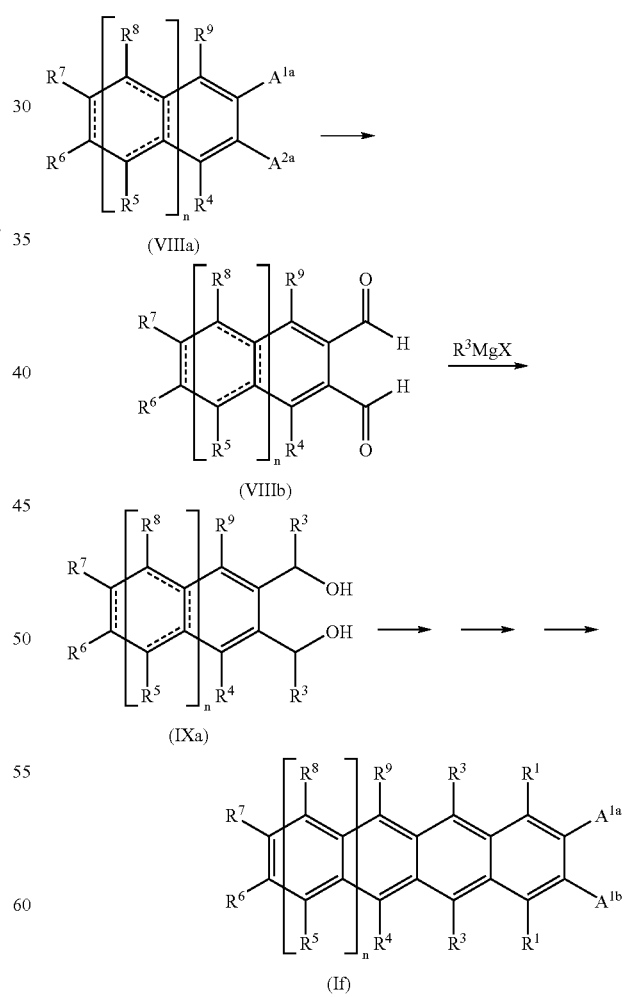

(wherein $R^1$, $R^2$, $R^3$, $R^4$, $R^5$, $R^6$, $R^7$, $R^8$, $R^9$, n, $A^{1a}$ and $A^{2a}$ have the same significance as defined above;

the bond shown by formula below represents a single bond or a double bond;

-----).

The diester (VIIIa) is reduced to the dialdehyde (VIIIb), using a reducing agent such as diisobutyl aluminum hydride, etc. Using an organic solvent, e.g., toluene, etc., the reaction is allowed to proceed at −100° C. to −50° C., preferably at −78° C. It is preferred to use precisely one equivalent each of the diester and the reducing agent.

Or, the diester (VIIIa) is hydrolyzed under acidic or basic conditions to form the dicarboxylic acid. The dicarboxylic acid may be reduced to the dialdehyde (VIIIb), using a reducing agent.

The dialdehyde (VIIIb) is then reacted with Grignard reagent to form the diol (IXa). After that, the diol (IXa) may be reacted as described above.

Or again, in one embodiment of the present invention, the metallacyclopentadiene (XII) described above may be reacted with an ortho-dihalogenoarene such as 1,2-diiodobenzene, or a tetrahalogenoarene such as a 1,2,4,5-tetrahalogenobenzene to form the arene ring.

The coupling reaction is carried out typically in the presence of a metal compound such as CuCl and a stabilizer. The metal compound is preferably the metal compound of Groups IV to XV in the Periodic Table. The metal compound described above may be a salt such as CuCl or an organic metal complex. Examples of the salt include a metal salt such as $CuX$, $NiX_2$, $PdX_2$, $ZnX_2$, $CrX_2$, $CrX_3$, $CoX_2$ or $BiX_3$ (wherein X represents a halogen atom such as chlorine atom, bromine atom, etc.).

Preferably, a stabilizer such as N,N'-dimethylpropyleneurea, hexamethylphosphoamide, etc. is allowed to be co-present as the stabilizer. As a solvent, it is preferred to use an organic solvent, in which a polar organic solvent is preferably employed. For example, an ether such as THF may be used. The reaction temperature is preferably between −80° C. and 200° C., more preferably between −50° C. and 100° C., and most preferably between −20° C. and 80° C.

In one embodiment of the present invention, electrically conductive materials are provided. The form of the conductive materials is not limited but may be a thin film. The conductive materials may contain dopants. For example, electron-accepting molecules may be introduced. In this case, for example, when the thin film is prepared by the vacuum deposition method, condensed polycyclic aromatic compound as well as the electron-accepting molecule may be supplied onto a substrate to effect thin film doping. Where the thin film is prepared by sputtering, the sputtering is performed using a binary target of the condensed polycyclic aromatic compound and the electron-accepting molecule to effect the thin film doping. Doping is effected as described above. The composition of the conductive material can be varied depending upon doping conditions. As the dopant, electron-donating molecules or electron-accepting molecules, which are used as dopants in conjugated polymers, e.g., polyacetylene, polypyrrole, polyallylenevinylene, polythienylenevinylene, etc. are preferably employed.

When the conductive material is in a thin film, a thickness of the film may be prepared in the range of 50 angstrom to the order of a micron, depending upon purpose of using the film. If necessary, protective layers for preventing dopants from spreading/scattering or for improving mechanical strength or layers of other materials may be provided on the thin film. Also, a multilayer film consisting of the thin film of the present invention and thin films of other materials may be used as functional materials by applying thin films thereto.

The conductivity of the conductive material can be assessed by the conventional direct current 2-terminal or 4-terminal method. The conductivity can be varied depending upon the kind or content of dopants according to the purpose of use. The conductivity of the conductive material of the present invention is, for example, $10^{15}$ S/cm or more.

In another aspect of the present invention, there is provided a resin composition, e.g., a blend, comprising the polyacene derivative described above and other synthetic organic polymer. For example, a resin composition comprising 1 wt % to 99 wt % of the polyacene derivative and 99 wt % to 1 wt % of a synthetic organic polymer is provided. A resin composition comprising 10 wt % to 90 wt % of the polyacene derivative and 90 wt % to 10 wt % of a synthetic organic polymer is also provided.

The synthetic organic polymer includes a thermoplastic polymer, a thermosetting polymer, engineering plastics, a conductive polymer, and the like. The synthetic organic polymer may also be a copolymer. Examples of the thermoplastic polymer include a polyolefin such as polyethylene, polypropylene, polycycloolefin, ethylene-propylene copolymer, etc., polyvinyl chloride, polyvinylidene chloride, polyvinyl acetate, polyacrylic acid, polymethacrylic acid, polystyrene, polyamide, polyester, polycarbonate, etc. Examples of the thermosetting polymer include a phenol resin, a urea resin, a melamine resin, an alkyd resin, an unsaturated polyester resin, an epoxy resin, a silicone resin, a polyurethane resin, etc. Examples of the engineering plastics include polyimide, polyphenylene oxide, polysulfone, etc. The synthetic organic polymer may be a synthetic rubber such as styrene-butadiene, etc., or a fluoro resin such as polytetrafluoroethylene, etc.

The conductive polymers include conjugated polymers such as polyacetylene, polypyrrole, polyallylenevinylene, polythienylenevinylene, etc. and those in which electron-donating molecules or electron-accepting molecules are doped. The conductive polymers further include electron donating molecules such as tetrathiafalvalene, bisethylenedithiotetrathiafulvalene, etc., or electron transfer complexes of such electron-donating molecules in combination with electron accepting molecules such as tetracyanoquinodimethane, tetracyanoethylene, etc.

The resin composition may further contain a variety of additives. Examples of the additives are a plasticizer, an antistatic agent, a colorant, a dopant, etc. Furthermore, the resin composition may also contain a reinforcing material such as glass fibers, carbon fibers, aramid fibers, boron fibers, carbon nanotubes, etc.

The resin composition described above may be prepared into the form of fibers, films or sheets, using methods known to one skilled in the art. These methods include, but are not limited thereto, melt spinning, spinning from a solution, dry jet wet spinning, extrusion, flow casting and molding techniques. The fibers, films or sheets may further be processed by roll molding, embossing, postforming or other methods known to one skilled in the art.

As the organic metal compounds shown by $L^1L^2MY^1Y^2$, for example, the following compounds may be employed.

With dihalogeno compounds such as bis(cyclopentadienyl)dichloro-zirconium, bis(methylcyclopentadienyl)dichlorozirconium, bis(butylcyclopentadienyl)dichlorozirconium, bis(indenyl)dichlorozirconium, bis(fluorenyl)dichlorozirconium, (indenyl)(fluorenyl)dichlorozirconium, bis(cyclopentadienyl)dichlorotitanium, (dimethylsilanediyl)bis(indenyl)dichlorozirconium, (dimethylsilanediyl)bis(tetrahydroindenyl)dichlorozirconium, (dimethylsilanediyl)(indenyl)dichlorozirconium, (dimethylsilanediyl)bis(2-methylindenyl)dichlorozirconium, (dimethylsilanediyl)bis (2-ethylindenyl)dichlorozirconium, (dimethylsilanediyl)bis (2-methyl-4,5-benzindenyl)dichlorozirconium, (dimethylsilanediyl)bis(2-ethyl-4,5-benzindenyl)dichlorozirconium, (dimethylsilanediyl)bis(2-methyl-4-phenylindenyl)dichlorozirconium, (dimethylsilanediyl)bis(2-ethyl-4-phenylindenyl)dichlorozirconium, (dimethylsilanediyl)bis (2-methyl-4,6-diisopropylindenyl)dichlorozirconium, it is preferred to form the metallacyclopentadienes either after reducing the dihalogeno compounds with a strong base such as an alkali metal, e.g., sodium, etc., an alkaline earth metal such as magnesium, etc. or after converting the dihalogeno compounds into the dialkyl compounds.

bis(cyclopentadienyl)dibutylzirconium;
bis(butylcyclopentadienyl)dibutylzirconium;
bis(methylcyclopentadienyl)dibutylzirconium;
bis(indenyl)dibutylzirconium;
bis(fluorenyl)dibutylzirconium;
(indenyl)(fluorenyl)dibutylzirconium;
(3-methyl-5-naphthylindenyl)(2,7-di-tert-butylfluorenyl) dibutylzirconium;
(3-methyl-5-naphthylindenyl)(3,4,7-trimethoxyfluorenyl) dibutylzirconium;
(pentamethylcyclopentadienyl)(tetrahydroindenyl)dibutylzirconium;
(cyclopentadienyl)(1-octene-8-ylcyclopentadienyl)dibutylzirconium;
(indenyl)(1-butene-4-ylcyclopentadienyl)dibutylzirconium;
[1,3-bis(trimethylsilyl)cyclopentadienyl](3,4-benzofluorenyl)dibutylzirconium;
bis(cyclopentadienyl)dibutyltitanium;
dimethylsilanediylbis(indenyl)dibutylzirconium;
dimethylsilanediylbis(tetrahydroindenyl)dibutylzirconium;
dimethylsilanediyl(cyclopentadienyl)(indenyl)dibutylzirconium;
dimethylsilanediylbis(2-methylindenyl)dibutylzirconium;
dimethylsilanediylbis(2-ethylindenyl)dibutylzirconium;
dimethylsilanediylbis(2-methyl-4,5-benzindenyl)dibutylzirconium;
dimethylsilanediylbis(2-ethyl-4,5-benzindenyl)dibutylzirconium;
dimethylsilanediylbis(4,5-dihydro-8-methyl-7H-cyclopent[e]acenaphthylene-7-ylidene)dibutylzirconium;
dimethylsilanediyl(2-methyl-4,5-benzindenyl)(2-methyl-4-phenylindenyl)dibutylzirconium;
dimethylsilanediyl(2-ethyl-4,5-benzindenyl)(2-methyl-4-phenylindenyl)dibutylzirconium;
dimethylsilanediyl(2-methyl-4,5-benzindenyl)(2-ethyl-4-phenylindenyl)dibutylzirconium;
dimethylsilanediyl(2-ethylindenyl)(2-ethyl-4-phenylnaphthyl)dibutylzirconium;
dimethylsilanediyl(2-methylindenyl)(4-phenylindenyl)dibutylzirconium;
dimethylsilanediylbis(2-methyl-4-phenylindenyl)dibutylzirconium;
dimethylsilanediylbis(2-ethyl-4-phenylindenyl)dibutylzirconium;
dimethylsilanediylbis(2-methyl-4,6-diisopropylindenyl) dibutylzirconium;
dimethylsilanediylbis(2-ethyl-4,6-diisopropylindenyl)dibutylzircomium;
dimethylsilanediylbis(2-methyl-4-naphthylindenyl)dibutylzirconium;
dimethylsilanediylbis(2-ethyl-4-naphthylindenyl)dibutylzirconium;
methylphenylsilanediylbis(indenyl)dibutylzirconium;
methylphenylsilanediyl(cyclopentadienyl)(indenyl)dibutylzirconium;
methylphenylsilanediylbis(tetrahydroindenyl)dibutylzirconium;
methylphenylsilanediylbis(2-methylindenyl)dibutylzirconium;
methylphenylsilanediylbis(2-ethylindenyl)dibutylzirconium;
methylphenylsilanediylbis(2-methyl-4,5-benzindenyl)dibutylzirconium;
methylphenylsilanediylbis(2-ethyl-4,5-benzindenyl)dibutylzirconium;
methylphenylsilanediylbis(4,5-dihydro-8-methyl-7H-cyclopent[e]acenaphthylene-7-ylidene)dibutylzirconium;
methylphenylsilanediyl(2-methyl-4,5-benzindenyl)(2-methyl-4-phenylindenyl)dibutylzirconium;
methylphenylsilanediyl(2-ethylindenyl)(2-methyl-4-phenylindenyl)dibutylzirconium;
methylphenylsilanediyl(2-methyl-4,5-benzindenyl)(2-ethyl-4-phenylindenyl)dibutylzirconium;
methylphenylsilanediyl(2-ethyl-4,5-benzindenyl)(2-ethylindenyl)dibutylzirconium;
methylphenylsilanediyl(2-methylindenyl)(4-phenylindenyl) dibutylzirconium;
methylphenylsilanediylbis(2-methyl-4-phenylindenyl)dibutylzirconium;
methylphenylsilanediylbisdibutylzirconium;
methylphenylsilanediylbis(2-methyl-4,6-diisopropylindenyl)dibutylzirconium;
methylphenylsilanediylbis(2-ethyl-4,6-diisopropylindenyl) dibutylzirconium;
methylphenylsilanediylbis(4-naphthylindenyl)dibutylzirconium;
methylphenylsilanediylbis(2-ethyl-4-naphthylindenyl)dibutylzirconium;
diphenylsilanediylbis(indenyl)dibutylzirconium;
diphenylsilanediylbis(2-methylindenyl)dibutylzirconium;
diphenylsilanediylbis(2-ethylindenyl)dibutylzirconium;
diphenylsilanediyl(cyclopentadienyl)(indenyl)dibutylzirconium;
diphenylsilanediylbis(2-methyl-4,5-benzindenyl)dibutylzirconium;
diphenylsilanediylbis(2-ethyl-4,5-benzindenyl)dibutylzirconium;
diphenylsilanediyl(2-methyl-4,5-benzindenyl)(2-methyl-4-phenylindenyl)dibutylzirconium;
diphenylsilanediyl(2-ethyl-4,5-benzindenyl)(2-methyl-4-phenylindenyl)dibutylzirconium;
dihenylsilanediyl(2-methyl-4,5-benzindenyl)(2-ethyl-4-phenylindenyl)dibutylzirconium;
diphenylsilanediyl(2-ethyl-4,5-benzindenyl)(2-ethyl-4-naphthylindenyl)dibutylzirconium;
diphenylsilanediyl(2-methylindenyl)(4-phenylindenyl)dibutylzircorium;
diphenylsilanediylbis(2-methyl-4-phenylindenyl)dibutylzirconium;
diphenylsilanediylbis(2-ethyl-4-phenylindenyl)dibutylzirconium;
diphenylsilanediylbis(2-methyl-4,6-diisopropylindenyl) dibutylzirconium;
diphenylsilanediylbis(2-ethyl-4,6-diisopropylindenyl)dibutylzirconium;
diphenylsilanediylbis(2-methyl-4-naphthylindenyl)dibutylzirconium;
diphenylsilanediylbis(2-ethyl-4-naphthylindenyl)dibutylzirconium;
1-silacyclopentane-1,1-bis(indenyl)dibutylzirconium;
1-silacyclopentane-1,1-bis(2-methylindenyl)dibutylzirconium;

1-silacyclopentane-1,1-bis(2-ethylindenyl)dibutylzirconium;
1-silacyclopentane-1,1-bis(2-methyl-4,5-benzindenyl)dibutylzirconium;
1-silacyclopentane-1,1-bis(2-ethyl-4,5-benzindenyl)dibutylzirconium;
1-silacyclopentane-1-(2-methyl-4,5-benzindenyl)-1-(2-methyl-4-phenylindenyl)dibutylzirconium;
1-silacyclopentane-1-(2-ethyl-4,5-benzindenyl)-1-(2-methyl-4-phenylindenyl)dibutylzirconium;
1-silacyclopentane-1-(2-methyl-4,5-benzindenyl)-1-(2-ethyl-4-phenylindenyl)dibutylzirconium;
1-silacyclopentane-1-(2-ethyl-4,5-benzindenyl)-1-(2-ethyl-4-naphthylindenyl)dibutylzirconium;
1-silacyclopentane-1-(2-methylindenyl)-1-(4-phenylindenyl)dibutylzirconium;
1-silacyclopentane-1,1-bis(2-methyl-4-phenylindenyl)dibutylzirconium;
1-silacyclopentane-1,1-bis(2-ethyl-4-phenylindenyl)dibutylzirconium;
1-silacyclopentane-1,1-bis(2-methyl-4,6-diisopropylindenyl)dibutylzirconium;
1-silacyclopentane-1,1-bis(2-ethyl-4,6-diisopropylindenyl)dibutylzirconium;
1-silacyclopentane-1,1-bis(2-methyl-4-naphthylindenyl)dibutylzirconium;
1-silacyclopentane-1,1-bis(2-ethyl-4-naphthylindenyl)dibutylzirconium;
ethylene-1,2-bis(indenyl)dibutylzirconium;
ethylene-1,2-bis(tetrahydroindenyl)dibutylzirconium;
ethylene-1-(cyclopentadienyl)-2-(1-indenyl)dibutylzirconium;
ethylene-1-(cyclopentadienyl)-2-(2-indenyl)dibutylzirconium;
ethylene-1-(cyclopentadienyl)-2-(2-methyl-1-indenyl)dibutylzirconium;
ethylene-1,2-bis(2-methylindenyl)dibutylzirconium;
ethylene-1,2-bis(2-ethylindenyl)dibutylzirconium;
ethylene-1,2-bis(2-methyl-4,5-benzindenyl)dibutylzirconium;
ethylene-1,2-bis(2-ethyl-4,5-benzindenyl)dibutylzirconium;
ethylene-1,2-bis(4,5-dihydro-8-methyl-7H-cyclopent[e]acenaphthylene-7-ylidene)dibutylzirconium;
ethylene-1-(2-methyl-4,5-benzindenyl)-2-(2-methyl-4-phenylindenyl)dibutylzirconium;
ethylene-1-(2-ethyl-4,5-benzindenyl)-2-(2-methyl-4-phenylindenyl)dibutylzirconium;
ethylene-1-(2-methyl-4,5-benzindenyl)-2-(2-ethyl-4-phenylindenyl)dibutylzirconium;
ethylene-1-(2-ethyl-4,5-benzindenyl)-2-(2-ethyl-4-naphthylindenyl)dibutylzirconium;
ethylene-1-(2-methylindenyl)-2-(4-phenylindenyl)dibutylzirconium;
ethylene-1,2-bis(2-methyl-4-phenylindenyl)dibutylzirconium;
ethylene-1,2-bis(2-ethyl-4-phenylindenyl)dibutylzirconium;
ethylene-1,2-bis(2-methyl-4,6-diisopropylindenyl)dibutylzirconium;
ethylene-1,2-bis(2-ethyl-4,6-diisopropylindenyl)dibutylzirconium;
ethylene-1,2-bis(2-methyl-4-naphthylindenyl)dibutylzirconium;
ethylene-1,2-bis(2-ethyl-4-naphthylindenyl)dibutylzirconium;
propylene-2,2-bis(indenyl)dibutylzirconium;
propylene-2-cyclopentadienyl-2-(1-indenyl)dibutylzirconium;
propylene-2-cyclopentadienyl-2-(4-phenyl-1-indenyl)dibutylzirconium;
propylene-2-cyclopentadienyl-2-(9-fluorenyl)dibutylzirconium;
propylene-2-cyclopentadienyl-2-(2,7-dimethoxy-9-fluorenyl)dibutylzirconium;
propylene-2-cyclopentadienyl-2-(2,7-di-tert-butyl-9-fluorenyl)dibutylzirconium;
propylene-2-cyclopentadienyl-2-(2,7-dibromo-9-fluorenyl)dibutylzirconium;
propylene-2-cyclopentadienyl-2-(2,7-diphenyl-9-fluorenyl)dibutylzirconium;
propylene-2-cyclopentadienyl-2-(2,7-dimethyl-9-fluorenyl)dibutylzirconium;
propylene-2-(3-methylcyclopentadienyl)-2-(2,7-dibutyl-9-fluorenyl)dibutylzirconium;
propylene-2-(3-tert-butylcyclopentadienyl)-2-(2,7-dibutyl-9-fluorenyl)dibutylzirconium;
propylene-2-(3-trimethylsilylcyclopentadienyl)-2-(3,6-di-tert-butyl-9-fluorenyl)dibutylzirconium;
propylene-2-cyclopentadienyl-2-[2,7-bis(3-butene-1-yl)-9-fluorenyl]dibutylzirconium;
propylene-2-cyclopentadienyl-2-(3-tert-butyl-9-fluorenyl)dibutylzirconium;
propylene-2,2-bis(tetrahydroindenyl)dibutylzirconium;
propylene-2,2-bis(2-methylindenyl)dibutylzirconium;
propylene-2,2-bis(2-ethylindenyl)dibutylzirconium;
propylene-2,2-bis(2-methyl-4,5-benzindenyl)dibutylzirconium;
propylene-2,2-bis(2-ethyl-4,5-benzindenyl)dibutylzirconium;
propylene-2,2-bis(4,5-dihydro-8-methyl-7H-cyclopent[e]acenaphthylene-7-ylidene)dibutylzirconium;
propylene-2-(2-methyl-4,5-benzindenyl)-2-(2-methyl-4-phenylindenyl)dibutylzirconium;
propylene-2-(2-ethyl-4,5-benzindenyl)-2-(2-methyl-4-phenylindenyl)dibutylzirconium;
propylene-2-(2-methyl-4,5-benzindenyl)-2-(2-ethyl-4-phenylindenyl)dibutylzirconium;
propylene-2-(2-ethyl-4,5-benzindenyl)-2-(2-ethyl-4-naphthylindenyl)dibutylzirconium;
propylene-2-(2-methylindenyl)-2-(4-phenylindenyl)dibutylzirconium;
propylene-2,2-bis(2-methyl-4-phenylindenyl)dibutylzirconium;
propylene-2,2-bis(2-ethyl-4-phenylindenyl)dibutylzirconium;
propylene-2,2-bis(2-methyl-4,6-diisopropylindenyl)dibutylzirconium;
propylene-2,2-bis(2-ethyl-4,6-diisopropylindenyl)dibutylzirconium;
propylene-2,2-bis(2-methyl-4-naphthylindenyl)dibutylzirconium;
propylene-2,2-bis(2-ethyl-4-naphthylindenyl)dibutylzirconium;
1,6-bis[methylsilylbis(2-methyl-4-phenylindenyl)dibutylzirconium]hexane;
1,6-bis[methylsilylbis(2-methyl-4,5-benzindenyl)dibutylzirconium]hexane;
1,6-bis[methylsilylbis(2-ethyl-4-phenylindenyl)dibutylzirconium]hexane;
1,6-bis[methylsilylbis(2-methyl-4-naphthylindenyl)dibutylzirconium]hexane;
1,6-bis[methylsilylbis(2-methyl-4,6-diisopropylindenyl)dibutylzirconium]hexane;
1,6-bis[methylsilyl(2-methyl-4-phenylindenyl)(4,5-benzindenyl)dibutylzirconium]hexane;

1-[methylsilylbis(tetrahydroindenyl)dibutylzirconium]-6-[ethylstannyl(cyclopentadienyl)(fluorenyl)dibutylzirconium]hexane;
1,6-disila-1,1,6,6-tetramethyl-1,6-bis[methylsilylbis(2-methyl-4-phenylindenyl)dibutylzirconium]hexane;
1,4-disila-1,4-bis[methylsilylbis(2-methyl-4-phenylindenyl)dibutylzirconium]cyclohexane;
[1,4-bis(1-indenyl)-1,1,4,4-tetramethyl-1,4-disilabutane]bis(pentamethylcyclopentadienyldibutylzirconium);
[1,4-bis(9-fluorenyl)-1,1,4,4-tetramethyl-1,4-disilabutane]bis(cyclopentadienyldibutylzirconium);
[1,4-bis(1-indenyl)-1,1,4,4-tetramethyl-1,4-disilabutane]bis(cyclopentadienyldibutylzirconium);
[1-(1-indenyl)-6-(2-phenyl-1-indenyl)-1,1,6,6-tetraethyl-1,6-disila-4-oxahexane]bis(tert-butylcyclopentadienyldibutylzirconium);
[1,10-bis(2,3-dimethyl-1-indenyl)-1,1,10,10-tetramethyl-1,10-digermadecane]bis(2-methyl-4-phenylindenyldibutylzirconium);
(1-methyl-3-tert-butylcyclopentadienyl)(1-phenyl-4-methoxy-7-chlorofluorenyl)dibutylzirconium;
(4,7-dichloroindenyl)(3,6-dimesitylfluorenyl)dibutylzirconium;
bis(2,7-di-tert-butyl-9-cyclohexylfluorenyl)dibutylzirconium;
(2,7-dimesitylfluorenyl)[2,7-bis(1-naphthyl)fluorenyl]dibutylzirconium;
dimethylsilylbis(fluorenyl)dibutylzirconium;
dibutylstannylbis(2-methylfluorenyl)dibutylzirconium; 1,1,2,2-tetraethyldisilanediyl(2-methylindenyl)(4-phenylfluorenyl)dibutylzirconium;
propylene-1-(2-indenyl)-2-(9-fluorenyl)dibutylzirconium;
1,1-dimethyl-1-silaethylenebis(fluorenyl)dibutylzirconium;
[4-(cyclopentadienyl)-4,7,7-trimethyl(tetrahydroindenyl)dibutylzirconium;
[4-(cyclopentadienyl)-4,7-dimethyl-7-phenyl(5,6-dimethyltetrahydroindenyl)dibutylzirconium;
[4-(cyclopentadienyl)-4,7-dimethyl-7-(1-naphthyl)(7-phenyltetrahydroindenyl)]dibutylzirconium;
[4-(cyclopentadienyl)-4,7-dimethyl-7-butyl(6,6-diethyltetrahydroindenyl)]dibutylzirconium;
[4-(3-tert-butylcyclopentadienyl)-4,7,7-trimethyl(tetrahydroindenyl)dibutylzirconium;
[4-(1-indenyl)-4,7,7-trimethyl(tetrahydroindenyl)]dibutylzirconium;
bis(cyclopentadienyl)dibutylhafnium;
bis(indenyl)dibutylvanadium;
bis(fluorenyl)dibutylscandium;
(indenyl)(fluorenyl)dibutylniobium;
(2-methyl-7-naphthylindenyl)(2,6-di-tert-butylfluorenyl)dibutyltitanium;
(pentamethylcyclopentadienyl)(tetrahydroindenyl)butylhaffnium bromide;
(cyclopentadienyl)(1-octene-8-ylcyclopentadienyl)dibutylhafnium;
(indenyl)(2-butene-4-ylcyclopentadienyl)dibutyltitanium;
[1,3-bis(trimethylsilyl)cyclopentadienyl](3,4-benzofluorenyl)dibutylniobium;
dimethylsilanediylbis(indenyl)dibutyltitanium;
dimethylsilanediylbis(tetrahydroindenyl)dibutylhafnium;
dimethylsilanediyl(cyclopentadienyl)(indenyl)dibutyltitanium;
dimethylsilanediylbis(2-m ethylindenyl)dibutylhafnium;
dimethylsilanediylbis(2-ethylindenyl)methylscandium;
dimethylsilanediylbis(2-butyl-4,5-benzindenyl)dibutylniobium;
dimethylsilanediylbis(2-ethyl-4,5-benzindenyl)dibutyltitanium;
dimethylsilanediylbis(4,5-dihydro-8-methyl-7H-cyclopent[e]acenaphthylene-7-ylidene)dibutyltianium;
dimethylsilanediyl(2-methyl-4,5-benzindenyl)(2-methyl-4-phenylindenyl)dibutyltitanium;
dimethylsilanediyl(2-ethyl-4,5-benzindenyl)(2-methyl-4-phenylindenyl)dibutylhafnium;
dimethylsilanediyl(2-ethyl-4,5-benzindenyl)(2-ethyl-4-phenylindenyl)methylscandium;
dimethylsilanediyl(2-ethyl-4,5-benzindenyl)(2-ethyl-4-naphthylindenyl)dibutyltitanium;
dimethylsilanediyl(2-methylindenyl)(4-phenylindenyl)dibutylhafnium;
dimethylsilanediylbis(2-methyl-4-phenylindenyl)dibutylniobium;
dimethylsilanediylbis(2-ethyl-4-phenylindenyl)dibutylvanadium;
dimethylsilanediylbis(2-methyl-4,6-diisopropylindenyl)dibutylhafnium;
dimethylsilanediylbis(2-ethyl-4,6-diisopropylindenyl)dibutylvanadium;
dimethylsilanediylbis(2-methyl-4-naphthylindenyl)butylhaffnium bromide;
dimethylsilanediylbis(2-ethyl-4-naphthylindenyl)dibutyltitanium;
methylphenylsilanediylbis(indenyl)dibutyltitanium;
methylphenylsilanediyl(cyclopentadienyl)(indenyl)hafnium;
methylphenylsilanediylbis(tetrahydroindenyl)dibutylhafnium;
methylphenylsilanediylbis(2-methylindenyl)dibutyltitanium;
methylphenylsilanediylbis(2-ethylindenyl)dibutylhafnium;
methylphenylsilanediylbis(2-methyl-4,5-benzindenyl)dibutylhafnium;
methylphenylsilanediylbis(2-ethyl-4,5-benzindenyl)dibutylvanadium;
methylphenylsilanediylbis(4,5-dihydro-8-methyl-7H-cyclopent[e]acenaphthylene-7-ylidene)dibutyltitanium;
methylphenylsilanediylbis(2-methyl-4,5-benzindenyl)(2-methyl-4-phenylindenyl)butyltitanium bromide;
methylphenylsilanediylbis(2-ethyl-4,5-benzindenyl)(2-methyl-4-phenylindenyl)dibutyltitanium;
methylphenylsilanediylbis(2-methyl-4,5-benzindenyl)(2-ethyl-4-phenylindenyl)dibutylhafnium;
methylphenylsilanediylbis(2-ethyl-4,5-benzindenyl)(2-ethyl-4-phenylindenyl)dibutylhafnium;
methylphenylsilanediyl(2-methylindenyl)(4-phenylindenyl)dibutyltitanium;
methylphenylsilanediylbis(2-methyl-4-phenylindenyl)dibutylhafnium;
methylphenylsilanediylbis(2-ethyl-4-phenylindenyl)dibutylvanadium;
methylphenylsilanediylbis(2-methyl-4,6-diisopropylindenyl)dibutyltitanium;
methylphenylsilanediylbis(2-ethyl-4,6-diisopropylindenyl)dibutylhafnium;
methylphenylsilanediylbis(2-methyl-4-naphthylindenyl)dibutylhafnium;
methylphenylsilanediylbis(2-ethyl-4-naphthylindenyl)dibutyltitanium;
diphenylsilanediylbis(indenyl)dibutyltitanium;
diphenylsilanediylbis(2-methylindenyl)dibutylhafnium;
diphenylsilanediylbis(2-ethylindenyl)dibutyltitanium;
diphenylsilanediylbis(cyclopentadienyl)(indenyl)dibutylhafnium;

diphenylsilanediylbis(2-methyl-4,5-benzindenyl)dibutyltitanium;
diphenylsilanediylbis(2-ethyl-4,5-benzindenyl)dibutylhafnium;
diphenylsilanediyl(2-methyl-4,5-benzindenyl)(2-methyl-4,5-phenylindenyl)dibutylhafnium;
diphenylsilanediyl(2-ethyl-4,5-benzindenyl)(2-methyl-4,5-phenylindenyl)dibutyltitanium;
diphenylsilanediyl(2-methyl-4,5-benzindenyl)(2-ethyl-4,5-phenylindenyl)dibutylhafnium;
diphenylsilanediyl(2-ethyl-4,5-benzindenyl)(2-ethyl-4,5-phenylindenyl)dibutyltitanium;
diphenylsilanediyl(2-methylindenyl)(4-phenylindenyl)dibutyltitanium;
diphenylsilanediylbis(2-methyl-4-phenylindenyl)dibutyltitanium;
diphenylsilanediylbis(2-ethyl-4-phenylindenyl)dibutylhafnium;
diphenylsilanediylbis(2-methyl-4,6-diisopropylindenyl)dibutylhafnium;
diphenylsilanediylbis(2-ethyl-4,6-diisopropylindenyl)dibutylhafnium;
diphenylsilanediylbis(2-methyl-4-naphthylindenyl)dibutylhafnium;
diphenylsilanediylbis(2-ethyl-4-naphthylindenyl)dibutyltitanium;
1-silacyclopentane-1,1-bis(indenyl)dibutylhafnium;
1-silacyclopentane-1,1-bis(2-methylindenyl)dibutylhafnium;
1-silacyclopentane-1,1-bis(2-ethylindenyl)dibutylhafnium;
1-silacyclopentane-1,1-bis(2-methyl-4,5-benzindenyl)dibutyltitanium;
1-silacyclopentane-1,1-bis(2-ethyl-4,5-benzindenyl)dibutylhafnium;
1-silacyclopentane-1-(2-methyl-4,5-benzindenyl)-1-(2-methyl-4-phenylindenyl)methylscandium;
1-silacyclopentane-1-(2-ethyl-4,5-benzindenyl)-1-(2-methyl-4-phenylindenyl)dibutylhafnium;
1-silacyclopentane-1-(2-methyl-4,5-benzindenyl)-1-(2-ethyl-4-phenylindenyl)dibutyltitanium;
1-silacyclopentane-1-(2-ethyl-4,5-benzindenyl)-1-(2-ethyl-4-phenylindenyl)dibutylhafnium;
1-silacyclopentane-1-(2-methylindenyl)-1-(4-phenylindenyl)dibutylhafnium;
1-silacyclopentane-1,1-bis(2-methyl-4-phenylindenyl)dibutylhafnium;
1-silacyclopentane-1,1-bis(2-ethyl-4-phenylindenyl)dibutyltitanium bromide;
1-silacyclopentane-1,1-bis(2-methyl-4,6-diisopropylindenyl)dibutyltitanium;
1-silacyclopentane-1,1-bis(2-ethyl-4,6-diisopropylindenyl)dibutyltitanium;
1-silacyclopentane-1,1-bis(2-methyl-4-naphthylindenyl)methylscandium;
1-silacyclopentane-1,1-bis(2-ethyl-4-naphthylindenyl)dibutylhafnium;
ethylene-1,2-bis(indenyl)methylscandium;
ethylene-1,2-bis(tetrahydroindenyl)dibutyltitanium;
ethylene-1-(cyclopentadienyl)-2-(1-indenyl)dibutylhafnium;
ethylene-1-(cyclopentadienyl)-2-(2-indenyl)butyltitanium bromide;
ethylene-1-(cyclopentadienyl)-2-(2-methyl-1—indenyl)dibutylhafnium;
ethylene-1,2-bis(2-methylindenyl)dibutylhafnium;
ethylene-1,2-bis(2-ethylindenyl)dibutylhafnium;
ethylene-1,2-bis(2-methyl-4,5-benzindenyl)dibutylhafnium;
ethylene-1,2-bis(2-ethyl-4,5-benzindenyl)dibutyltitanium;
ethylene-1,2-bis(4,5-dihydro-8-methyl-7H-cyclopent[e]acenaphthylene-7-ylidene)dibutyltitanium;
ethylene-1-(2-methyl-4,5-benzindenyl)-2-(2-methyl-4-phenylindenyl)dibutyltitanium;
ethylene-1-(2-ethyl-4,5-benzindenyl)-2-(2-methyl-4-phenylindenyl)dibutyltitanium;
ethylene-1-(2-methyl-4,5-benzindenyl)-2-(2-ethyl-4-phenylindenyl)methylscandium;
ethylene-1-(2-ethyl-4,5-benzindenyl)-2-(2-ethyl-4-naphthylindenyl)dibutylhafnium;
ethylene-1-(2-methylindenyl)-2-(4-phenylindenyl)dibutyltitanium;
ethylene-1,2-bis(2-methyl-4-phenylindenyl)dibutylhafnium;
ethylene-1,2-bis(2-ethyl-4-phenylindenyl)dibutylhafnium;
ethylene-1,2-bis(2-methyl-4,6-diisopropylindenyl)dibutylhafnium;
ethylene-1,2-bis(2-ethyl-4,6-diisopropylindenyl)dibutyltitanium;
ethylene-1,2-bis(2-methyl-4-naphthylindenyl)dibutyltitanium;
ethylene-1,2-bis(2-ethyl-4-naphthylindenyl)dibutylhafnium;
propylene-2,2-bis(indenyl)dibutylhafnium;
propylene-2-cyclopentadienyl-2-(1-indenyl)dibutyltitanium;
propylene-2-cyclopentadienyl-2-(4-phenyl-1-indenyl)dibutyltitanium;
propylene-2-cyclopentadienyl-2-(9-fluorenyl)dibutylhafnium;
propylene-2-cyclopentadienyl-2-(2,7-dimethoxy-9-fluorenyl)dibutylhafnium;
propylene-2-cyclopentadienyl-2-(2,7-di-tert-butyl-9-fluorenyl)dibutylhafnium;
propylene-2-cyclopentadienyl-2-(2,7-dibromo-9-fluorenyl)dibutyltitanium;
propylene-2-cyclopentadienyl-2-(2,7-diphenyl-9-fluorenyl)dibutylhafnium;
propylene-2-cyclopentadienyl-2-(2,7-dimethyl-9-fluorenyl)dibutyltitanium;
propylene-2-(3-methylcyclopentadienyl)-2-(2,7-dibutyl-9-fluorenyl)dibutylhafnium;
propylene-2-(3-tert-butylcyclopentadienyl)-2-(2,7-dibutyl-9-fluorenyl)dibutyltitanium;
propylene-2-(3-trimethylsilylcyclopentadienyl)-2-(3,6-di-tert-butyl-9-fluorenyl)dibutyltitanium;
propylene-2-cyclopentadienyl-2-[2,7-bis(3-butene-1-yl)-9-fluorenyl]dibutylhafnium;
propylene-2-cyclopentadienyl-2-(3-tert-butyl-9-fluorenyl)dibutyltitanium;
propylene-2,2-bis(tetrahydroindenyl)dibutylhafnium;
propylene-2,2-bis(2-methylindenyl)dibutylhafnium;
propylene-2,2-bis(2-ethylindenyl)dibutyltitanium;
propylene-2,2-bis(2-methyl-4,5-benzindenyl)dibutyltitanium;
propylene-2,2-bis(2-ethyl-4,5-benzindenyl)dibutylhafnium;
propylene-2,2-bis(4,5-dihydro-8-methyl-7H-cyclopent[e]acenaphthylene-7-ylidene)dibutylhafnium;
propylene-2-(2-methyl-4,5-benzindenyl)-2-(2-methyl-4-phenylindenyl)dibutylhafnium;
propylene-2-(2-ethyl-4,5-benzindenyl)-2-(2-methyl-4-phenylindenyl)dibutyltitanium;
propylene-2-(2-methyl-4,5-benzindenyl)-2-(2-ethyl-4-phenylindenyl)dibutylhafnium;
propylene-2-(2-ethyl-4,5-benzindenyl)-2-(2-ethyl-4-naphthylindenyl)dibutyltitanium;

propylene-2-(2-methylindenyl)-2-(4-phenylindenyl)dibutylhafnium;
propylene-2,2-bis(2-methyl-4-phenylindenyl)dibutyltitanium;
propylene-2,2-bis(2-ethyl-4-phenylindenyl)dibutylhafnium;
propylene-2,2-bis(2-methyl-4,6-diisopropylindenyl)dibutyltitanium;
propylene-2,2-bis(2-ethyl-4,6-diisopropylindenyl)dibutylhafnium;
propylene-2,2-bis(2-methyl-4-naphthylindenyl)dibutyltitanium;
propylene-2,2-bis(2-ethyl-4-naphthylindenyl)dibutyltitanium;
1,6-bis[methylsilylbis(2-methyl-4-phenylindenyl)dibutylhafnium]hexane;
1,6-bis[methylsilylbis(2-methyl-4,5-benzindenyl)dibutyltitanium]hexane;
1,6-bis[methylsilylbis(2-ethyl-4-phenylindenyl)dibutylhafnium]hexane;
1,6-bis[methylsilylbis(2-methyl-4-naphthylindenyl)dibutyltitanium]hexane;
1,6-bis[methylsilylbis(2-methyl-4,6-diisopropylindenyl)dibutylhafnium]hexane;
1,6-bis[methylsilyl(2-methyl-4-phenylindenyl)(4,5-benzindenyl)dibutyltitanium]hexane;
1-[methylsilylbis(tetrahydroindenyl)dibutylhafnium]-6-[ethylstannyl(cyclopentadienyl)(fluorenyl)dibutyltitanium]hexane;
1,6-disila-1,1,6,6-tetramethyl-1,6-bis[methylsiylbis(2-methyl-4-phenylindenyl)dibutylhafnium]hexane;
1,4-disila-1,4-bis[methylsilylbis(2-methyl-4-phenylindenyl)dibutylhafnium]cyclohexane;
[1,4-bis(1-indenyl)-1,1,4,4-tetramethyl-1,4-disilabutane]bis(pentamethylcyclopentadienyldibutylhafnium);
[1,4-bis(9-fluorenyl)-1,1,4,4-tetramethyl-1,4-disilabutane]bis(cyclopentadienyldibutylhafnium);
[1,4-bis(1-indenyl)-1,1,4,4-tetramethyl-1,4-disilabutane]bis(cyclopentadienyldibutyltitanium);
[1-(1-indenyl)-6-(2-phenyl-1-indenyl)-1,1,6,6-tetraethyl-1,6-disila-4-oxahexane]bis(tert-butylcyclopentadienyldibutyltitanium);
[1,10-bis(2,3-dimethyl-1-indenyl)-1,1,10,10-tetramethyl-1,10-digermadecane]bis(2-methyl-4-phenylindenyldibutylhafnium);
(1-methyl-3-tert-butylcyclopentadienyl)(1-phenyl-4-methoxy-7-chlorofluorenyl)dibutyltitanium;
(4,7-dichloroindenyl)(3,6-dimethylfluorenyl)dibutyltitanium;
bis(2,7-di-tert-butyl-9-cyclohexylfluorenyl)dibutylhafnium;
(2,7-dimesitylfluorenyl)[2,7-bis(1-naphthyl)fluorenyl]dibutylhafnium;
dimethylsilylbis(fluorenyl)dibutyltitanium;
dibutylstannylbis(2-methylfluorenyl)dibutylhafnium;
1,1,2,2-tetraethyldisilanediyl(2-methylindenyl)(4-phenylfluorenyl)dibutyltitanium;
propylene-1-(2-indenyl)-2-(9-fluorenyl)dibutylhafnium;
1,1-dimethyl-1-silaethylenebis(fluorenyl)dibutyltitanium;
[4-(cyclopentadienyl)-4,7,7-trimethyl(tetrahydroindenyl)]dibutyltitanium;
[4-(cyclopentadienyl)-4,7-dimethyl-7-phenyl(5,6-dimethyltetrahydroindenyl)]dibutylhafnium;
[4-(cyclopentadienyl)-4,7-dimethyl-7-(1-naphthyl)(7-phenyltetrahydroindenyl)]dibutyltitanium;
[4-(cyclopentadienyl)-4,7-dimethyl-7-butyl(6,6-diethyltetrahydroindenyl)]dibutylhafnium;
[4-(3-tert-butylcyclopentadienyl)-4,7,7-trimethyl(tetrahydroindenyl)]dibutylhafnium;
[4-(1-indenyl)-4,7,7-trimethyl(tetrahydroindenyl)]dibutyltitanium;
bis(indenyl)dichlorozirconium;
bis(fluorenyl)dichlorozirconium;
(indenyl)(fluorenyl)dichlorozirconium;
bis(cyclopentadienyl)dichlorotitanium;
(dimethylsilanediyl)bis(indenyl)dichlorozirconium;
(dimethylsilanediyl)bis(tetrahydroindenyl)dichlorozirconium;
(dimethylsilanediyl)(indenyl)dichlorozirconium;
(dimethylsilanediyl)bis(2-methylindenyl)dichlorozirconium;
(dimethylsilanediyl)bis(2-ethylindenyl)dichlorozirconium;
(dimethylsilanediyl)bis(2-methyl-4,5-benzindenyl)dichlorozirconium;
(dimethylsilanediyl)bis(2-ethyl-4,5-benzindenyl)dichlorozirconium;
(dimethylsilanediyl)bis(2-methyl-4-phenylindenyl)dichlorozirconium;
(dimethylsilanediyl)bis(2-ethyl-4-phenylindenyl)dichlorozirconium;
(dimethylsilanediyl)bis(2-methyl-4,6-diisopropylindenyl)dichlorozirconium;
bis(cyclopentadienyl)($\eta^4$-butadiene)zirconium;
bis(methylcyclopentadienyl)($\eta^4$-butadiene)zirconium;
bis(n-butylcyclopentadienyl)($\eta^4$-butadiene)zirconium;
bisindenyl($\eta^4$-butadiene)zirconium;
(tert-butylamido)dimethyl(tetramethyl-$\eta^5$-cyclopentadienyl)silane($\eta^4$-butadiene)zirconium;
bis(2-methylbenzindenyl)($\eta^4$-butadiene)zirconium;
dimethylsilanediylbis(2-methyl-indenyl)($\eta^4$-butadiene)zirconium;
dimethylsilanediylbisindenyl($\eta^4$-butadiene)zirconium;
dimethylsilanediylbis(2-methylindenyl)($\eta^4$-butadiene)zirconium;
dimethylsilanediyl(2-methylbenzindenyl)(2-methyl-indenyl)($\eta^4$-butadiene)zirconium;
dimethylsilanediyl(2-methylbenzindenyl)(2-methyl-4-phenylindenyl)($\eta^4$-butadiene)zirconium;
dimethylsilanediyl(2-methylindenyl)(4-phenylindenyl)($\eta^4$-butadiene)zirconium;
dimethylsilanediylbis(2-methyl-4-phenylindenyl)($\eta^4$-butadiene)zirconium;
dimethylsilanediylbis(2-methyl-4,6-diisopropylindenyl)($\eta^4$-butadiene)zirconium;
dimethylsilanediylbis(2-methyl-4-naphthylindenyl)($\eta^4$-butadiene)zirconium;
isopropylidene(cyclopentadienyl)(fluorenyl)($\eta^4$-butadiene)zirconium;
isopropylidene(cyclopentadienyl)(indenyl)($\eta^4$-butadiene)zirconium;
(4-$\eta^5$-cyclopentadienyl)-4,7,7-triethyl-($\eta^5$-4,5,6,7-tetrahydroindenyl)($\eta^4$-butadiene)zirconium;
dimethylsilanediylbis(2-methyl-indenyl)($\eta^4$-butadiene)zirconium;
dimethylsilanediylbisindenyl($\eta^4$-butadiene)zirconium;
dimethylsilanediylbis(2-methylbenzindenyl)($\eta^4$-butadiene)zirconium;
dimethylsilanediyl(2-methylbenzindenyl)(2-methyl-indenyl)($\eta^4$-butadiene)zirconium
dimethylsilanediyl(2-methylbenzindenyl)(2-methyl-4-phenylindenyl)($\eta^4$-butadiene)zirconium;
dimethylsilanediyl(2-methylindenyl)(4-phenylindenyl)($\eta^4$-butadiene)zirconium;
dimethylsilanediylbis(2-methyl-4-phenylindenyl)($\eta^4$-butadiene)zirconium;

dimethylsilanediylbis(2-methyl-4,6-diisopropylindenyl)($\eta^4$-butadiene)zirconium;
dimethylsilanediylbis(2-methylindenyl)($\eta^4$-butadiene)zirconium;
dimethylsilanediylbisindenyl($\eta^4$-butadiene)zirconium;
dimethylsilanediylbis(2-methylbenzindenyl)($\eta^4$-butadiene)zirconium;
dimethylsilanediyl(2-methylbenzindenyl)(2-methylindenyl)($\eta^4$-butadiene)zirconium;
dimethylsilanediyl(2-methylbenzindenyl)(2-methyl-4-phenylindenyl)($\eta^4$-butadiene)zirconium;
dimethylsilanediyl(2-benzindenyl)(4-phenylindenyl)($\eta^4$-butadiene)zirconium;
dimethylsilanediylbis(2-methyl-4-phenylindenyl)($\eta^4$-butadiene)zirconium;
dimethylsilanediylbis(2-methyl-4,6-diisopropylindenyl)($\eta^4$-butadiene)zirconium;
dimethylsilanediylbis(2-methyl-4-naphthylindenyl)($\eta^4$-butadiene)zirconium;
dimethylsilanediylbis(2-methylindenyl)($\eta^4$-butadiene)zirconium;
dimethylsilanediylbisindenyl($\eta^4$-butadiene)zirconium;
dimethylsilanediylbis(2-methylbenzindenyl)($\eta^4$-butadiene)zirconium;
dimethylsilanediyl(2-methylbenzindenyl)(2-methylindenyl)($\eta^4$-butadiene)zirconium;
dimethylsilanediyl(2-methylbenzindenyl)(2-methyl-4-phenylindenyl)($\eta^4$-butadiene)zirconium;
dimethylsilanediyl(2-methylbenzindenyl)(4-phenylindenyl)($\eta^4$-butadiene)zirconium;
dimethylsilanediylbis(2-methyl-4-phenylindenyl)($\eta^4$-butadiene)zirconium;
dimethylsilanediylbis(2-methyl-4,6-diisopropylindenyl)($\eta^4$-butadiene)zirconium;
dimethylsilanediylbis(2-methyl-4-naphthylindenyl)($\eta^4$-butadiene)zirconium ;
methylphenylmethylene(fluorenyl)(cyclopentadienyl)($\eta^4$-butadiene)zirconium;
diphenylmethylene(fluorenyl)(cyclopentadienyl)($\eta^4$-butadiene)zirconium;
isopropylidene(3-methylcyclopentadienyl)(fluorenyl)($\eta^4$-butadiene)zirconium;
dimethylsilanediyl(3-tert-butylcyclopentadienyl)(fluorenyl)($\eta^4$-butadiene)zirconium;
diphenylsilanediyl(3-(trimethylsilyl)cyclopentadienyl)(fluorenyl)($\eta^4$-butadiene)zirconium;
phenylmethylsilanediylbis(2-methylindenyl)($\eta^4$-butadiene)zirconium;
phenylmethylsilanediylbisindenyl($\eta^4$-butadiene)zirconium;
phenylmethylsilanediylbis(2-methyl-4,5-benzindenyl)($\eta^4$-butadiene)zirconium;
phenylmethylsilanediyl(2-methyl-4,5-benzindenyl)(2-methylindenyl)($\eta^4$-butadiene)zirconium;
phenylmethylsilanediyl(2-methyl-4,5-benzindenyl)(2-methyl-4-phenylindenyl)($\eta^4$-butadiene)zirconium;
phenylmethylsilanediyl(2-methylindenyl)(4-phenylindenyl)($\eta^4$-butadiene)zirconium;
phenylmethylsilanediylbis(2-methyl-4-phenylindenyl)($\eta^4$-butadiene)zirconium;
phenylmethylsilanediylbis(2-ethyl-4-phenylindenyl)($\eta^4$-butadiene)zirconium;
phenylmethylsilanediylbis(2-methyl-4,6-diisopropylindenyl)($\eta^4$-butadiene)zirconium
phenylmethylsilanediylbis(2-methyl-4-naphthylindenyl)($\eta^4$-butadiene)zirconium;
ethylenebis(2-methylindenyl)($\eta^4$-butadiene)zirconium;
ethylenebisindenyl($\eta^4$-butadiene)zirconium;
ethylenebis(2-methyl-4,5-benzindenyl)($\eta^4$-butadiene)zirconium;
ethylene(2-methyl-4,5-benzindenyl)(2-methyl-4-phenylindenyl)($\eta^4$-butadiene)zirconium;
ethylene(2-methylindenyl)(2-methyl-4-phenylindenyl)($\eta^4$-butadiene)zirconium;
ethylene(2-methylindenyl)(4-phenyl-indenyl)($\eta^4$-butadiene)zirconium;
ethylenebis(2-methyl-4,5-benzindenyl)($\eta^4$-butadiene)zirconium;
ethylenebis(2-methyl-4-phenylindenyl)($\eta^4$-butadiene)zirconium;
ethylenebis(2-methyl-4,6-diisopropylindenyl)($\eta^4$-butadiene)zirconium;
ethylenebis(2-methyl-4-naphthylindenyl)($\eta^4$-butadiene)zirconium;
ethylenebis(2-ethyl-4-phenylindenyl)($\eta^4$-butadiene)zirconium;
ethylenebis(2-ethyl-4,6-diisopropylindenyl)($\eta^4$-butadiene)zirconium;
ethylenebis(2-ethyl-4-naphthylindenyl)($\eta^4$-butadiene)zirconium;
dimethylsilanediylbis(2-ethyl-4-phenylindenyl)($\eta^4$-butadione)zirconium;
dimethylsilanediylbis(2,3,5-trimethylcyclopentadienyl)($\eta^4$-butadiene)zirconium;
1,6-{bis[methylsilylbis(2-methyl-4-phenylindenyl($\eta^4$-butadiene)zirconium)]hexane;
1,6-{bis[methylsilylbis(2-ethyl-4-phenylindenyl($\eta^4$-butadiene)zirconium)]hexane;
1,6-{bis[methylsilylbis(2-methyl-4-naphthylindenyl($\eta^4$-butadiene)zirconium)]hexane
1,6-{bis[methylsilylbis(2-methyl-4,5-benzindenyl($\eta^4$-butadiene)zirconium)]hexane;
1,6-{bis[methylsilyl(2-methyl-4-phenylindenyl)(2-methylindenyl)($\eta^4$-butadiene)zirconium)]hexane;
1,2-{bis[methylsilylbis(2-methyl-4-phenylindenyl($\eta^4$-butadiene)zirconium)]ethane;
1,2-{bis[methylsilylbis(2-ethyl-4-phenylindenyl($\eta^4$-butadiene)zirconium)]ethane;
1,2-{bis[methylsilylbis(2-methyl-4-naphthylindenyl($\eta^4$-butadiene)zirconium)]ethane
1,2-{bis[methylsilylbis(2-methyl-4,5-benzindenyl($\eta^4$-butadiene)zirconium)]ethane;
1,2-{bis[methylsilyl(2-methyl-4-phenylindenyl)(2-methylindenyl)($\eta^4$-butadiene)zirconium]}ethane.

EXAMPLES

Hereinafter the present invention will be described with reference to EXAMPLES but is not deemed to be limited to the following EXAMPLES.

All of the reactions were carried out under a nitrogen atmosphere. THF, diethyl ether, hexane and benzene, which were used as solvents, were distilled to dehydration in a nitrogen flow in the presence of sodium metal and benzophenone, and 1,2-dichloroethane was used after distillation with phosphorus pentoxide under nitrogen pressure. Zirconocene dichloride was purchased from Aldrich Chemical Company, Inc. and Nichia Corporation and provided for use. The other reagents were purchased from Kanto Kagaku, Tokyo Kasei Kogyo and Aldrich. $^1$H-NMR and $^{13}$C-NMR spectra were measured using Bruker ARX-400 or JEOL JNM-LA300. In the measurements, the internal standard was tetramethylsilane for $^1$H-NMR and deuterated chloroform for $^{13}$C-NMR. Gas chromatography was measured on SHIMADZU GC-14A gas chromatograph equipped with SHIMADZU CBP1-M25-025 fused silica capillary column. For recording, SHIMADZU CR6A-Chromatopac integrator was employed. When the yield was determined by GC, mesitylene and n-dodecane were used as the internal standard. As a packing material for the column chromatography, Kanto Kagaku Silica gel 60N (spherical, neutral) 40-100 micrometer was used.

Reference Example 1

Dimethyl 1,4,5,6,7,8-hexapropyl-9,10-dihydroanthracene-2,3-dicarboxylate

Bis($\eta^5$-cyclopentadienyl)dichlorozirconium (1.2 mmol) and THF (10 ml) were charged in a Schlenk tube. This solution was cooled to −78° C., and n-butyl lithium (2.4 mmols) was then added to the solution. The solution was stirred at −78° C. for an hour to give bis($\eta^5$-cyclopentadienyl)dibutylzirconium.

After 1,2-bis(2-hexynyl)-3,4,5,6-tetrapropylbenzene (1.0 mmol) was added to the reaction mixture at −78° C., the mixture was warmed to room temperature and allowed to stand for an hour to give 1-zirconacyclopenta-2,4-diene derivative.

To a solution of the thus obtained 1-zirconacyclopenta-2,4-diene (1.0 mmol) derivative in THF (10 ml), CuCl (2.0 mmols) and dimethyl acetylenedicarboxylate (3.0 mmols) were added followed by stirring at room temperature for an hour. Then, the reaction was quenched with 3N hydrochloric acid. Next, the reaction mixture was extracted with diethyl ether, and washed with sodium hydrogencarbonate aqueous solution and brine followed by drying over anhydrous magnesium sulfate. After concentrating under reduced pressure, the residue was subjected to column chromatography using silica gel as the packing material to give the title compound.

The scheme for synthesis of the title compound of EXAMPLE 1 or similar compounds starting from the title compound of REFERENCE EXAMPLE 2 or similar compounds, which were obtained by aromatizing the title compound of REFERENCE EXAMPLE 1 or similar compounds, is illustrated in FIG. 1.

Reference Example 2

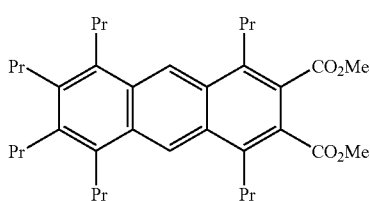

Dimethyl 1,4,5,6,7,8-hexapropylanthracene-2,3-dicarboxylate

Dimethyl 1,4,5,6,7,8-hexapropyl-9,10-dihydroanthracene-2,3-dicarboxylate obtained in REFERENCE EXAMPLE 1 was used. 2,3-Dichloro-5,6-dicyanobenzoquinone (0.729 g, 3.21 mmols) was added to a solution of dimethyl 1,4,5,6,7,8-hexapropyl-9,10-dihydroanthracene-2,3-dicarboxylate (1.554 g, 2.832 mmols) in benzene (25 ml). Subsequently, the mixture was refluxed for an hour. After filtration, the solvent in the mixture was removed in vacuum. Hexane was added to disintegrate into powders, whereby 1.393 g of the title compound was obtained as a white solid. The isolation yield was 90%.

$^1$H NMR (CDCl$_3$, Me$_4$Si) δ 1.13 (t, J=7.2 Hz, 6H), 1.14 (t, J=7.3 Hz, 6H), 1.21 (t, J=7.3 Hz, 6H), 1.60-1.66 (m, 4H), 1.76-1.91 (m, 8H), 2.80 (t, J=8.3 Hz 4H), 3.14-3.23 (m, 8H), 3.93 (s, 6H), 8.82 (s, 2H); $^{13}$C NMR (CDCl$_3$, Me$_4$Si) δ 14.77 (2C), 15.01 (2C), 15.03 (2C), 24.61 (2C), 24.74 (2C), 24.88 (2C), 31.69 (2C), 32.71 (2C), 32.81 (2C), 52.25 (2C), 121.42 (2C), 126.48 (2C), 128.81 (2C), 130.52 (2C), 133.85 (2C), 137.50 (2C), 137.90 (2C), 169.78 (2C). Elemental Analysis: Calcd. for C$_{36}$H$_{50}$: C, 79.08; H, 9.22. Found: C, 79.02; H, 9.20. High resolution mass spectrometer: Calcd. for C$_{38}$H$_{50}$O$_4$ 546.3709, Found: 546.3709.

Reference Example 3

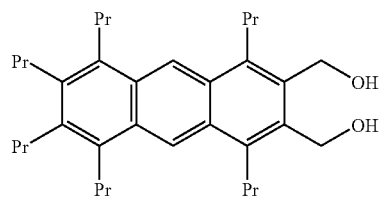

2,3-Bis(hydroxymethyl)-1,4,5,6,7,8-hexapropylanthracene

Dimethyl 1,4,5,6,7,8-hexapropylanthracene-2,3-dicarboxylate obtained in REFERENCE EXAMPLE 2 was used. After lithium aluminum hydride was added to the solution of dimethyl 1,4,5,6,7,8-hexapropylanthracene-2,3-dicarboxylate in diethyl ether at 0° C., the mixture was warmed to room temperature and stirred for an hour. At room temperature, water was added to terminate the reaction. Next, the reaction mixture was rendered slightly acidic with 2N sulfuric acid and extracted with ether. After washing with brine, the extract was dried over anhydrous magnesium sulfate. Column chromatography with silica gel as the packing material was performed using hexane. Recrystallization from hexane gave 6.637 g (13.846 mmols) of the title compound as a light yellow solid. The isolation yield was 98%.

$^1$H NMR (CDCl$_3$, Me$_4$Si) δ 1.11-1.26 (m,18H), 1.58-1.68 (m, 4H), 1.74-1.81 (m, 8H), 2.78 (t, J=8.3 Hz, 4H), 3.15 (t, J=8.3 Hz, 4H), 3.26 (t, J=8.3 Hz, 4H), 5.00 (s, 4H), 8.75 (s, 2H); $^{13}$C NMR (CDCl$_3$, Me$_4$Si) δ 14.81 (2C), 15.05 (4C), 24.56 (2C), 24.94 (2C), 25.08 (2C), 31.37 (2C), 31.75 (2C), 32.81 (2C), 60.18 (2C), 120.44 (2C), 129.30(2C), 129.74 (2C), 133.03 (2C), 133.62 (2C), 136.42 (2C), 136.85 (2C). Elemental analysis: Calcd. for C$_{34}$H$_{50}$O$_2$: C, 83.21; H, 10.27.

Found: C, 83.00; H, 10.50. High resolution mass spectrometer: Calcd. for $C_{34}H_{50}O_2$ 490.3811, Found: 490.3811.

Reference Example 4

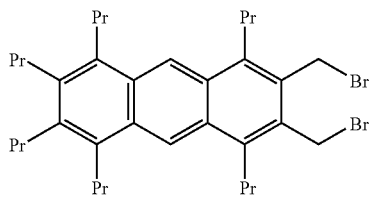

2,3-Bis(bromomethyl)-1,4,5,6,7,8-hexapropylanthracene 2,3-Bis(hydroxymethyl)-1,4,5,6,7,8-hexapropylanthracene obtained in REFERENCE EXAMPLE 3 was used. After phosphorus tribromide (1 eq.) was added to a solution of 2,3-bis(hydroxymethyl)-1,4,5,6,7,8-hexapropylanthracene (1 eq.) in chloroform at room temperature, the mixture stirred at room temperature for an hour. Next, the reaction mixture was extracted with ether. After washing with brine, the extract was dried over anhydrous magnesium sulfate. The solvent was removed and the residue was recrystallized from hexane to give 7.767 g (13.120 mmols) of the title compound as a light yellow solid. The isolation yield was 96%.

$^1$H NMR (CDCl$_3$, Me$_4$Si) δ 1.13 (t, J=7.3 Hz, 6H), 1.20 (t, J=7.2 Hz, 6H), 1.24 (t, J=7.1 Hz, 6H), 1.60-1.66 (m, 4H), 1.75-1.87 (m, 8H), 2.78 (t, J=84 Hz, 4H), 3.15 (t, J=8.3 Hz, 4H), 3.27 (t, J=8.3 Hz, 4H), 4.99 (s, 4H), 8.72 (s, 2H); $^{13}$C NMR (CDCl$_3$, Me$_4$Si) δ 14.96 (2C), 15.03 (4C), 24.38 (2C), 24.60 (2C), 24.90 (2C), 29.91(2C), 31.63 (2C), 31.72 (2C), 32.83 (2C), 120.69 (2C), 129.14 (2C), 129.17 (2C), 130.21 (2C), 133.76 (2C), 137.43 (2C), 138.69 (2C). Elemental Analysis: Calcd. for $C_{34}H_{48}Br_2$: C, 66.23; H, 7.85; Br, 25.92. Found: C, 66.35; H, 7.92; Br, 25.85.

Reference Example 5

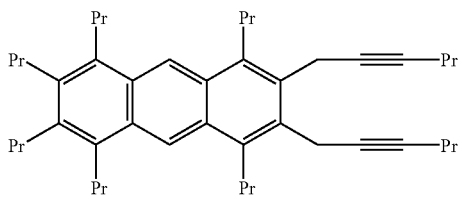

2,3-Bis(2-hexynyl)-1,4,5,6,7,8-hexapropylanthracene 2,3-Bis(bromomethyl)-1,4,5,6,7,8-hexapropylanthracene obtained in REFERENCE EXAMPLE 4 was employed. N,N'-Dimethylproyleneurea (DMPU) and 1-pentynyl lithium were added to the solution of 2,3-bis(bromomethyl)-1,4,5,6,7,8-hexapropylanthracene in THF. The reaction mixture was stirred at room temperature for an hour. The reaction was quenched with 3N Hydrochloric acid. Next, the reaction mixture was extracted with ether. After washing with sodium hydrogencarbonate aqueous solution and brine, the extract was dried over anhydrous magnesium sulfate. After the extract was concentrated under reduced pressure, column chromatography with silica gel as the packing material was performed using hexane. Recrystallization from methanol gave 6.372 g (12.338 mmols) of the title compound as a yellow solid. The isolation yield was 87%.

$^1$H NMR (CDCl$_3$, Me$_4$Si) δ 0.93 (t, J=7.4 Hz, 6H), 1.12 (t, J=7.3 Hz, 6H), 1.20 (t, J=7.3 Hz, 6H), 1.21 (t, J=7.4 Hz, 6H), 1.43-1.53 (m, 4H), 1.58-1.66 (m,4H), 1.76-1.86 (m,8H), 2.11 (tt, J=2.1, 7.0 Hz, 4H), 2.77 (t, J=8.3 Hz, 4H), 3.15 (t, J=8.2 Hz, 4H), 3.24 (t, J=8.3 Hz, 4H), 3.86 (t, J=2.1 Hz, 4H), 8.69 (s, 2H); $^{13}$C NMR (CDCl$_3$, Me$_4$Si) δ 13.47 (2C), 14.97 (2C), 15.05 (4C), 20.11 (2C), 20.95 (2C), 22.38 (2C), 24.09 (2C), 24.54 (2C), 24.96 (2C), 31.78 (2C), 31.90 (2C), 32.81 (2C), 78.57 (2C), 80.99 (2C), 119.71 (2C), 129.19 (2C), 129.31 (2C), 131.17 (2C), 133.55 (2C), 134.55 (2C), 136.20 (2C). Elemental Analysis: Calcd. for $C_{44}H_{62}$: C, 89.43; H, 10.57. Found: C, 89.17; H, 10.78.

Reference Example 6

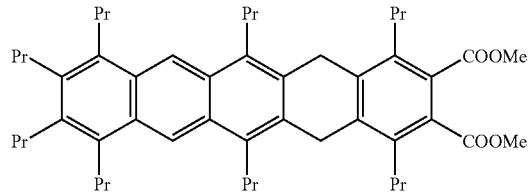

Dimethyl 5,14-dihydro-1,4,6,8,9,10,11,13-octapropylpentacene-2,3-dicarboxylate

The reaction was carried out in a manner similar to REFERENCE EXAMPLE 1. Bis(η$^5$-cyclopentadienyl)dichlorozirconium (1.2 mmol) and THF (10 ml) were charged in a Schlenk tube. This solution was cooled to −78° C., and n-butyl lithium (2.4 mmols) was then added to the solution. The solution was stirred at −78° C. for an hour to give bis(η$^5$-cyclopentadienyl)dibutylzirconium.

At −78° C., 2,3-bis(2-hexynyl)-1,4,5,6,7,8-hexapropylanthracene (1.0 mmol) obtained in REFERENCE EXAMPLE 5 was added to the reaction mixture. The mixture was then warmed to room temperature and allowed to stand for an hour to give 1-zirconacyclopenta-2,4-diene derivative.

To a solution of the thus obtained 1-zirconacyclopenta-2, 4-diene (1.0 mmol) derivative in THF (10 ml), CuCl (2.0 mmols) and dimethyl acetylenedicarboxylate (3.0 mmols) were added followed by stirring at room temperature for an hour. Then, 3N hydrochloric acid was added to terminate the reaction. Next, the reaction mixture was extracted with ether, and washed with sodium hydrogencarbonate aqueous solution and brine followed by drying over anhydrous magnesium sulfate. After concentrating under reduced pressure, the residue was subjected to short column chromatography (elute, CHCl$_3$) using silica gel. Subsequent recrystallization from a solvent mixture of chloroform and methanol gave 5.528 g (10.782 mmols) of the title compound as a cream-like solid. The isolation yield was 70%.

$^1$H NMR (CDCl$_3$, Me$_4$Si) δ 1.11 (t, J=7.2 Hz, 6H), 1.13 (t, J=7.1Hz, 6H), 1.22 (t, J=7.3 Hz, 6H), 1.23 (t, J=7.3 Hz, 6H), 1.61-1.73 (m, 8H), 1.78-1.86 (m, 8H), 2.79 (t, J=8.3 Hz, 4H), 2.84 (t, J=8.2 Hz, 4H), 3.17 (t, J=8.2 Hz, 4H), 3.32 (t, J=8.4 Hz, 4H), 3.85 (s, 6H), 4.11 (s, 4H), 8.72 (s, 2H); $^{13}$C NMR (CDCl$_3$, Me$_4$Si) δ14.66 (2C), 14.93 (2C), 15.03 (2C), 15.06

(2C), 24,31 (2C), 24.52 (2C), 24.60 (2C), 24.96 (2C), 30.39 (2C), 31.30 (2C), 31.78 (2C), 32.80 (2C), 32.89 (2C), 52.18 (2C), 119.57 (2C), 128.82 (2C), 129.17 (2C), 130.23 (2C), 131.12 (2C), 131.68 (2C), 133.50 (2C), 135.11 (2C), 136.20 (2C), 139.80 (2C), 169.48 (2C). Elemental Analysis: Calcd. for $C_{50}H_{68}O_4$: C, 81.69; H, 9.46. Found: C, 81.92; H, 9.35.

Example 1

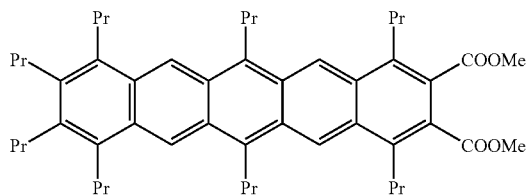

Dimethyl 1,4,6,8,9,10,11,13-octapropylpentacene-2,3-dicarboxylate

Chloranil (0.054 g, 0.22 mmol) was added to a solution of dimethyl 5,14-dihydro-1,4,6,8,9,10,11,13-octapropylpentacene-2,3-dicarboxylate (0.147 g, 0.2 mmol) obtained in REFERENCE EXAMPLE 6 in benzene (5 ml). The mixture was then refluxed for 24 hours. After concentration, chloroform was added to the residue followed by filtration. After concentration, the concentrate was recrystallized from benzene to give 0.048 g of the title compound as a blue solid. The isolation yield was 33%.

$^1$H NMR (CDCl$_3$, Me$_4$Si) δ 1.15 (t, J=7.2 Hz, 6H), 1.20 (t, J=7.3 Hz, 6H), 1.27 (t, J=7.5 Hz, 6H), 1.29 (t, J=7.4 Hz, 6H), 1.62-1.68 (m, 4H), 1.85-2.07 (m, 12H), 2.78 (t, J=7.5 Hz, 4H), 3.22-3.26 (m, 8H), 3.90 (bs, 4H), 3.94 (s, 6H), 9.06 (s, 2H), 9.17 s, H); $^{13}$C NMR (CDCl$_3$, Me$_4$Si) δ 14.85 (2C), 15.05 (2C), 15.13 (4C), 24.36 (2C), 24.60 (2C), 24.87 (2C), 25.11 (2C), 31.33 (2C), 31.76 (2C), 32.67 (2C), 32.85 (2C), 52.26 (2C), 120.08 (2C), 122.74 (2C), 126.23 (2C), 127.57 (2C), 127.76 (2C), 128.35 (2C), 129.91 (2C), 133.37 (2C), 133.76 (2C), 136.77 (2C), 138.13 (2C), 169.65 (2C). High resolution mass spectrometer: Calcd. for $C_{50}H_{66}O_4$ 730.4961, Found: 730.4995.

Figure 2:
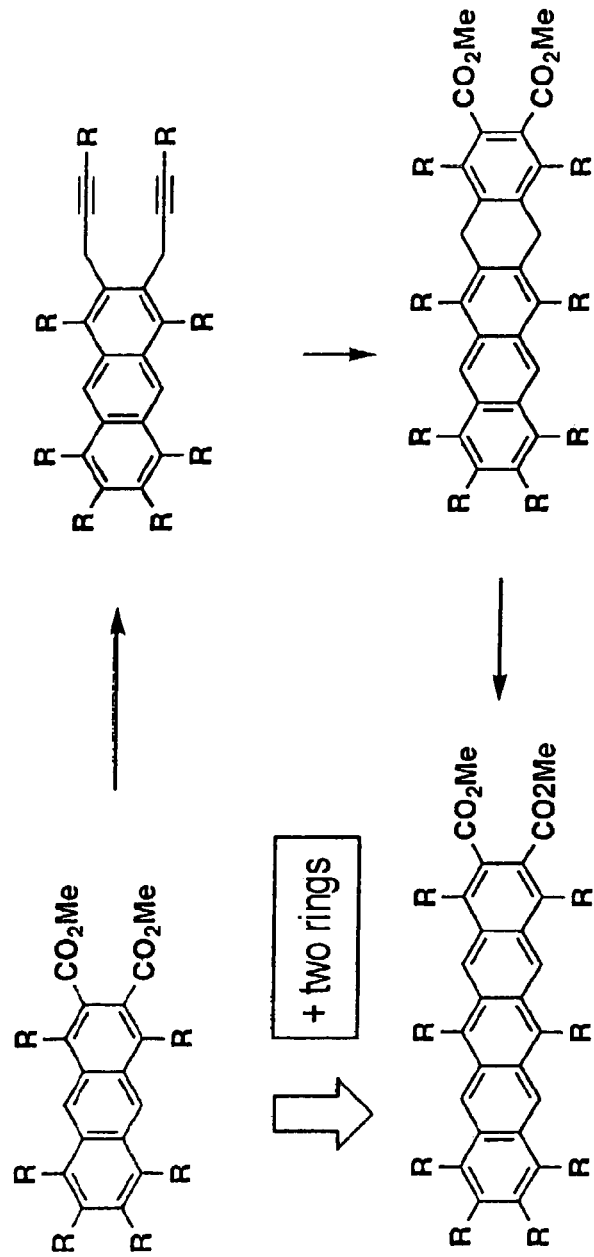
FIG. 2 illustrates an example of the synthesis scheme of polyacene derivatives in accordance with the present invention.

The scheme for synthesis of the title compound of EXAMPLE 1 starting from the title compound of REFERENCE EXAMPLE 2, and via the title compound of REFERENCE EXAMPLE 5 obtained via the title compound of REFERENCE EXAMPLE 3, then the title compound of REFERENCE EXAMPLE 4 and further via the title compound of REFERENCE EXAMPLE 6, is illustrated in FIG. 2.

Reference Example 7

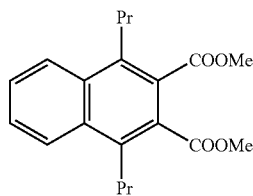

Dimethyl 1,4-dipropylnaphthalene-2,3-dicarboxylate 2,3-Dichloro-5,6-dicyanobenzoquinone (1.362 g, 6.0 mmols) was added to a solution of dimethyl 1,4-dipropyl-5,6,7,8-tetrahydronaphthalene-2,3-dicarboxylate (0.665 g, 2.0 mmols) in benzene (20 ml). The mixture was then refluxed for 24 hours. After filtration, the solvent in the mixture was removed in vacuum. By column chromatography (ethyl acetate/hexane, 1/20) using silica gel, 0.464 g of the title compound was obtained as colorless crystals. The GC yield was 87% and the isolation yield was 71%.

$^1$H NMR (CDCl$_3$, Me$_4$Si) δ 1.05 (t, J=7.4 Hz, 6H), 1.71-1.81 (m, 4H), 3.07 (t, J=8.1 Hz, 4H), 3.91 (s, 6H), 7.60 (dd, J=3.4, 6.5 Hz, 2H), 8.12 (dd, J=3.4, 6.5 Hz, 2H); $^{13}$C NMR (CDCl$_3$, Me$_4$Si) δ 14.52 (2C), 24.64 (2C), 32.20 (2C), 52.26 (2C), 125.53 (2C), 127.28 (2C), 128.25 (2C), 132.42 (2C), 136.85 (2C), 169.53 (2C), Elemental Analysis: Calcd. for $C_{20}H_{24}O_4$: C, 73.15; H, 7.37. Found: C, 73.10; H, 7.44.

Reference Example 8

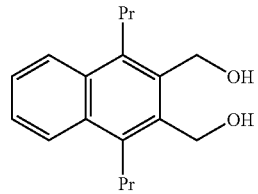

2,3-Bis(hydroxymethyl)-1,4-dipropylnaphthalene

Dimethyl 1,4-dipropylnaphthlene obtained in REFERENCE EXAMPLE 7 was treated with lithium aluminum hydride in a manner similar to REFERENCE EXAMPLE 3. Thus, 0.219 g (0.898 mmol) of the title compound was obtained as a white solid. Recrystallization from ether/hexane gave a small quantity of the title compound for elemental analysis. The isolation yield was 90%.

$^1$H NMR (CDCl$_3$, Me$_4$Si) δ(t, J=7.3 Hz, 6H), 1.59-1.67 (m,4H), 3.08 (t, J=8.2 Hz, 4H), 3.51 (bs, 2H), 4.87 (s,4H), 7.47 (dd, J=3.3, 6.5 Hz, 2H), 8.04 (dd, J=3.3, 6.5Hz, 2H); $^{13}$C NMR (CDCl$_3$, Me$_4$Si) δ 14.52 (2C), 24.96 (2C), 31.52 (2C), 59.71 (2C), 125.05 (2C), 125.77 (2C), 132.12 (2C), 134.53 (2C), 136.48 (2C). Elemental Analysis: Calcd. for $C_{18}H_{24}O_2$: C, 79.37; H, 8.88. Found: C, 79.43; H, 9.01.

Reference Example 9

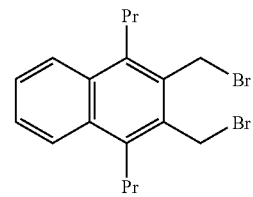

2,3-Bis(bromomethyl)-1,4-dipropylnaphthalene 2,3-Bis(hydroxymethyl)-1,4-dipropylnaphthalene obtained in REFERENCE EXAMPLE 8 was treated with phosphorus tribromide in a manner similar to REFERENCE EXAMPLE 4. By column chromatography (ethyl acetate/hexane, 1/50) using silica gel, 0.115 g (0.4 mmol) of the title compound was obtained as a white solid. The isolation yield was 72%.

$^1$H NMR (CDCl$_3$, Me$_4$Si) δ 1.14 (t, J=7.3 Hz, 6H), 1.75 (bs, 4H), 3.12 (t, J=8.3 Hz, 4H), 4.92 (s, 4H), 7.49 (dd, J=3.3, 6.5 Hz, 2H), 8.02 (dd, J=3.3, 6.5 Hz, 2H); $^{13}$C NMR (CDCl$_3$, Me$_4$Si) δ 14.77 (2C), 24.37 (2C), 29.01 (2C), 31.11 (2C), 125.17 (2C), 126.59 (2C), 130.91 (2C), 132.44 (2C), 138.44 (2C). Elemental Analysis: Calcd. for C$_{18}$H$_{22}$Br$_2$: C, 54.30; H, 5.57; Br, 40.13. Found: C, 54.21; H, 5.57; Br, 40.24.

Reference Example 10

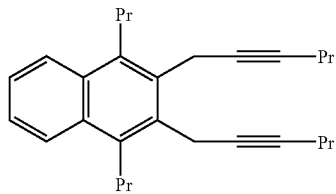

2,3-Bis(2-hexynyl)-1,4-dipropylnaphthalene 2,3-Bis(bromomethyl)-1,4-dipropylnaphthalene obtained in REFERENCE EXAMPLE 9 was treated with N,N'-dimethylpropyleneurea (DMPU) and 1-pentynyl lithium in a manner similar to REFERENCE EXAMPLE 5. By column chromatography (ethyl acetate/hexane, 1/50) using silica gel, 1.661 g (4.787 mmols) of the title compound was obtained as a white solid. The isolation yield was 93%.

$^1$H NMR (CDCl$_3$, Me$_4$Si) δ 0.91 (t, J=7.4 Hz, 6H), 1.12 (t, J=7.3 Hz, 6H), 1.40-1.49 (m, 4H), 1.68-1.78 (m, 4H), 2.07 (tt, J=2.1, 7.0 Hz, 4H), 3.10 (t, J=8.3 Hz, 4H), 3.84 (t, J=2.1 Hz, 4H), 7.41 (dd, J=3.3, 6.5 Hz, 2H), 8.01 (dd, J=3.3, 6.5 Hz, 2H); $^{13}$C NMR (CDCl$_3$, Me$_4$Si) δ 13.43 (2C), 14.77 (2C), 19.96 (2C), 20.88 (2C), 22.32 (2C), 24.11 (2C), 31.40 (2C), 78.25 (2C), 80.95 (2C), 124.64 (2C) 125.02 (2C), 131.66 (2C), 132.48 (2C), 134.99 (2C). Elemental Analysis: Calcd. for C$_{28}$H$_{36}$: C, 90.26; H, 9.74. Found: C, 90.13; H, 9.86.

Reference Example 11

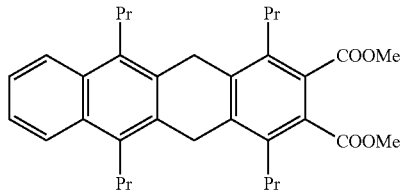

Figure 3:
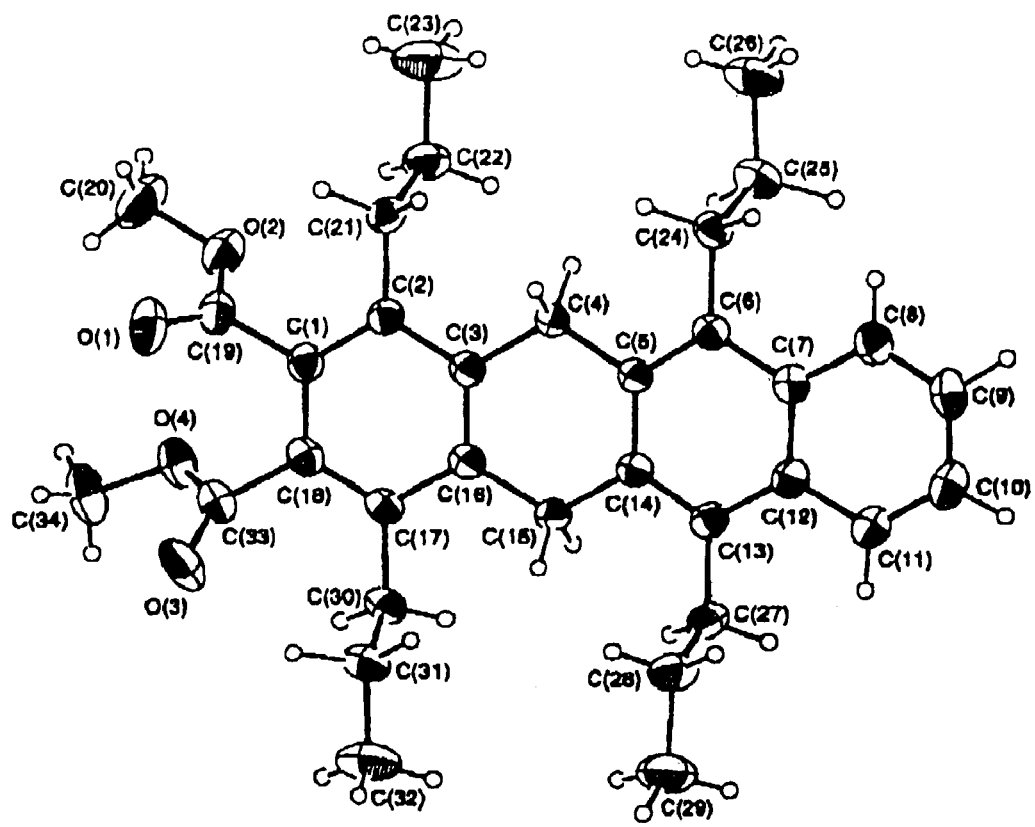
FIG. 3 shows an X-ray crystal structure analysis of dimethyl 5,12-dihydro-1,4,6,11-tetrapropylnaphthacene-2,3-dicarboxylate.
Figure 3:
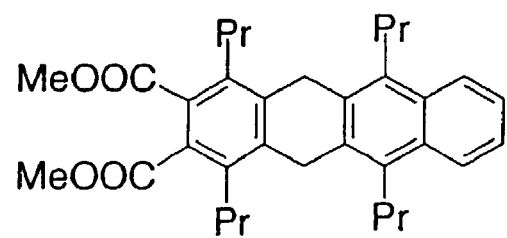

Dimethyl 5,12-dihydro-1,4,6,11-tetrapropylnaphthacene-2,3-dicarboxylate 2,3-Bis(2-hexynyl)-1,4-dipropylnaphthalene obtained in REFERENCE EXAMPLE 10 was reacted with bis(η$^5$-cyclopentadienyl)dibutylzirconium in a manner similar to REFERENCE EXAMPLE 1. Next, CuCl and dimethyl acetylenedicarboxylate were added at room temperature to the reaction mixture as it was, followed by stirring for further 1 hour at room temperature. Thereafter, 3N hydrochloric acid was added to terminate the reaction. Next, the reaction mixture was extracted with ether, and washed with sodium hydrogencarbonate aqueous is solution and brine followed by drying over anhydrous magnesium sulfate. After concentrating under reduced pressure, the residue was subjected to column chromatography (ethyl acetate/hexane, 1/10) using silica gel to give 1.790 g (4.458 mmols) of the title compound as a light yellow solid. The isolation yield was 78%. The X-ray crystal structure analysis of the title compound is shown in FIG. 3.

$^1$H NMR (CDCl$_3$, Me$_4$Si) δ 1.09 (t, J=7.3 Hz, 6H), 1.16 (t, J=7.3 Hz, 6H), 1.65-1.75 (m, 8H), 2.82 (t, J=8.2 Hz, 4H), 3.19 (t, J.=8.2 Hz, 4H), 3.84 (s, 6H), 4.08 (s, 4H), 7.45 (dd, J=3.2, 6.6 Hz, 2H), 8.06 (dd, J=3.4, 6.5 Hz, 2H); $^{13}$C NMR (CDCl$_3$, Me$_4$Si) δ 14.63 (2C), 14.76 (2C), 24.27 (2C), 24.53 (2C), 30.21 (2C), 30.85 (2C), 32.85 (2C), 52.20 (2C), 124.52 (2C), 124.86 (2C), 130.22 (2C), 131.07 (2C), 132.35 (2C), 132.39 (2C), 135.12 (2C), 139.55 (2C), 169.44 (2C). Elemental Analysis: Calcd. for C$_{34}$H$_{42}$O$_4$: C, 79.34; H, 8.22. Found: C, 79.21; H, 8.36.

Example 2

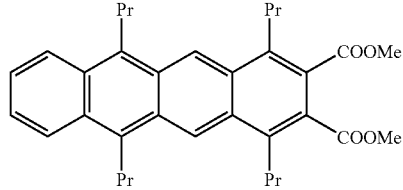

Dimethyl 1,4,6,11-tetrapropylnaphthacene-2,3-dicarboxylate

Dimethyl 5,12-dihydro-1,4,6,11-tetrapropylnaphthacene-2,3-dicarboxylate obtained in REFERENCE EXAMPLE 11 was used.

Figure 4:
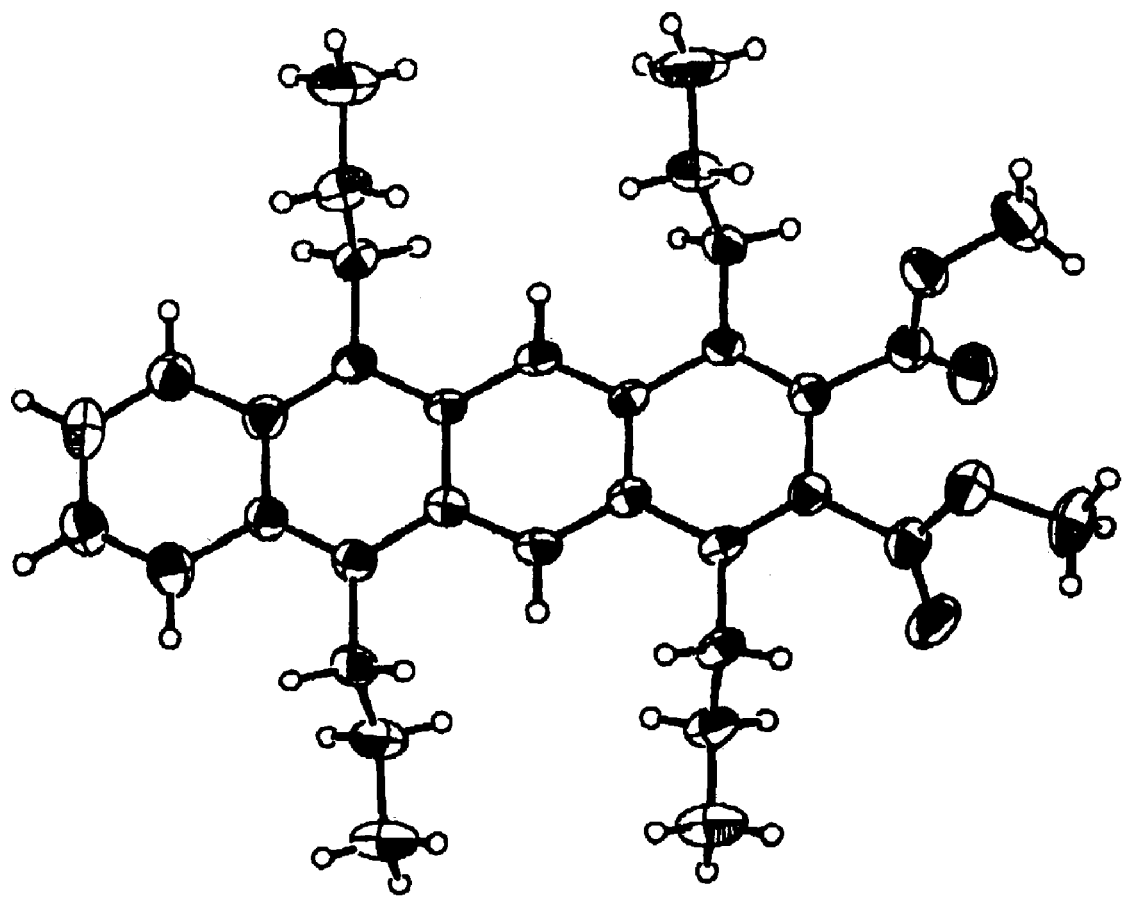
FIG. 4 shows an X-ray crystal structure analysis of dimethyl 1,4,6,11-tetrapropylnaphthacene-2,3-dicarboxylate.

2,3-Dichloro-5,6-dicyanobenzoquinone (0.050 g, 0.22 mmol) was added to a solution of dimethyl 5,12-dihydro-1,4,6,11-tetrapropylnaphthacene-2,3-dicarboxylate (0.103 g, 0.2 mmol) in 1,4-dioxane (5 ml). Subsequently, the mixture was refluxed for 3 hours. After filtration, the solvent in the mixture was removed in vacuum. Chloroform was added and the mixture was again filtered. Recrystallization from chloroform/methanol gave 0.076 g of the title compound as red needle-like crystals. The NMR yield was 97% and the isolated yield was 71%. The X-ray crystal structure analysis of the title compound is show in FIG. 4

$^1$H NMR (CDCl$_3$, Me$_4$Si) δ 1.19 (t, J=7.3 Hz, 6H), 1.23 (t, J=7.3 Hz, 6H), 1.92-1.86 (m, 8H), 3.26 (t, J=8.1 Hz, 4H), 3.72 (t, J=8.1 Hz, 4H), 3.94 (s, 6H), 7.46 (dd, J=3.2, 7.0 Hz, 2H), 8.31 (dd, J=3.2, 7.0 Hz, 2H), 9.19 (s, 2H); $^{13}$C NMR (CDCl$_3$, Me$_4$Si) δ 14.81 (2C), 14.89 (2C), 24.67 (2C), 24.89 (2C), 30.73 (2C) 32.72 (2C), 52.25 (2C), 122.65 (2C), 125.12 (2C), 125.39 (2C), 126.67 (2C), 128.44 (2C), 128.77 (2C), 129.63 (2C), 134.16 (2C), 137.87 (2C), 169.58 (2C). Elemental Analysis: Calcd. for C$_{34}$H$_{40}$O$_4$: C, 79.65; H, 7.86. Found: C, 79.43; H, 8.01. High resolution mass spectrometer: Calcd. for C$_{34}$H$_{40}$O$_4$ 512.2937, Found: 512.2937.

Figure 5:
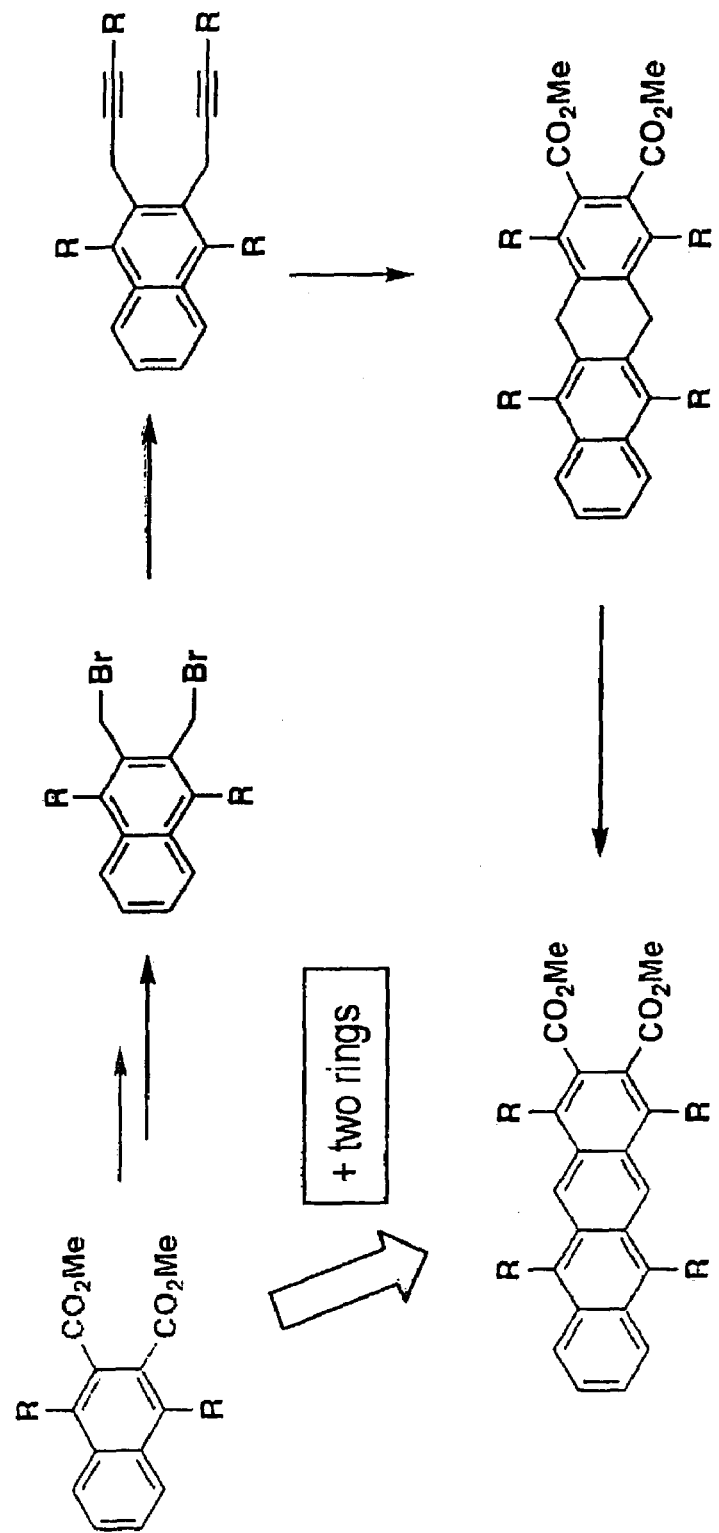
FIG. 5 illustrates an example of the synthesis scheme of polyacene derivatives in accordance with the present invention.

The scheme for synthesis of the title compound of EXAMPLE 2 starting from the title compound of REFERENCE EXAMPLE 7, and via the title compound of REFER- ENCE EXAMPLE 9 obtained via the title compound of REFERENCE EXAMPLE 8, then via the title compound of REFERENCE EXAMPLE 10 and further via the title compound of REFERENCE EXAMPLE 11, is illustrated in FIG. 5.

Reference Example 12

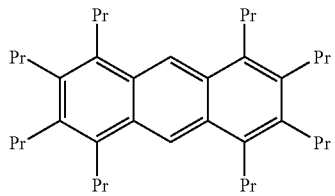

1,2,3,4,5,6,7,8-Octapropylanthracene

After 2,3-dichloro-5,6-dicyanoquinone (0.100 g, 0.440 mmol) was added to a solution of 1,2,3,4,5,6,7,8-octapropyl-9,10-dihydroanthracene (0.208 g, 0.400 mmol) in benzene (5 ml), the mixture was refluxed for an hour with heating. The reaction mixture was filtered to remove hydroquinone and purified by silica gel column chromatography (ethyl acetate/hexane, 99/1) to give the title compound (0.164 g) as a white solid. The isolation yield was 79%.

$^1$H NMR (CDCl$_3$, Me$_4$Si) δ 1.11 (t, J=7.3 Hz, 12H), 1.20 (t, J=7.3 Hz, 12H), 1.60-1.66 (m, 8H), 1.77-1.83 (m, 8H), 2.77 (t, J=7.7 Hz, 4H), 3.15 (t, J=8.2 Hz, 8H), 8.66 (s, 2H); $^{13}$C NMR (CDCl$_3$, Me$_4$Si) δ15.06 (4C), 15.09 (4C), 24.57 (4C), 25.02 (4C), 31.83 (4C), 32.83 (4C), 119.40 (2C), 129.03 (4C), 133.47 (4C), 135.80 (4C). Elemental Analysis: Calcd. for C$_{38}$H$_{58}$: C, 88.65; H, 11.35. Found: C, 88.76; H, 11.36.

2,3-Dichloro-5,6-dicyanoquinone (0.075 g, 0.440 mmol) was added to a solution of 1,2,3,4,5,6,7,8-octapropyl-9,10-dihydroanthracene (0.155 g, 0.300 mmol) in benzene (5 ml) followed by stirring at room temperature for an hour. Analysis of the reaction solution by NMR revealed that the products were 1,2,3,4,5,6,7,8-octapropylanthracene (NMR yield, 49%) and the Diels-Alder adduct (NMR yield, 30%), and 23% of the starting material remained.

Reference Example 13

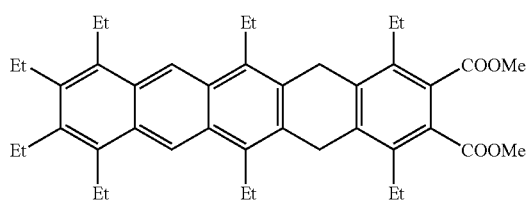

C$_{42}$H$_{52}$O$_4$ Exact Mass: 620.3866 Mol. Wt.: 620.8599 C, 81.25; H, 8.44; O, 10.31

Dimethyl 1,4,6,8,9,10,11,13-octaethyl-5,14-dihydropentacene-2,3-dicarboxylate

The title compound was obtained by the same manner as in REFERENCE EXAMPLES 2 to 6. In REFERENCE EXAMPLE 2, dimethyl 1,4,5,6,7,8-hexapropyl-9,10-dihydroanthracene-2,3-dicarboxylate was employed, whereas dimethyl 1,4,5,6,7,8-hexaethyl-9,10-dihydroanthracene-2,3-dicarboxylate was employed in REFERENCE EXAMPLE 13.

Figure 6:
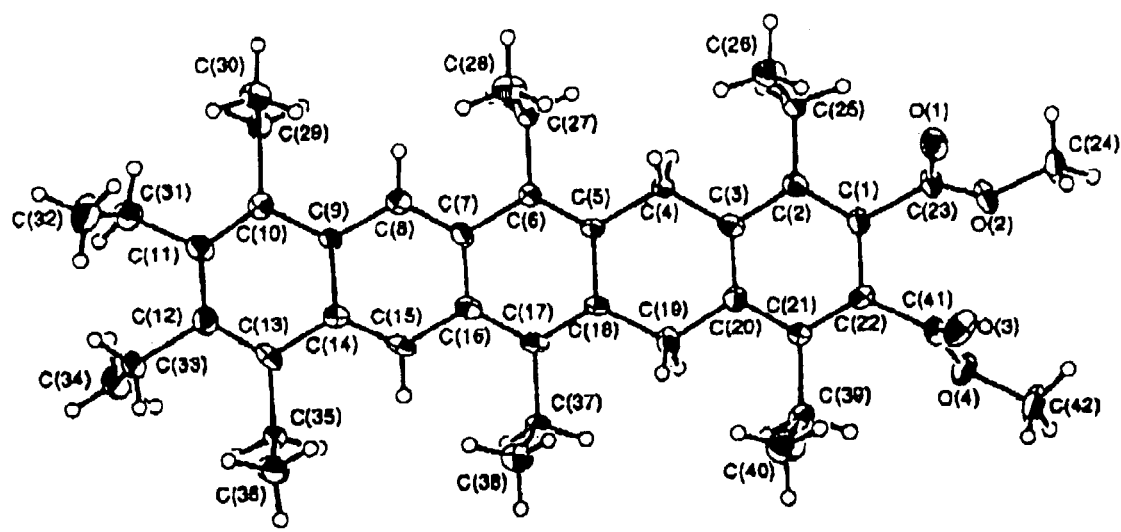
FIG. 6 shows an X-ray crystal structure analysis of dimethyl 1,4,6,8,9,10,11,13-octaethyl-5,14-dihydropentacene-2,3-dicarboxylate.
Figure 6:
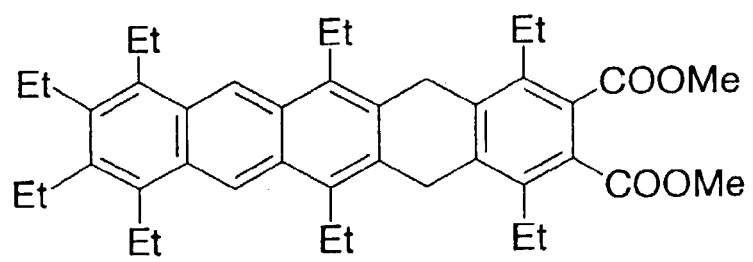

At the final step, 124 mg (0.50 mmol) of the title compound was obtained as colorless single crystals by column chromatography (Et$_2$O/hexane, 1/10) using silica gel. The isolation yield was 40%. The X-ray crystal structure analysis of the title compound is shown in FIG. 6.

$^1$H NMR (CDCl$_3$, Me$_4$Si) δ1.27-1.36 (m, 12H), 1.41-1.48 (m, 12H), 2.86-2.96 (m, 8H), 3.24-3.32 (m, 4H), 3.39-3.47 (m, 4H), 3.86 (s, 6H), 4.18 (s,4H), 8.79 (s, 2H). $^{13}$C NMR (CDCl$_3$, Me$_4$Si) δ15.22, 15.49, 15.63, 15.89, 21,87, 22.00, 22.99, 23.95, 29.95, 52.29, 119.49, 128.55, 128.99, 130.12, 130.75, 133.11. 134.78, 136.43, 137.10, 139.66, 169.53. High resolution mass spectrometer: Calcd. for C$_{42}$H$_{52}$O$_4$: 620.3866, Found: 620.3869.

Reference Example 14

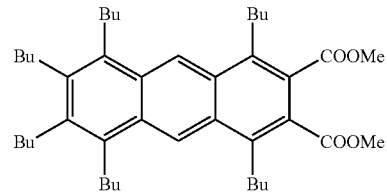

C$_{42}$H$_{62}$O$_4$ Exact Mass: 630.4648 Mol. Wt.: 630.9393 C, 79.95; H, 9.90; O, 10.14

Dimethyl 1,4,5,6,7,8-hexabutylanthracene-2,3-dicarboxylate

The reaction was carried out in a manner similar to REFERENCE EXAMPLE 2. In REFERENCE EXAMPLE 2, dimethyl 1,4,5,6,7,8-hexapropyl-9,10-dihydroanthracene-2,3-dicarboxylate was employed, whereas dimethyl 1,4,5,6,7,8-hexabutyl-9,10-dihydroanthracene-2,3-dicarboxylate was employed in REFERENCE EXAMPLE 14.

At the final step, 1764 mg (3 mmols) of the title compound was obtained as a light yellow solid by column chromatography (Et$_2$O/hexane, 1/10) using silica gel. The isolation yield was 93%.

$^1$H NMR (CDCl$_3$, Me$_4$Si) δ0.98-1.08 (m, 18H), 1.52-1.82 (m, 24H), 2.78-2.85 (m, 4H), 3.16-3.26 (m, 8H), 3.92 (s, 6H), 8.84 (s, 2H). $^{13}$C NMR (CDCl$_3$, Me$_4$Si) δ 13.94, 14.04, 14.1, 23.47, 23.59, 23.72, 29.13, 30.16, 30.39, 33.56, 33.67, 52.30, 121.40, 126.41, 128.81, 130.55, 133.91, 137.64, 137.94. High resolution mass spectrometer: Calcd. for $C_{42}H_{62}O_4$: 630.4648, Found: 630.4645.

Example 3

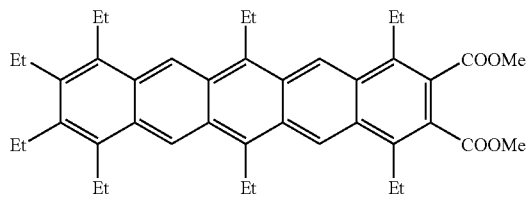

$C_{42}H_{50}O_4$ Exact Mass: 618.3709 Mol. Wt.: 618.8440 C, 81.51; H, 8.14; O, 10.34

Dimethyl 1,4,6,8,9,10,11,13-octaethylpentacene-2,3-dicarboxylate

The 1,4-dioxane solution of the compound obtained in REFERENCE EXAMPLE 13 was dehydrogenated with chloranil. By column chromatography (eluted first with $Et_2O$/hexane, 1/5 and then with 100% chloroform) using silica gel, 80 mg (0.5 mmol) of the title compound was obtained as a deep blue solid. The isolation yield was 26%.

$^1$H NMR (CDCl$_3$, Me$_4$Si) δ1.32 (t, J=7.4 Hz, 6H), 1.48-1.58 (m, 12H), 1.66 (t, J=7.5 Hz, 6H), 2.90 (q, J=7.5 Hz, 4H), 3.33 (q, J=7.5 Hz, 8H), 3.95 (s, 6H), 4.03 (q, J=7.5 Hz, 4H), 9.16 (s, 2H), 9.26 (s, 2H). $^{13}$C NMR (CDCl$_3$, Me4Si) δ 15.36, 15.66, 15.79, 15.87, 22.03, 22.21, 23.09, 23.80, 52.34, 119.92, 122.57, 126.05, 127.28, 127.47, 128.20, 129.78, 134.66, 135.20, 137.69, 139.42, 169.69. High resolution mass spectrometer: Calcd. for $C_{42}H_{50}O_4$: 618.3709, Found: 618.3680.

The foregoing results reveal that according to the process of the present invention, by introducing appropriate substituents on the condensed polycyclic is aromatic compounds to improve the solubility while the number of the rings is small, and proceeding further synthesis, the number of the polyacene rings can be increased, while maintaining the solubility.

Next, the relationship between substituents introduced and polyacene derivatives obtained was examined by way of experiments, the results of which are shown below.

Reference Example 15

1,2,3,4,5,6,7,8-Octapropylanthracene

After 2.2 equivalents of n-BuLi and 2.2 equivalents of tetramethylethylenediamine were added to the hexane solution of 9,10-dihydro-1,2,3,4,5,6,7,8-octapropylanthracene at room temperature, the mixture was heated at 50° C. for 3 hours. The reaction solution was cooled to room temperature and 1.1 equivalent of methyl iodide was added thereto. Stirring for an hour produced the title compound in the NMR yield of 98%. The compound was treated with 3N hydrochloric acid, and washed with saturated sodium hydrogencarbonate aqueous solution and brine. The organic phase was dried over anhydrous magnesium sulfate. The solvent was removed under reduced pressure to give the pure title compound in the yield of 96%. In this case, purification by column chromatography, etc. was unnecessary.

Multi-substituted dihydroanthracenes were aromatized by similar experimental procedures. The results are shown in TABLE 1.

TABLE 1

| Dihydroanthracene | Anthracene | Yield (%) |
|---|---|---|
| octapropyl-dihydroanthracene | octapropyl-anthracene | 98 (96) |
| octaethyl-dihydroanthracene | octaethyl-anthracene | 94 (90) |
| tetrapropyl-dihydroanthracene | tetrapropyl-anthracene | 96 (92) |

TABLE 1-continued

| Dihydroanthracene | Anthracene | Yield (%) |
|---|---|---|
| (structure) | (structure) | 47 (43) |

In the table above, Yield denotes the yield by NMR and the numeral within parenthesis denotes the yield when isolated.

As is evident also from TABLE 1, the system wherein the lithium dopant and the lithium-removing reagent were used in combination was extremely effective for the substituted polyhydropolyacenes, whereas the yield was 47% with the unsubstituted dihydroanthracene.

Next, various combinations of the lithium dopant and the lithium-removing reagent were examined by way of experiments, the results of which are shown in TABLE 2. In the table, the lithium dopant and the lithium-removing reagent are designated as "RM" and "R'X", respectively.

TABLE 2

| RM | R'X | Time/h | Yield/% |
|---|---|---|---|
| n-BuLi | MeI | 1 | 98 (96) |
|  | PrI | 24 | 45 (40) |
|  | BuBr | 24 | 35 (31) |
| sec-BuLi | MeI | 1 | 96 (92) |
| tert-BuLi | MeI | 1 | 95 (92) |
| MeLi | MeI | 1 | 40 (33) |
| PhLi | MeI | 1 | 91 (86) |
| EtMgBr | MeI | 1 | N.R. |

In the table, Yield denotes the yield by NMR and the numeral within parenthesis denotes the yield when isolated.

The results reveal that the yield was poor with PrI and BuBr, and good with RM/MeI. Also, n-BuLi, sec-BuLi, tert-BuLi and PhLi can be used as the lithium dopant.

The use of the lithium dopant in combination with the lithium-removing reagent provides some advantages, as compared to aromatization using Pd/C, trityl cations, n-BuLi/CdCl$_2$, or 2,3-dichloro-5,6-dicyanoquinone. When using Pd/C, high temperatures such as 200° C., 300° C., etc. are required, and with trityl cations, strong acids must be used and thus, it is likely to cause side reactions such as rearrangement reaction, etc. To the contrary, with the combination of the lithium dopant and the lithium-removing reagent, the reaction proceeds under mild conditions. When using n-BuLi/CdCl$_2$, it is essential to add toxic metal salts. In the aromatization by quinones such as 2,3-dichloro-5,6-dicyanoquinone, chloranil, etc., multi-substituted anthracenes involve the problem of causing Diels-Alder reaction as stated hereinabove to form by-products (the problem is improved by controlled reaction temperature and amount of quinones). However, the reaction of the present invention is free from such side reactions.

The combination of the lithium dopant and the lithium-removing reagent has the following characteristics. (1) No high reaction temperature is required. (2) The reaction proceeds in a short period of time and a good yield is obtained in aromatization of multi-substituted polyhydropolyacenes. (3) The product of high purity is obtained by a simple post-treatment.

Reference Example 16

The hydrocarbon condensed rings can be produced by the scheme below. The hydrocarbon condensed rings can be further aromatized to give the polyacenes.

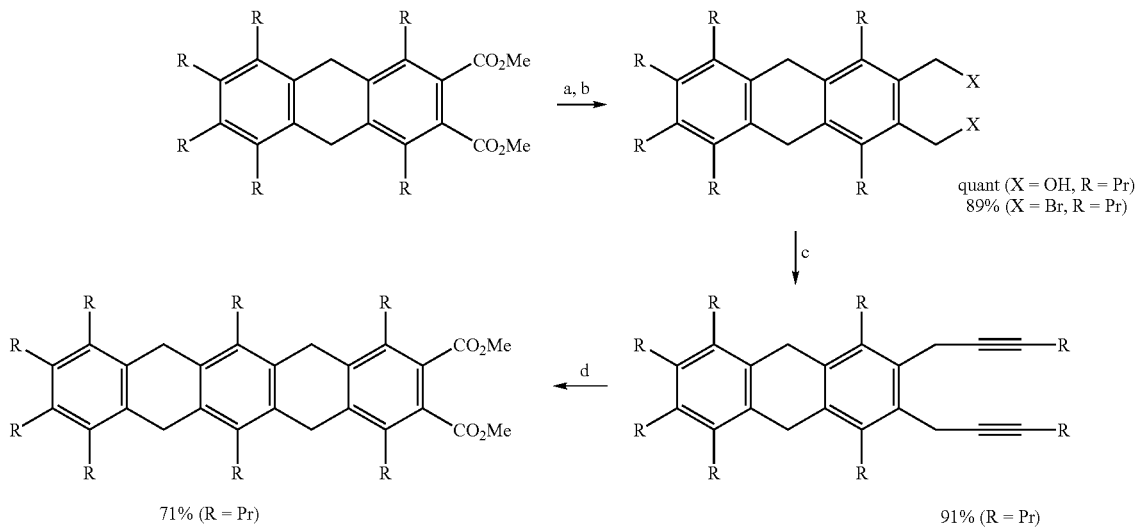

quant (X = OH, R = Pr)
89% (X = Br, R = Pr)

71% (R = Pr)

91% (R = Pr)

(wherein (a) indicates the reaction with lithium aluminum hydride at 0° C. followed by gradually elevating the temperature to room temperature; (b) indicates the reaction with phosphorus bromide at room temperature; (c) indicates the reaction with the alkynyl lithium shown by formula: R—CC—Li in THF solvent in the presence of N,N'-dimethylpropyleneurea; and (d) indicates the reaction with biscyclopentadienylzirconium dibutyl in THF solvent at −78° C. and followed by warming the system to room temperature, which is followed by reacting with dimethyl acetylenecarboxylate in the presence of CuCl).

Reference Example 17

The hydrocarbon condensed rings can be produced by the scheme below. The hydrocarbon condensed rings can be further aromatized to give the polyacenes.

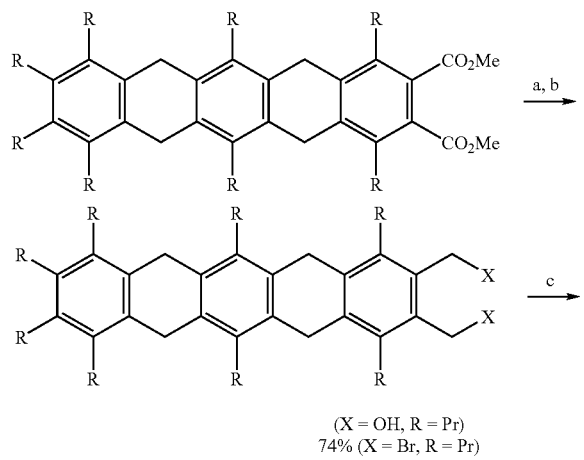

(X = OH, R = Pr)
74% (X = Br, R = Pr)

41% (R = Pr)

(wherein (a) indicates the reaction with lithium aluminum hydride at 0° C. followed by gradually elevating the temperature to room temperature; (b) indicates the reaction with phosphorus bromide at room temperature; (c) indicates the reaction with the alkynyl lithium shown by formula: R—CC—Li in THF solvent in the presence of N,N'-dimethylpropyleneurea; and (d) indicates the reaction with biscyclopentadienylzirconium dibutyl in THF solvent at −78° C. followed by warming the system to room temperature, which is followed by reacting with dimethyl acetylenecarboxylate in the presence of CuCl).

Reference Example 18

The hydrocarbon condensed rings can be produced by the scheme below. The hydrocarbon condensed rings can be further aromatized to give the polyacenes.

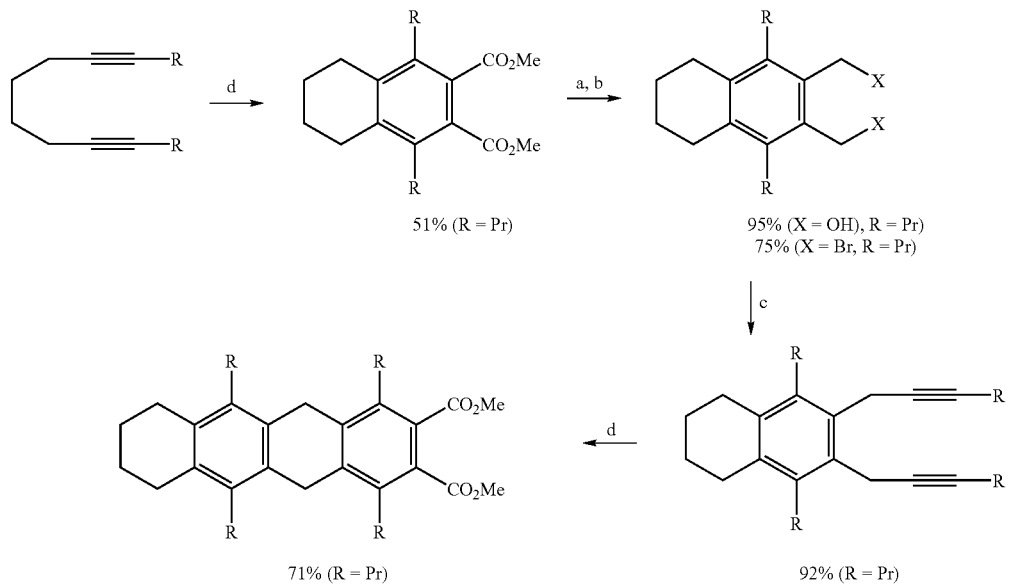

61% (R = Pr)

(wherein (a) indicates the reaction with lithium aluminum hydride at 0° C. followed by gradually elevating the temperature to room temperature; (b) indicates the reaction with phosphorus bromide at room temperature; (c) indicates the reaction with the alkynyl lithium shown by formula: R—CC—Li in THF solvent in the presence of N,N'-dimethylpropyleneurea; and (d) indicates the reaction with biscyclopentadienylzirconium dibutyl in THF solvent at −78° C. followed by warming the system to room temperature, which is followed by reacting with dimethyl acetylenecarboxylate in the presence of CUCl).

Reference Example 19

The hydrocarbon condensed rings can be produced by the scheme below. The hydrocarbon condensed rings can be further aromatized to give the polyacenes.

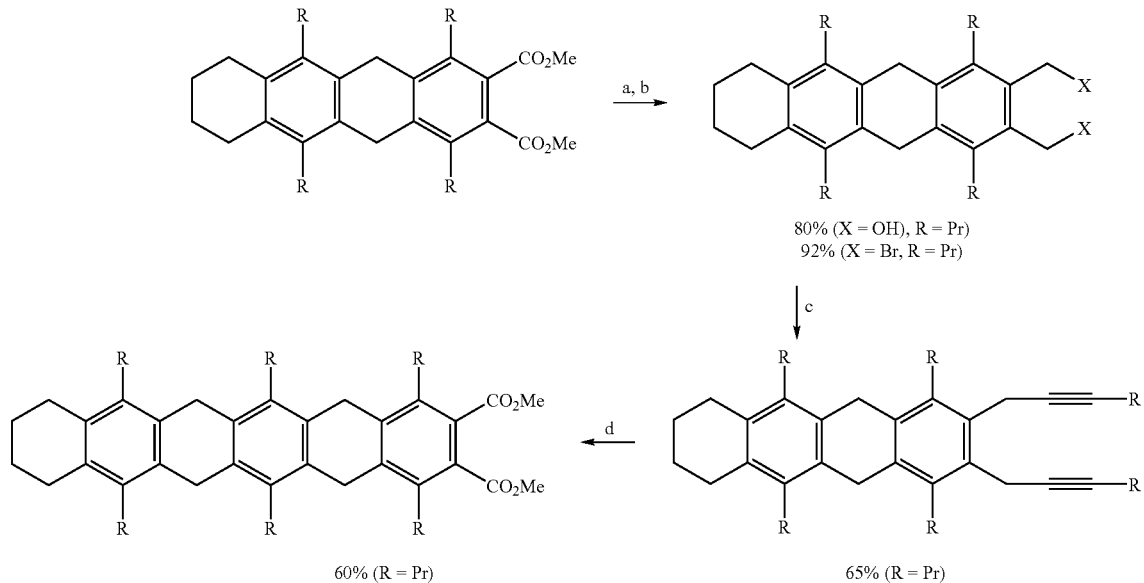

(wherein (a) indicates the reaction with lithium aluminum hydride at 0° C. followed by gradually elevating the temperature to room temperature; (b) indicates the reaction with phosphorus bromide at room temperature; (c) indicates the reaction with the alkynyl lithium shown by formula: R—CC—Li in THF solvent in the presence of N,N'-dimethylpropyleneurea; and (d) indicates the reaction with biscyclopentadienylzirconium dibutyl in THF solvent at −78° C. followed by warming the system to room temperature, Which is followed by reacting with dimethyl acetylenecarboxylate in the presence of CuCl).

Reference Example 20

The hydrocarbon condensed rings can be produced by the scheme below. The hydrocarbon condensed rings can be further aromatized to give the polyacenes.

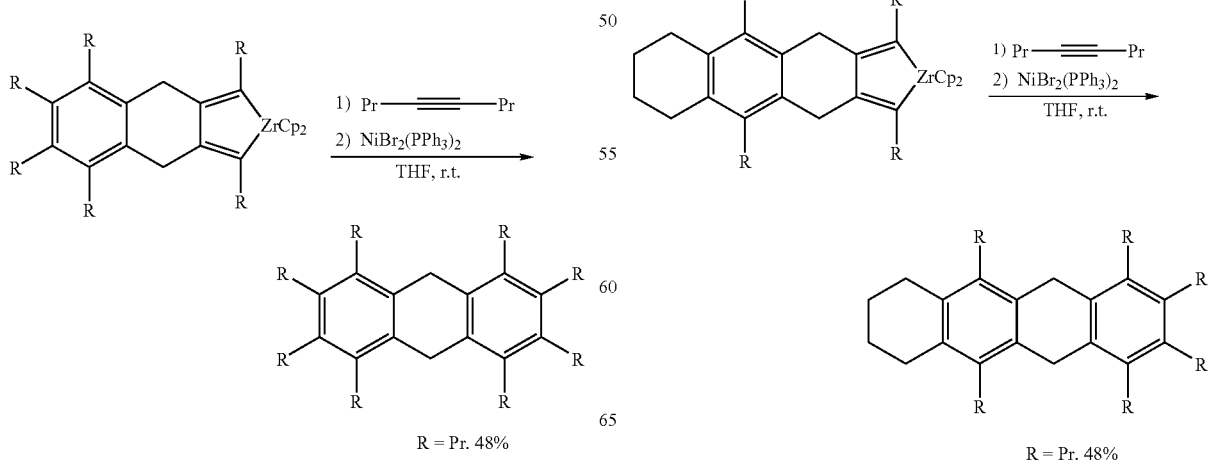

In this scheme, the following procedures were used. A solution of Cp$_2$ZrCl$_2$ (1.2 eq.) in THF was cooled to −78° C. on a dry ice-acetone bath, and a solution of n-BuLi (2.4 eq.) in hexane was added to the solution. After the reaction solution was kept at −78° C. for an hour, the alkyne was added thereto followed by elevating to room temperature. The mixture was maintained at room temperature for 1 to 3 hours thereby to form zirconacyclopentadiene. 4-Octyne (1.5 eq.) and dibromobis(triphenylphosphine)nickel (II) (2.0 eq.) were added to the THF solution of zirconacyclopentadiene (1.0 eq.) at room temperature.

After 24 hours, the mixture was treated with 3N hydrochloric acid and extracted with an appropriate solvent. The organic layers were combined in one and washed with saturated sodium hydrogencarbonate and brine followed by drying over magnesium sulfate. After the solvent was removed through an evaporator, the residue was suitably purified to give the cyclized product.

9,10-Dihydro-1,2,3,4,5,6,7,8-octapropylanthracene

Using the starting material (0.407 g, 1.00 mmol), the experiment was performed by the procedures described above. Silica gel column chromatography (ethyl acetate/hexane, 1/99) was conducted and the solid obtained was washed with ethanol to give 9,10-dihydro-1,2,3,4,5,6,7,8-octapropylanthracene as white powders (0.251 g). The isolation yield was 48%.

$^1$H NMR (CDCl$_3$, Me$_4$Si) δ1.05 (t, J=7.3 Hz, 12H), 1.12 (t, J=7.3 Hz, 12H), 1.47-1.61 (m, 16H), 2.54 (t, J=8.4 Hz, 8H), 2.70 (t, J=8.4 Hz, 8H), 3.80 (s, 4H); $^{13}$C NMR (CDCl$_3$, Me$_4$Si) δ 15.06 (4C), 15.12 (4C), 24.57 (4C), 25.10 (4C), 29.90 (2C), 32.26 (4C), 32.31 (4C), 134.33 (4C), 134.93 (4C), 136.30 (4C). Elemental Analysis: Calcd. for C$_{38}$H$_{60}$: C, 88.30; H, 11.70. Found: C, 88.45; H, 11.67.

1,2,3,4,6,8,9,10,11,13-Decapropyl-5,7,12,14-tetrahydropentacene

Using the starting material (1.19 g, 2.00 mmols), the experiment was performed by the procedures described above. By recrystallization from a solvent mixture of chloroform/methanol, 1,2,3,4,6,8,9,10,11,13-decapropyl-5,7,12,14-tetrahydropentacene was obtained as white powders (0.699 g). The isolation yield was 50%.

$^1$H NMR (CDCl$_3$, Me$_4$Si) δ 1.03-1.18 (m, 30H), 1.51-1.59 (m, 20H), 2.55 (t, J=7.8 Hz, 8H), 2.71 (t, J=7.7 Hz, 8H), 2.90 (t, J=7.7 Hz, 4H), 3.87 (s, 8H); $^{13}$C NMR (CDCl$_3$, Me$_4$Si) δ 14.98 (2C), 15.06 (4C), 15.08 (4C), 24.29 (2C), 24.54 (4C), 25.11 (4C), 29.85 (4C), 31.93 (2C), 32.22 (4C), 32.26 (4C), 133.06 (2C), 133.66 (4C), 133.95 (4C), 135.00 (4C), 136.29 (4C). Elemental Analysis: Calcd. for C$_{52}$H$_{78}$: C, 88.82; H, 11.18. Found: C, 88.92; H, 11.37.

5,7,8,9,10,12-Hexahydro-1,2,3,4,6,11-hexapropylnaphthacene

Using the starting material (0.456 g, 1.21 mmol), the experiment was performed by the procedures described above. By silica gel column chromatography (ethyl acetate/hexane, 1/99), 5,7,8,9,10,12-hexahydro-1,2,3,4,6,11-hexapropylnaphthacene was obtained as a white solid (0.283 g). The isolation yield was 48%.

$^1$H NMR (CDCl$_3$, Me$_4$Si) δ 1.04 (t, J=7.3 Hz, 6H), 1.09-1.13 (m, 12H), 1.47-1.58 (m, 12H), 1.76 (bs, 4H), 2.54 (t, J=8.2 Hz, 4H), 2.68-2.72 (m, 8H), 2.75 (bs, 4H), 3.83 (s, 4H); $^{13}$C NMR (CDCl$_3$, Me$_4$Si) δ 14.98 (2C), 15.04 (2C), 15.07 (2C), 23.31 (2C), 23.41 (2C), 24.55 (2C), 25.11 (2C), 27.31 (2C), 29.67 (2C), 31.37 (2C), 32.21 (2C), 32.26 (2C), 132.54 (2C), 133.71 (2C), 134.11 (2C), 134.93 (4C), 136.23 (2C). Elemental Analysis: Calcd. for C$_{36}$H$_{54}$: C, 88.82; H, 11.18. Found: C, 88.68; H, 11.29.

Reference Example 21

The hydrocarbon condensed rings can be produced by the scheme below. The hydrocarbon condensed rings can be further aromatized to give the polyacenes.

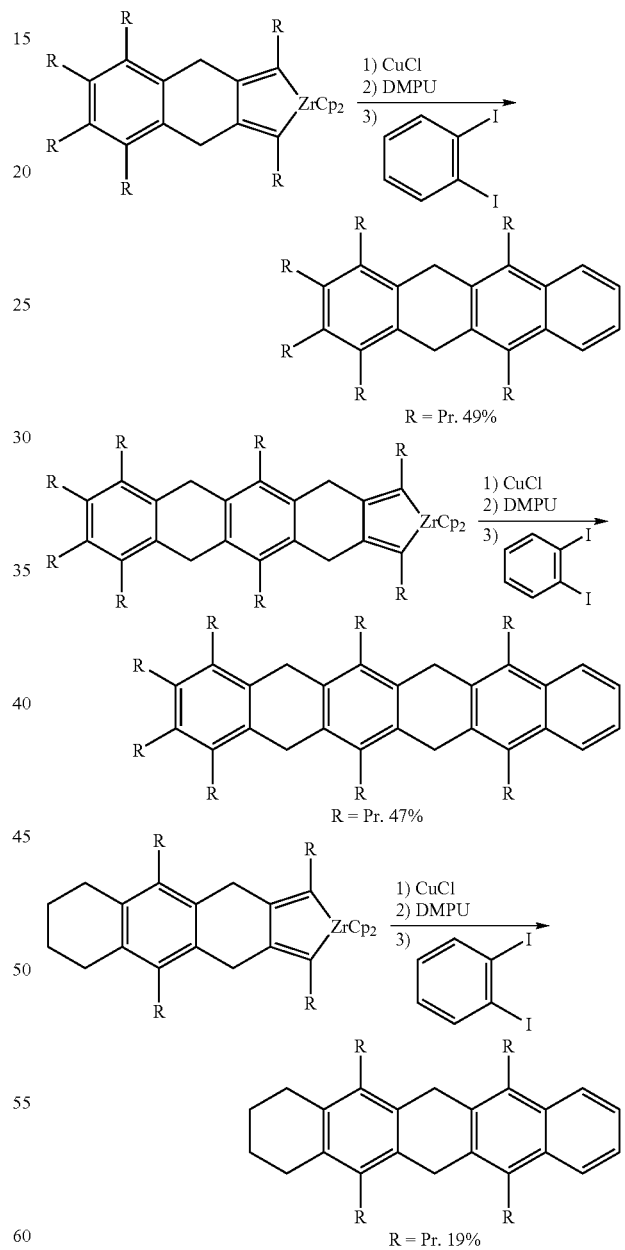

(wherein DMPU denotes N,N'-dimethylpropyleneurea.)

In this scheme, the following procedures were used. A solution of Cp$_2$ZrCl$_2$ (1.2 eq.) in THF was cooled to −78° C. on a dry ice-acetone bath, and a solution of n-BuLi (2.4 eq.) in hexane was added to the solution. After the reaction solution was kept at −78° C. for an hour, the alkyne was added thereto followed by elevating to room temperature. The mixture was maintained at room temperature for 1 to 3 hours thereby to form zirconacyclopentadiene. Copper (I) chloride (2.1 eq.), N,N'-dimethylpropyleneurea (DMPU) (3.0 eq.) and diiodobenzene (1.0 eq.) were added to a THF solution of zirconacyclopentadiene (1.0 eq.) at room temperature. After stirring at 50° C. for 24 hours, the mixture was treated with 3N hydrochloric acid. The mixture was extracted with an appropriate solvent, and the organic layers were combined in one, and then washed with saturated sodium hydrogencarbonate and brine. After drying over magnesium sulfate, the solvent was removed through an evaporator and the residue was suitably purified to give the coupling product.

5,12-Dihydro-1,2,3,4,6,11-hexapropylnaphthacene

Using the starting material (0.813 g, 2.00 mmols), the experiment was performed by the procedures described above. By silica gel column chromatography (ethyl acetate/hexane, 1/99), 5,12-dihydro-1,2,3,4,6,11-hexapropyl-naphthacene was obtained as an orange solid (0.474 g). The isolation yield was 49%.

$^1$H NMR (CDCl$_3$, Me$_4$Si) δ 1.14-1.19 (m, 18H), 1.48-1.79 (m, 12H), 2.57 (t, J=8.4 Hz, 4H), 2.76 (t, J=8.4 Hz, 4H), 3.20 (t, J=8.3 Hz, 4H), 4.04 (s, 4H) 7.42 (dd, J=3.3, 6.6 Hz, 2H), 8.05 (dd, J=3.3, 6.6 Hz, 2H); $^{13}$C NMR (CDCl$_3$, Me$_4$Si) δ14.88 (2C), 15.06 (2C), 15.10 (2C), 24.29 (2C), 24.69 (2C), 25.08 (2C), 30.42 (2C), 30.98 (2C), 32.26 (2C), 32.35 (2C), 124.47 (4C), 131.03 (2C), 131.92 (2C), 134.11 (2C), 134.26 (2C), 135.03 (2C), 136.57 (2C). High resolution mass spectrometer: Calcd. for C$_{36}$H$_{50}$ 482.3913, Found: 482.3902.

1,2,3,4,6,8,13,15-Octapropyl-5,7,14,16-tetrahydrohexene

Using the starting material (0.296 g, 0.500 mmol), the experiment was performed by the procedures described above. After hexane was added and washing was thoroughly made, the mixture was filtered. Further by washing with ethanol, 1,2,3,4,6,8,13,15-octapropyl-5,7,14,16-tetrahydrohexene of high purity was obtained as light orange powders (0.158 g). The isolation yield was 47%.

$^1$H NMR (CDCl$_3$, Me$_4$Si) δ 1.05 (t, J=7.3 Hz, 6H), 1.12-1.23 (m, 18H), 1.48-1.79 (m, 16H), 2.56 (t, J=8.3 Hz, 4H), 2.72 (t, J=8.3 Hz, 4H), 2.97 (t, J=8.3 Hz, 4H), 3.21 (t, J=8,2 Hz, 4H), 3.89 (s, 4H), 4.09 (s, 4H), 7,41 (dd, J=3.3, 6.5 Hz, 2H), 8.05 (dd, J=3.3, 6.5 Hz, 2H); $^{13}$C NMR (CDCl$_3$, Me$_4$Si) δ 14.87 (2C), 14.98 (2C), 15.08 (4C), 24.31 (2C), 24.46 (2C), 24.58 (2C), 25.12 (2C), 29.93 (2C), 30.39 (2C), 30.96 (2C), 31.97 (2C), 32.24 (2C), 32.29 (2C), 124.48 (4C), 131.03 (2C), 131.95 (2C), 133.12 (2C), 133.73 (2C), 133.94 (2C), 134.02 (2C), 134.15 (2C), 135.02 (2C), 136.36 (2C). Elemental Analysis: Calcd. for C$_{50}$H$_{68}$: C, 89.76; H, 10.24. Found: C, 89.62; H, 10.30.

1,2,3,4,6,13-Hexahydro-5,7,12,14-tetrapropylpentacene

Using the starting material (0.377 g, 1.0 mmol), the experiment was performed by the procedures described above. By silica gel column chromatography (ethyl acetate/hexane, 1/99), 1,2,3,4,6,13-hexahydro-5,7,12,14-tetrapropylpentacene was obtained as orange needle-like crystals (0.085 g). The isolation yield was 19%.

$^1$HNMR (CDCl$_3$, Me$_4$Si) δ 1.14 (t, J=7.3 Hz, 6H), 1.17 (t, J=7.5 Hz, 6H), 1.56-1.62 (m, 4H), 1.71-1.77 (m, 8H), 2.74-2.78 (m, 8H), 3.19 (t, J=8.2 Hz, 4H), 4.06 (s, 4H), 7.41 (dd, J=3.2, 6.5 Hz, 2H), 8.05 (dd, J=3.2, 6.5 Hz, 2H); $^{13}$C NMR (CDCl$_3$, Me$_4$Si) δ 14.88 (2C), 15.00 (2C), 23.27 (2C), 23.56 (2C), 24.29 (2C), 27.37 (2C), 30.19 (2C), 30.94 (2C), 31.37 (2C), 124.43 (2C), 124.49 (2C), 131.01 (2C), 131.94 (2C), 132.82 (2C), 133.59 (2C), 134.17 (2C), 135.03 (2C). High resolution mass spectrometer: Calcd. for C$_{34}$H$_{44}$ 452.3443, Found: 452.3437.

Reference Example 22

The hydrocarbon condensed rings can be produced by the scheme below. The hydrocarbon condensed rings can be further aromatized to give the polyacenes.

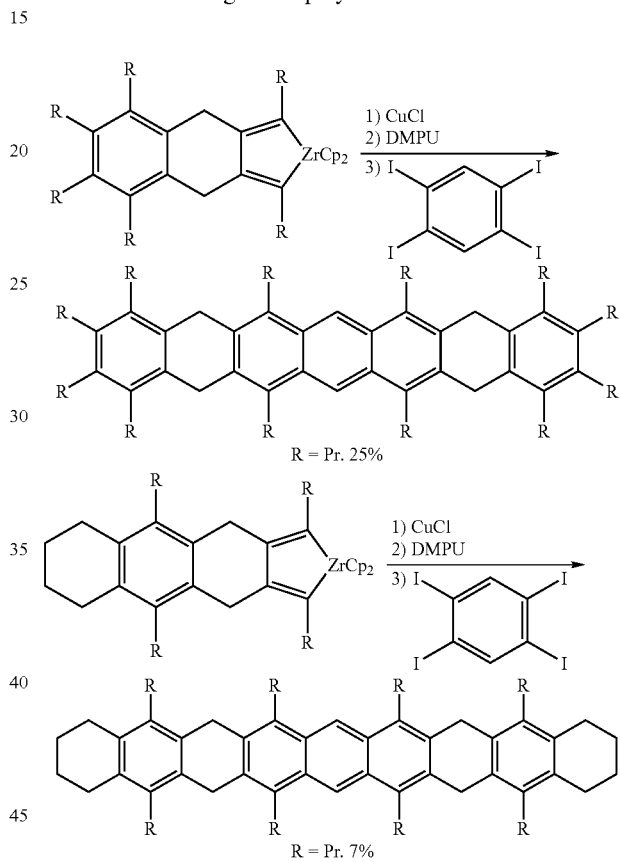

(wherein DMPU denotes N,N'-dimethylpropyleneurea).

In this scheme, the following procedures were used. A solution of Cp$_2$ZrCl$_2$ (2.4 eq.) in THF was cooled to −78° C. on a dry ice-acetone bath, and a solution of n-BuLi (4.8 eq.) in hexane was added to the solution. After the reaction solution was kept at −78° C. for an hour, the alkyne was added thereto followed by elevating to room temperature. The mixture was maintained at room temperature for 1 to 3 hours thereby to form zirconacyclopentadiene. Copper (I) chloride (4.2 eq.), N,N'-dimethylpropyleneurea (DMPU) (6.0 eq.) and tetraiodobenzene (1.0 eq.) were added to a THF solution of zirconacyclopentadiene (2.0 eq.) at room temperature. After stirring at 50° C. for 24 hours, the mixture was treated with 3N hydrochloric acid. The mixture was extracted with an appropriate solvent, and the organic layers were combined in one, and then washed with saturated sodium hydrogencarbonate and brine. After drying over magnesium sulfate, the solvent was removed through an evaporator and the residue was suitably purified to give the coupling product.

1,2,3,4,6,8,10,11,12,13,15,17-Dodecapropyl-5,9,14,18-tetrahydroheptacene

Using the starting material (0.606 g, 1.49 mmol), the experiment was performed by the procedures described above. By recrystallization from a solvent mixture of chloroform/methanol, 1,2,3,4,6,8,10,11,12,13,15,17-dodecapropyl-5,9,14,18-tetrahydroheptacene was obtained as light yellow powders (0.165 g). The isolation yield was 25%.

$^1$H NMR (CDCl$_3$, Me$_4$Si) δ 1.06 (t, J=7.2 Hz, 12H), 1.18 (t, J=7.2 Hz, 12H), 1.25 (t, J=7.3 Hz, 12H), 1.50-1.67 (m, 16H), 1.83-1.89 (m, 8H), 2.57 (t, J=8.4 Hz, 8H), 2.78 (t, J=8.3 Hz, 8H), 3.35 (t, J=7.9 Hz, 8H), 4.09 (s, 8H), 8.76 (s, 2H),; $^{13}$C NMR (CDCl$_3$, Me$_4$Si) δ 15.08 (8C), 15.11 (4C), 24.33 (4C), 24.79 (4C), 25.10 (4C), 30.62 (4C), 31.45 (4C), 32.28 (4C), 32.39 (4C), 119.50 (2C), 128.96 (4C), 131.21 (4C), 133.24 (4C), 134.34 (4C), 135.02 (4C), 136.57 (4C). Elemental Analysis: Calcd. for C$_{66}$H$_{94}$: C, 89.32; H, 10.68. Found: C, 89.03; H, 10.62.

1,2,3,4,6,10,12.13,14,15,17,21-Dodecahydro-5,7,9,11,16,18,20,22-octapropylnonacene Using the starting material (0.753 g, 2.0 mmols), the experiment was performed by the procedures described above. After ether was added and washing was thoroughly made, the mixture was filtered, and 1,2,3,4,6,8,10,11,12,13,15,17-dodecapropyl-5,9,14,18-tetrahydroheptacene of high purity was obtained as a light green solid (0.062 g). The isolation yield was 7%.

$^1$H NMR (CDCl$_3$, Me$_4$Si) δ 1.16 (t, J=7.2 Hz, 12H), 1.25 (t, J=7.2 Hz, 12H), 1.58-1.64 (m, 8H), 1.78 (bs, 8H), 1.83-1.88 (m, 8H), 2.78-2.81 (m, 16H), 3.35 (t, J=8.0 Hz, 8H), 4.11 (s, 8H), 8.76 (s, 2H); $^{13}$C NMR (CDCl$_3$, Me$_4$Si) δ 14.99 (4C), 15.05 (4C), 23.31 (4C), 23.65(4C), 24.32 (4C), 27.40 (4C), 30.40 (4C), 31.39 (4C), 119.47 (2C), 128.94 (4C), 131.22 (4C), 132.84 (4C), 133.16 (4C), 133.82 (4C), 135.00 (4C). High resolution mass spectrometer: Calcd. for C$_{62}$H$_{82}$ 826.6412, Found: 826.6389.

In the scheme described above, 2 equivalents of zirconacyclopenta[b]tetrahydronaphthalene or 2 equivalents of zirconacylopenta[b]hexahydroanthracene and 1 equivalent of 1,2,4,5-tetraiodobenzene undergo coupling reaction. The ratio of these reactants can be changed, and the coupling between 1 equivalent of zirconacyclopenta[b]tetrahydronaphthalene or 1 equivalent of zirconacylopenta[b]hexahydroanthracene and 1 equivalent of 1,2,4,5-tetraiodobenzene can provide the hydrocarbon condensed rings with iodine at the ortho-position of the terminal 6-membered ring. Alternatively, 2,3,6,7-tetraiodonaphthalene, 2,3,6,7-tetraiodoanthracene, 2,3,8,9-tetraiodotetracene, etc. may be used, in place of 1,2,4,5-tetraiodobenzene. These hydrocarbon condensed rings can be further aromatized to give polyacenes.

Reference Example 23

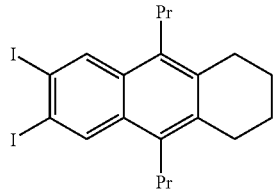

9,10-Dipropyl-2,3-diiodo-5,6,7,8-tetrahydroanthracene

To a solution of bis(η$^5$-cyclopentadienyl)dichlorozirconium (0.175 g, 0.6 mmol) in THF (25 ml), n-butyl lithium (0.75 ml, 1.2 mmol, 1.6 mol/l) was added at −78° C. After stirring the solution for an hour, 4,10-tetradodecadiyne (0.095 ml, 0.5 mmol) was added to the solution. A cooling bath was withdrawn, and the mixture was stirred for an hour. Tetraiodobenzene (0.582 g, 1.0 mmol), DMPU (0.18 ml, 1.5 mmol) and CuCl (0.104 g, 1.1 mmol) were added to the mixture. After stirring at 50° C. for an hour, 3N hydrochloric acid was added to terminate the reaction. Next, the mixture was extracted with ether followed by washing with sodium hydrogencarbonate aqueous solution and brine. After concentrating under reduced pressure, the residue was subjected to column chromatography using silica gel as the packing material to give the title compound (0.148 g) as a colorless solid. The isolation yield was 57%.

$^1$H NMR (CDCl$_3$, Me$_4$Si) δ 1.07 (t, J=7.4 Hz, 6H), 1.51-1.63 (m, 4H), 1.79-1.83 (m, 4H), 2.83-2.89 (m, 8H), 8.47 (s, 2H); $^{13}$C NMR (CDCl$_3$, Me$_4$Si) δ14.68 (2C), 22.80 (2C), 23.36 (2C), 27.81 (2C), 29.86 (2C), 102.38 (2C), 131.58 (2C), 132.88 (2C), 135.16 (2C), 135.29 (2C). High resolution mass spectrometer: Calcd. for C$_{20}$H$_{24}$I$_2$ 517.9968, Found: 517.9963.

Reference Example 24

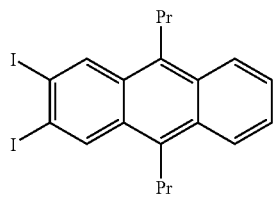

9,10-Dipropyl-2,3-diiodoanthracene 9,10-Dipropyl-2,3-diiodo-5,6,7,8-tetrahydroanthracene (0.259 g, 0.5 mmol), 2,3-dichloro-5,6-dicyanobenzoquinone (0.341 g, 1.5 mmol) and 1,4-dioxane (3 ml) were charged in a reactor. Then, the mixture was refluxed for an hour. After cooling, the precipitates were removed by filtration. The solvent in the mixture was removed in vacuum. Column chromatography (hexane) was performed to give the title compound (0.109 g) as a light yellow solid. The isolation yield was 42%.

$^1$H NMR (CDCl$_3$, Me$_4$Si) δ 1.12 (t, J=7.4 Hz, 6H), 1.73-1.85 (m,4H), 3.41 (t, J=8.1 Hz, 6H), 7.50 (dd, J=7.1, 6,6 Hz, 2H), 8.23 (dd, J=7.1, 6.6 Hz, 2H), 8.79 (s, 2H); $^{13}$C NMR (CDCl$_3$, Me$_4$Si) δ 14.67 (2C), 24.65 (2C), 29.87 (2C), 103.11 (2C), 125.33 (2C), 125.69 (2C), 129.72 (2C), 130.08 (2C), 133.19 (2C), 136.19 (2C).

High resolution mass spectrometer: Calcd. for C$_{20}$H$_{20}$I$_2$: 513.9655, Found: 513.9664.

Example 4

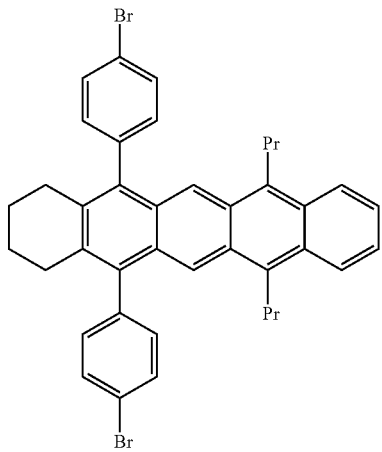

5,14-Bis(p-bromophenyl)-7,12-dipropyl-1,2,3,4-tetrahydropentacene 1,8-Bis(p-bromophenyl)-1,7-octadiyne (0.191 g, 0.459 mmol) was added at −78° C. to a THF solution of bis(η$^5$-cyclopentadienyl)dibutylzirconium in THF, which was prepared from bis(η$^5$-cyclopentadienyl)dichlorozirconium (0.161 g, 0.551 mmol) and n-butyl lithium (0.7 ml, 1.6 M, 1.1 mol/l). The mixture was then allowed to stand at room temperature for an hour. CuCl (0.095 g, 0.964 mmol), DMPU (0.17 ml, 1.38 mmol) and 2,3-diiodo-9,10-dipropylanthracene (0.236 g, 0.459 mmol) were added to the mixture. After heating at 50° C. for an hour, the solvent in the mixture was removed in vacuum. Column chromatography (chloroform) was performed. By recrystallization in chloroform/methanol, the title compound (0.177 g) was obtained as orange red. The isolation yield was 57%.

$^1$H NMR (CDCl$_3$, Me$_4$Si) δ 0.93 (t, J=7.2 Hz, 6H), 1.60-1.76 (m, 8H), 2.72 (bs, 4H), 3.33 (t, J=8.0 Hz, 4H), 7.29-7.35 (m, 6H), 7.74 (d, J=8.1 Hz, 4H), 8.18 (dd, J=6.9, 3.3 Hz, 2H), 8.27 (s, 2H); $^{13}$C NMR (CDCl$_3$, Me$_4$Si) δ 14.51 (2C), 22.83 (2C), 24.45 (2C), 29.30 (2C), 30.52 (2C), 121.23 (2C), 122.16 (2C), 124.34 (2C), 125.27 (2C), 127.70 (2C), 128.67 (2C), 129.78 (2C), 131.83 (4C), 132.13 (4C), 133.26 (2C), 133.66 (2C), 135.74 (2C), 139.04 (2C).

Reference Example 25

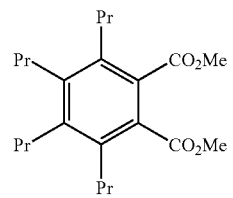

Dimethyl 3,4,5,6-tetrapropylphthalate

4-Octyne (5.9 ml, 40.0 mmols) was added at −78° C. to a 70 ml THF solution of bis(η$^5$-cyclopentadienyl)dibutylzirconium, which was prepared from bis(η$^5$-cyclopentadienyl)dichlorozirconium (7.016 g, 24.0 mmols) and n-butyl lithium (31.6 ml, 48.0 mmols, 1.52 M). After elevating to room temperature, the reaction mixture was stirred for an hour. DMAD (dimethyl acetylenedicarboxylate) (7.4 ml, 60.0 mmols) and CuCl (3.96 g, 40.0 mmols) were added to the reaction mixture at room temperature. After stirring for an hour, 3N HCl was added for hydrolysis and the mixture was extracted with hexane. Then, the extract was washed with sodium hydrogencarbonate aqueous solution and brine. After the extract was dried over anhydrous magnesium sulfate, column chromatography was performed using silica gel as the packing material to give the title compound (4.917 g) as light yellow oil. The GC yield was 82% and the isolation yield was 74%.

$^1$H NMR (CDCl$_3$, Me$_4$Si) δ 0.97 (t, J=7.2 Hz, 6H), 1.04 (t, J=7.3 Hz, 6H), 1.45-1.57 (m, 8H), 2.56-2.62 (m, 8H), 3.83(s, 6H); $^{13}$C NMR (CDCl$_3$, Me$_4$Si), δ 1468 (2C), 14.86 (2C), 24.60 (2C), 24.99 (2C), 31.70 (2C), 32.59 (2C), 52.06 (2C), 130.34 (2C), 136.84 (2C), 142.11 (2C), 169.73 (2C).

Reference Example 26

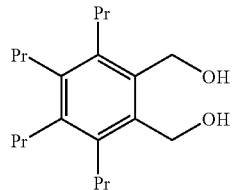

1,2-Bis(hydroxymethyl)-3,4,5,6-tetrapropylbenzene

Dimethyl 3,4,5,6-tetrapropylphthalate (5.22 g, 14.4 mmols) was added at 0° C. to a 50 ml THF solution of LiAlH$_4$ (1.20 g, 31.7 mmols). After stirring at room temperature for an hour, water was added for hydrolysis. The mixture was treated with 2N H$_2$SO$_4$ followed by extraction with diethyl ether. Subsequently, the extract was washed with brine and dried over anhydrous magnesium sulfate. Column chromatography was performed using silica gel as the packing material to give the title compound (3.67 g) as a white solid. The isolation yield was 91%.

$^1$H NMR(CDCl$_3$, Me$_4$Si) δ 1.05 (t, J=7.3 Hz, 6H), 1.05 (t, J=7.3 Hz, 6H), 1.46-1.58 (m, 8H), 2.55 (t, J=8.4 Hz, 4H), 2.65 (t, J=8.4 Hz, 4H), 3.27 (bs, 2H), 4.76 (s, 4H); $^{13}$C NMR (CDCl$_3$, Me$_4$Si) δ 14.82 (2C), 15.04 (2C), 24.75 (2C), 25.64 (2C), 31.90 (2C), 32.39 (2C), 59.82 (2C), 136.17 (2C), 138.10 (2C), 139.58 (2C).

Reference Example 27

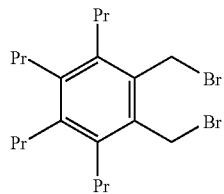

1,2-Bis(bromomethyl)-3,4,5,6-tetrapropylbenzene

Tribromophospnine (0.54 ml, 5.70 mmols) was dropwise added to 20 ml of a chloroform solution of 1,2-bis(hydroxymethyl)-3,4,5,6-tetrapropylbenzene (1.75 g, 5.70 mmols) at room temperature. After stirring for an hour, the mixture was treated with water followed by extracting with chloroform. Subsequently, the extract was washed with sodium hydrogencarbonate aqueous solution and brine, followed by drying over anhydrous magnesium sulfate. Column chromatography was performed using silica gel as the packing material to give the title compound (1.866 g) as a white solid. The GC yield was 100% and the isolation yield was 87%.

$^1$H NMR (CDCl$_3$, Me$_4$Si) δ 1.03-1.10 (m, 12H), 1.47-1.59 (m, 8H), 2.52 (t, J=8.3 Hz, 4H), 2.66 (t, J=8.2 Hz, 4H), 4.71 (s, 4H); $^{13}$C NMR (CDCl$_3$, Me$_4$Si) δ14.99 (2C), 15.07 (2C), 24.67 (2C), 25.00 (2C), 29.04 (2C), 31.85 (2C), 32.17 (2C), 132.70 (2C), 139.20 (2C), 141.00 (2C). Elemental Analysis: Calcd. for C$_{20}$H$_{32}$Br$_2$: C, 55.57; H, 7.46; Br, 36.97. Found: C, 55.46; H, 7.40; Br. 36.98.

Reference Example 28

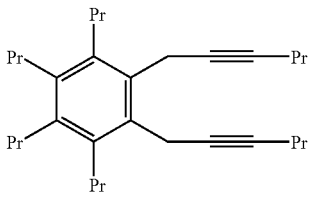

1,2-Bis(2-hexynyl)-3,4,5,6-tetrapropylbenzene n-Butyl lithium (9.7 ml, 15.56 mmols, 1.6 M) was added to a 30 ml THF solution of 1-pentyne (1.67 ml, 17.12 mmols) at −78° C., and the mixture was stirred at room temperature for an hour. 1,2-Bis(bromomethyl)-3,4,5,6-tetrapropylbenzene (1.68 g, 3.89 mmols) and DMPU (1.9 ml, 15.56 mmols) were added to the mixture at room temperature. After stirring for an hour, 3N HCl was added to terminate the reaction. The reaction mixture was extracted with hexane. The extract was then washed with sodium hydrogencarbonate aqueous solution and brine, followed by drying over anhydrous magnesium sulfate. Column chromatography was performed using silica gel as the packing material to give the title compound (1.520 g) as a white solid. The GC yield was 100% and the isolation yield was 97%

$^1$H NMR (CDCl$_3$, Me$_4$Si) δ 0.93 (t, J=7.4 Hz, 6H), 1.05 (t, J=7.2 Hz, 6H), 1.06 (t, J=7.2 Hz, 6H), 1.43-1.61 (m, 12H), 2.07 (tt, J=2.2, 7.1 Hz, 4H), 2.51 (t, J=8.4 Hz, 4H), 2.61 (t, J=8.5 Hz, 4H), 3.59 (t, J=2.2 Hz, 4H; $^{13}$C NMR (CDCl$_3$, Me$_4$Si) δ13.48 (2C), 15.03 (2C), 15.15 (2C), 19.40 (2C), 20.99 (2C), 22.36 (2C), 24.46 (2C), 24.80 (2C), 32.33 (2C), 32.41 (2C), 78.58 (2C), 80,34 (2C), 132.92 (2C), 137.21 (2C), 137.94 (2C). Elemental Analysis: Calcd. for C$_{30}$H$_{46}$: C, 88.60; H, 11.40.

Found: C,88.49; H, 11.47. High resolution mass spectrometer: Calcd. for C$_{3046}$ 406.3600, Found: 406.3626.

Reference Example 29

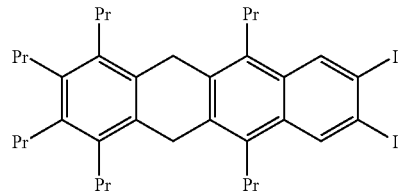

6,11-Dihydro-2,3-diiodo-5,7,8,9,10,12-hexapropyl-naphthacene n-Butyl lithium (3.0 ml, 4.8 mmols, 1.6mol/l) was added to a THF solution (20 ml) of Cp$_2$ZrCl$_2$ (0.702 g, 2.4 mmols) at −78° C. After the mixture was stirred for an hour, 1,2-bis(2-hexynyl)-3,4,5,6-tetrapropylbenzene (0.813 g, 2.0 mmols) was added to the mixture. A cooling bath was withdrawn, and the mixture was stirred for an hour. Tetraiodobenzene (1.16 g, 2.0 mmols), DMPU (0.73 ml, 6.0 mmols) and CuCl (0.416 g, 4.2 mmols) were added to the mixture. After stirring for an hour at 50° C., 3N HCl was added to terminate the reaction. The reaction mixture was extracted with chloroform. The extract was then washed with sodium hydrogencarbonate aqueous solution and brine. After the pressure was reduced, column chromatography was performed using silica gel as the packing material to give the title compound (0.477 g) as a pink solid. The isolation yield was 33%

$^1$H NMR (CDCl$_3$, Me$_4$Si) δ 1.06 (t, J=7.2 Hz, 6H), 1.15 (t, J=7.2 Hz, 12H), 1.49-1.72 (m, 12H), 2.56 (t, J=8.4 Hz, 4H), 2.74 (t, J=8.4 Hz, 4H), 3.07 (t, J=8.1 Hz, 4H), 3.98 (s, 4H), 8.52 (s, 2H); $^{13}$C NMR (CDCl$_3$, Me$_4$Si) δ 14.78 (2C), 15.07 (2C), 15.13 (2C), 24.25 (2C), 24.68 (2C), 25.04: (2C), 30.47. (2C), 30.59 (2C), 32.21 (2C), 32.34 (2C), 102.71 (2C), 131.01 (2C), 131.97 (2C), 133.47 (2C), 135.09 (2C), 135.50

Example 5

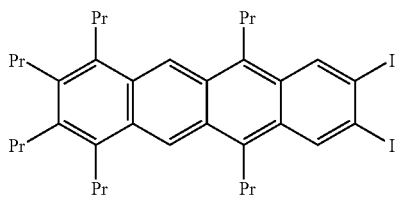

2,3-Diiodo-5,7,8,9,10,12-hexapropylnaphthacene 6,11-Dihydro-5,7,8,9,10,12-hexapropyl-2,3-diiodonaphthacene (0.23 8 g, 0.324 mmol), 2,3-dichloro-5,6-dicyanobenzoquinone (0.081 g, 0.35 mmol) and 1,4-dioxane (2 ml) were charged in a reactor. The mixture was refluxed for 3 hours. After cooling, the precipitates were removed by filtration. The solvent in the mixture was removed in vacuum followed by recrystallization from chloroform/methanol. The orange red title compound (0.081 g) was obtained. The isolation yield was 34%.

$^1$H NMR (CDCl$_3$, Me$_4$Si) δ 1.13 (t, J=7.4 Hz, 6H), 1.21 (t, J=7.2 Hz, 6H), 1.24 (t, J=7.2 Hz, 6H), 1.60-1.67 (m, 4H), 1.80-1.95 (m, 8H), 2.79 (t, J=8.3 Hz, 4H), 3.19 (t, J=8.1 Hz, 4H), 3.60 (t, J=8.0 Hz, 4H), 8.82 (s, 2H), 8.99 (s, 2H); $^{13}$C NMR (CDCl$_3$, Me$_4$Si) δ 14.87 (2C), 15.02 (2C), 15.09 (2C), 24.43 (2C), 24.82 (2C), 24.88 (2C), 30.49 (2C), 31.76 (2C), 32.85 (2C), 102.09 (2C), 120.37 (2C), 127.87 (2C), 128.74 (2C), 130.13 (2C), 133.01 (2C), 133.43 (2C), 136.37 (2C), 137.13 (2C). High resolution mass spectrometer: Calcd. for C$_{36}$H$_{46}$I$_2$: 732.1689, Found: 732.1709.

Reference Example 30

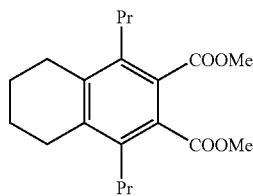

Dimethyl 1,4-dipropyl-5,6,7,8-tetrahydronaphthalene-2,3-dicarboxylate 4,10-Tetradodecadiyne (9.14 g, 48.03 mmols) was added at −78° C. to a 200 ml THF solution of bis(η$^5$-cyclopentadienyl)dibutylzirconium, which was prepared from bis(η$^5$-cyclopentadienyl)dichlorozirconium (16.849 g, 57.64 mmols) and n-butyl lithium (75.8 ml, 115.3 mmols, 1.52 M). After elevating to room temperature, the reaction mixture was stirred for an hour. DMAD (17.4 ml, 144.01 mmols) and CuCl (9.51 g, 96.06 mmols) were added to the reaction mixture at room temperature. After stirring for an hour, 3N HCl was added for hydrolysis and the mixture was extracted with hexane. The extract was then washed with sodium hydrogencarbonate aqueous solution and brine, followed by drying over anhydrous magnesium sulfate. Column chromatography was performed using silica gel as the packing material to give the title compound (8.133 g) as colorless crystals by recrystallization from methanol. The GC yield was 58% and the isolation yield was 51%.

$^1$H NMR (CDCl$_3$, Me$_4$Si) δ 0.96 (t, J=7.3 Hz, 6H), 1.50-1.56 (m, 4H), 1.76 (bs, 4H), 2.59 (t, J=8.2 Hz, 4H), 2.74 (bs, 4H), 3.82 (s, 6H); $^{13}$C NMR (CDCl$_3$, Me$_4$Si) δ 14.46 (2C), 22.41 (2C), 23.53 (2C). 26.80 (2C), 31.96 (2C), 51.93 (2C), 129.56 (2C), 136.75 (2C), 138.41 (2C), 169.50 (2C). Elemental Analysis: Calcd. for C$_{20}$H$_{28}$O$_4$: C, 72.26; H, 8.49. Found: C, 72.06; H, 8.60.

Reference Example 31

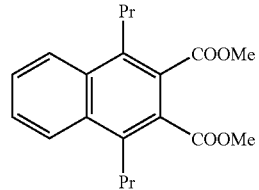

Dimethyl 1,4-dipropylnaphthalene-2,3-dicarboxylate 2,3-Dichloro-5,6-dicyanobenzoquinone (1.362 g, 6.0 mmols) was added to a solution of dimethyl 1,4-dipropyl-5,6,7,8-tetrahydronaphthalene-2,3-dicarboxylate (0.665 g, 2.0 mmols) in benzene (20 ml). The mixture was then refluxed for 24 hours. After filtration, the solvent in the mixture was removed in vacuum. Column chromatography was performed using silica gel as the packing material to give the title compound (0.464 g ) as colorless crystals. The GC yield was 87% and the isolation yield was 71%.

$^1$H NMR (CDCl$_3$, Me$_4$Si) δ 1.05 (t, J=7.4 Hz, 6H), 1.71-1.81 (m, 4H), 3.07 (t, J=8.1 Hz, 4H), 3.91 (s, 6H), 7.60 (dd, J=3.4, 6,5 Hz, 2H), 8.12 (dd, J=3.4, 6.5 Hz, 2H); $^{13}$C NMR (CDCl$_3$, Me$_4$Si) δ 14.52 (2C), 24.64 (2C), 32.20 (2C), 52.26 (2C), 125.53 (2C), 127.28 (2C), 128.25 (2C), 132.42 (2C), 136.85 (2C), 169.53 (2C). Elemental Analysis: Calcd. for C$_{20}$H$_{24}$O$_4$: C, 73.15; H,7.37. Found: C, 73.10; H, 7.44.

Reference Example 32

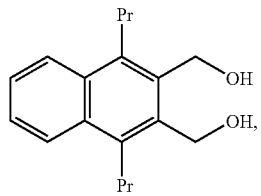

2,3-Bis(hydroxymethyl)-1,4-dipropylnaphthalene

Dimethyl 1,4-dipropylnaphthalene-2,3-dicarboxylate (0.295 g, 0.898 mmol) was added to a 5 ml THF solution of LiAlH$_4$ (0.075 g, 1.98 mmol) at 0° C. After stirring at room temperature for an hour, water was added to effect hydrolysis. The mixture was treated with 2N H$_2$SO$_4$ followed by extraction with diethyl ether. The extract was washed with brine and dried over anhydrous magnesium sulfate. The extract was concentrated under reduced pressure. The title compound (0.219 g) was obtained as a white solid. The isolation yield was 90%.

$^1$H NMR (CDCl$_3$, Me$_4$Si) δ(t, J=7.3 Hz, 6H), 1.59-1.67 (m, 4H), 3.08 (t, J=8.2 Hz, 4H), 3.51 (bs, 2H), 4.87 (s, 4H), 7.47 (dd, J=3.3, 6.5 Hz, 2H), 8.04 (dd, J=3.3, 6.5 Hz, 2H); $^{13}$C NMR (CDCl$_3$, Me$_4$Si) δ 14.52 (2C), 24.96 (2C), 31.52 (2C), 59.71 (2C), 125.05 (2C), 125.77 (2C), 132.12 (2C), 134.53 (2C), 136.48 (2C). Elemental Analysis: Calcd. for C$_{18}$H$_{24}$O$_2$: C, 79.37; H, 8.88. Found: C, 79.43; H, 9.01.

Reference Example 33

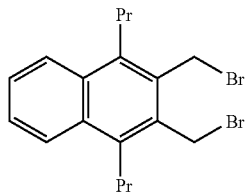

2,3-Bis(bromomethyl)-1,4-dipropylnaphthalene

Tribromophospnine (0.04 ml, 0.42 mmol) was dropwise added to a 5 ml chloroform solution of 2,3-bis(hydroxymethyl)-1,4-dipropylnaphthalene (0.109 g, 0.40 mmol) at room temperature. After stirring for an hour, the mixture was treated with water followed by extracting with chloroform. The extract was washed with sodium hydrogencarbonate aqueous solution and brine, followed by drying over anhydrous magnesium sulfate. Column chromatography was performed using silica gel as the packing material to give the title compound (0.115 g) as a white solid. The isolation yield was 72%.

$^1$H NMR (CDCl$_3$, Me$_4$Si) δ 1.14 (t, J=7.3 Hz, 6H), 1.75 (bs, 4H), 3.12 (t, J=8.3 Hz, 4H), 4.92 (s, 4H), 7.49 (dd, J=3.3,6.5 Hz, 2H), 8.02 (dd, J=3.3, 6.5 Hz, 2H); $^{13}$C NMR (CDCl$_3$, Me$_4$Si) δ 14.77 (2C), 24.37 (2C), 29.01 (2C), 31.11(2c), 125.17 (2C), 126.59 (2C), 130.91 (2C), 132.44 (2C), 138.44 (2C). Elemental Analysis:

Calcd. for C$_{18}$H$_{22}$Br$_2$: C, 54.30; H, 5.57; Br, 40.13, Found: C, 54.21; H, 5.57; Br, 40.24.

Reference Example 34

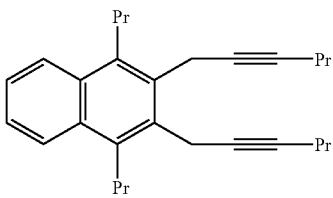

2,3-Bis(2-hexynyl)-1,4-dipropylnaphthalene n-Butyl lithium (7.6 ml, 19.1 mmols, 2.52 M) was added to a 30 ml THF solution of 1-pentyne (2.05 ml, 21.06 mmols) at −78° C., and the mixture was stirred at room temperature for an hour. 2,3-Bis(bromomethyl)-1,4-dipropylnaphthalene (1.91 g, 4.79 mmols) and DMPU (2.3 ml, 19.1 mmols) were added to the mixture at room temperature. After stirring for an hour, the mixture was treated with 3N HCl and extracted with hexane. The extract was then washed with sodium hydrogencarbonate aqueous solution and brine, followed by drying over anhydrous magnesium sulfate. Column chromatography was performed using silica gel as the packing material to give the title compound (1.66 g) as a white solid. The isolation yield was 93%

$^1$H NMR (CDCl$_3$, Me$_4$Si) 0.91 (t, J=7.4 Hz, 6H), 1.12 (t, J=7.3 Hz, 6H), 1.40-1.49 (m, 4H), 1,68-1.78 (m, 4H), 2.07 (tt, J=2.1, 7.0 Hz, 4H), 3.10 (t, J=8.3 Hz, 4H), 3.84 (t, J=2.1 Hz, 4H), 7.41 (dd, J=3,3, 6.5 Hz, 2H), 8.01 (dd, J=3.3, 6.5 Hz, 2H); $^{13}$C NMR (CDCl$_3$, Me$_4$Si) δ 13.43 (2C), 14.77 (2C), 19.96 (2C), 20.88 (2C), 22.32 (2C), 24.11 (2C), 31.40 (2C), 78.25 (2C), 80.95 (2C), 124.64 (2C), 125.02 (2C), 131.66 (2C), 132.48 (2C), 134.99 (2C). Elemental Analysis: Calcd. for C$_{28}$H$_{36}$: C, 90.26; H, 9.74. Found: C, 90.13; H, 9.86.

Reference Example 35

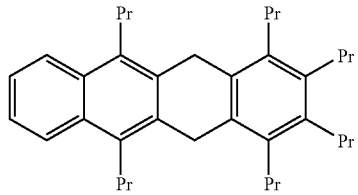

5,12-Dihydro-1,2,3,4,6,11-hexapropylnaphthacene 2,3-Bis(2-hexynyl)-1,4-dipropylnaphthalene (0.373 g, 1.0 mmol) was added at −78° C. to a 20 ml THF solution of bis(i$^5$-cyclopentadienyl)dibutylzirconium, which was prepared from bis(η$^5$-cyclopentadienyl)dichlorozirconium (0.351 g, 1.2 mmol) and n-butyl lithium (1.5 ml, 2.4 mmols, 1.6 M). After elevating to room temperature, the reaction mixture was stirred for an hour. 4-Octyne (0.22 ml, 1.5 mmol) and NiBr$_2$(PPh$_3$)$_2$ (0.892 g, 1.2 mmol) were added to the reaction mixture at room temperature. After stirring for 24 hours, hydrolysis was effected by 3N HCl followed by extraction with hexane. The extract was washed with sodium hydrogencarbonate aqueous solution and brine followed by drying over anhydrous magnesium sulfate. Column chromatography was performed using silica gel as the packing material to give the title compound (0.224 g) as somewhat orange powders by floured with ethanol. The isolation yield was 46%.

$^1$H NMR (CDCl$_3$, Me$_4$Si) δ 1.14-1.19 (m, 188H), 1.48-1.79 (m, 12H), 2.57 (t, J=8.4 Hz, 4H), 2.76 (t, J=8.4 Hz, 4H), 3.20 (t, J=8.3 Hz, 4H), 4.04 (s, 4H), 7.42 (dd, J=3.3, 6.6 Hz, 2H), 8.05 (dd, J=3.3, 6.6 Hz, 2H); $^{13}$C NMR (CDCl$_3$, Me$_4$Si) δ14.88 (2C), 15.06 (2C), 15.10 (2C), 24.29 (2C), 24.69 (2C), 25.08 (2C), 30.42 (2C), 30.98 (2C), 32.26 (2C), 32.35 (2C). 124.47 (2C), 131.03 (2C), 131.92 (2C), 134.11 (2C), 134.26 (2C), 135.03 (2C), 136.57 (2C). High resolution mass spectrometer: Calcd. for C$_{36}$H$_{50}$ 482.3913, Found: 482.3902.

Example 6

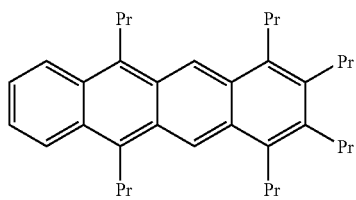

1,2,3,4,6,11-Hexapropylnaphthacene 5,12-Dihydro-1,2,3,4,6,11-hexapropylnaphthacene (0.503 g, 1.04 mmol), 2,3-dichloro-5,6-dicyanobenzoquinone (0.260 g, 1.14 mmol) and 1,4-dioxane (3 ml) were charged in a reactor. The mixture was refluxed for 24 hours. After cooling, the precipitates were removed by filtration. The solvent in the mixture was removed in vacuum followed by recrystallization from chloroform/methanol. The orange red title compound (0.112 g) was obtained. The NMR yield was 36% and the isolation yield was 22%.

$^1$H NMR (CDCl$_3$, Me$_4$Si) δ 1.12 (t, J=7.3 Hz, 6H), 1.25 (t, J=7.4 Hz, 6H), 1.27 (t, J=7.3 Hz, 6H), 1.63-1.69 (m, 4H), 1.85-2.01 (m, 8H), 2.80 (t, J=8.4 Hz, 4H), 3.23 (t, J=8.3 Hz, 4H), 3.75 (t, J=8.1 Hz, 4H), 7.40 (dd, J=7.1, 3.2 Hz, 2H), 8.30 (dd, J=7.1, 3.2Hz, 2H), 9.06 (s, 2H); $^{13}$C NMR (CDCl$_3$, Me$_4$Si) 14.99 (2C), 15.06 (2C), 15.14 (2C), 24.40 (2C), 24.76 (2C), 24.91 (2C), 30.74 (2C), 31.81 (2C), 32.62 (2C), 32.83 (2C), 120.03 (2C), 124.09 (2C), 125.35 (2C), 127.62 (2C), 128.55 (2C), 129.42 (2C), 133.30 (2C), 133.36 (2C), 136.33 (2C). High resolution mass spectrometer: Calcd. for C$_{36}$H$_{18}$: 480.3756, Found: 480.3747.

According to the present invention, the solubility of polyacenes can be improved by introducing substituents into the polyacenes on the side chains. Since various substituents can be introduced, the side chains of polyacenes can be modified in various ways and their physical properties can be altered depending upon use.

Heretofore, there was a tendency that the solubility gradually decreases as the number of aromatic rings in condensed polycyclic aromatic compounds increases. In the present invention, however, the solubility can be maintained by introducing a variety of substituents, even if the number of aromatic rings in condensed polycyclic aromatic compounds increases. Therefore, latitude in synthesis of various condensed polycyclic aromatic compounds can be markedly improved.

The invention claimed is:

1. A polyacene derivative represented by general formula (I) below:

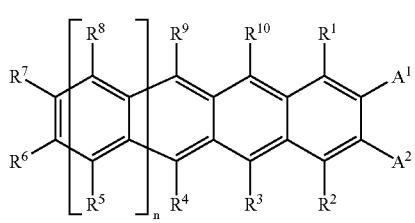

wherein each of R$^3$, R$^5$, R$^6$, R$^7$, R$^8$ and R$^{10}$, which may be the same or different, independently represents hydrogen atom; a C$_1$-C$_{40}$ hydrocarbon group which may optionally be substituted; a C$_1$-C$_{40}$ alkoxy group which may optionally be substituted; a C$_6$-C$_{40}$ aryloxy group which may optionally be substituted; an amino group which may optionally be substituted; a hydroxy group; or a silyl group which may optionally be substituted; provided that R$^6$ and R$^7$ may be cross-bridged with each other to form a C$_4$-C$_{40}$ saturated or unsaturated ring, and the saturated or unsaturated ring may be intervened by oxygen atom, sulfur atom or a group shown by formula: —N(R$^{11}$)— wherein R$^{11}$ is hydrogen atom or a hydrocarbon group, or may optionally be substituted;

each of R$^1$ and R$^2$, which may be the same or different, independently represents a C$_1$-C$_{40}$ alkyl group which may optionally be substituted, or a C$_6$-C$_{18}$ aryl group which may optionally be substituted;

each of R$^4$ and R$^9$, which may be the same or different, independently represents a C$_1$-C$_{40}$ alkyl group, or a C$_6$-C$_{18}$ aryl group which may optionally be substituted;

each of A$^1$ and A$^2$, which may be the same or different, independently represents a C$_2$-C$_{40}$ alkoxycarbonyl group which may optionally be substituted;

n is 1;

with proviso that the case of (b) below is excluded:
(b) R$^3$, R$^4$, R$^9$ and R$^{10}$ are all aryl groups that may optionally be substituted.

2. A polyacene derivative represented by general formula (I) below:

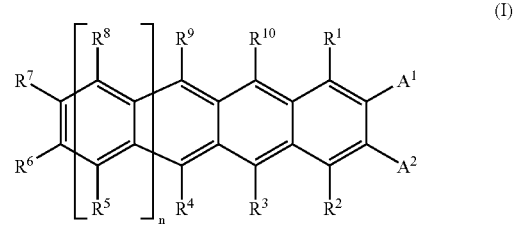

wherein each of R$^3$, R$^5$, R$^6$, R$^7$, R$^8$ and R$^{10}$, which may be the same or different, independently represents hydrogen atom; a C$_1$-C$_{40}$ hydrocarbon group which may optionally be substituted; a C$_1$-C$_{40}$ alkoxy group which may optionally be substituted; a C$_6$-C$_{40}$ aryloxy group which may optionally be substituted; an amino group which may optionally be substituted; a hydroxy group; or a silyl group which may optionally be substituted; provided that R$^6$ and R$^7$ may be cross-bridged with each other to form a C$_4$-C$_{40}$ saturated or unsaturated ring, and the saturated or unsaturated ring may be intervened by oxygen atom, sulfur atom or a group shown by formula: —N(R$^1$)— wherein R$^{11}$ is hydrogen atom or a hydrocarbon group, or may optionally be substituted;

each of A$^1$, A$^2$, R$^1$ and R$^2$, which may be the same or different, independently represents a C$_1$-C$_{40}$ alkyl group which may optionally be substituted, or a C$_6$-C$_{18}$ aryl group which may optionally be substituted;

each of R$^4$ and R$^9$, which may be the same or different, independently represents a C$_1$-C$_{40}$ alkyl group, or a C$_6$-C$_{18}$ aryl group which may optionally be substituted;

n is 1;

with proviso that the cases of (a) and (b) below are excluded:
(a) R$^1$, R$^2$, R$^3$, R$^4$, R$^5$, R$^6$, R$^7$, R$^8$, R$^9$, R$^{10}$, A$^1$ and A$^2$ are all methyl groups; and (b) $R^3$, $R^4$, $R^9$ and $R^{10}$ are all aryl groups that may optionally be substituted.

3. A polyacene derivative represented by general formula (I) below:

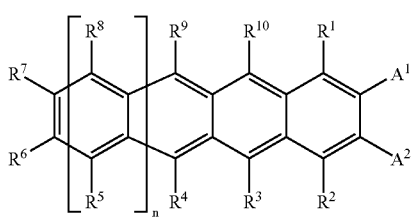

(I)

wherein each of $R^1$ and $R^2$, which may be the same or different, independently represents a hydrogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; an amino group which may optionally be substituted; a hydroxy group; or a silyl group which may optionally be substituted;

each of $R^4$ and $R^9$, which may be the same or different, independently represents a hydrogen atom; a $C_1$-$C_{40}$ alkyl group, a $C_2$-$C_{40}$ alkenyl group which may optionally be substituted, a $C_2$-$C_{40}$ alkynyl group which may optionally be substituted, a $C_3$-$C_{40}$ allyl group group which may optionally be substituted, a $C_4$-$C_{40}$ alkyldienyl group which may optionally be substituted, a $C_4$-$C_{40}$ polyenyl group which may optionally be substituted, a $C_6$-$C_{18}$ aryl group which may optionally be substituted, a $C_6$-$C_{40}$ alkylaryl group which may optionally be substituted, a $C_6$-$C_{40}$ arylalkyl group which may optionally be substituted, a $C_4$-$C_{40}$ cycloalkyl group, a $C_4$-$C_{40}$ cycloalkenyl group which may optionally be substituted; a $C_1$-$C_{40}$ alkoxy group which may optionally be substituted; a $C_6$-$C_{40}$ aryloxy group which may optionally be substituted; an amino group which may optionally be substituted; a hydroxy group; or a silyl group which may optionally be substituted;

each of $R^3$, $R^5$, $R^6$, $R^7$, $R^8$ and $R^{10}$, which may be the same or different, independently represents a $C_1$-$C_{40}$ alkyl group which may optionally be substituted, or a $C_6$-$C_{18}$ aryl group which may optionally be substituted;

each of $A^1$ and $A^2$, which may be the same or different, independently represents a halogen atom;

n is 1 with a proviso that $R^3$, $R^4$, $R^9$ and $R^{10}$ may not all be aryl groups.

4. A polyacene derivative represented by formula (Ia) below:

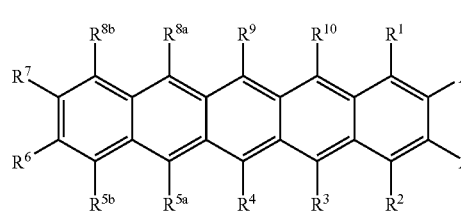

(Ia)

wherein:

$A^1$ and $A^2$ are a $C_2$-$C_{40}$ alkoxycarbonyl group which may optionally be substituted, $R^1$, $R^2$, $R^{5b}$, $R^6$, $R^7$, and $R^{8b}$ are a $C_1$-$C_{40}$ alkyl group which may optionally be substituted;

$R^4$ and $R^9$ are a $C_1$-$C_{40}$ alkyl group;

each of $R^3$, $R^{5a}$, $R^{8a}$ and $R^{10}$, which may be the same or different, independently represents hydrogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; an amino group which may optionally be substituted; a hydroxy group; or a silyl group which may optionally be substituted; provided that $R^6$ and $R^7$ may be cross-bridged with each other to form a $C_4$-$C_{40}$ saturated or unsaturated ring, and the saturated or unsaturated ring may be intervened by oxygen atom, sulfur atom or a group shown by formula: —N($R^{11}$)— wherein $R^{11}$ is hydrogen atom or a hydrocarbon group, or may optionally be substituted; and provided that the cases of (a') and (b') below are excluded:
  (a') at least one of $R^3$, $R^{5a}$, $R^{8a}$, and $R^{10}$ is a diarylamine group; and
  (b') $R^3$ and $R^{10}$ are both aryl groups which may optionally be substituted, or $R^{5a}$ and $R^{8a}$ are both aryl groups which may optionally be substituted.

5. A polyacene derivative represented by the formula (Ia),

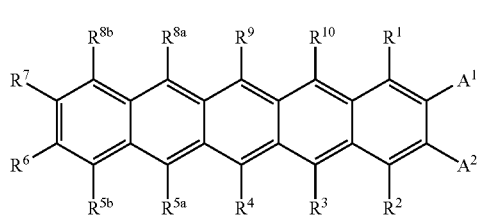

(Ia)

wherein:

$A^1$ and $A^2$ are a halogen atom;

$R^3$, $R^{5a}$, $R^{8a}$ and $R^{10}$ are a $C_1$-$C_{40}$ alkyl group which may optionally be substituted;

each of $R^1$, $R^2$, $R^{5b}$, $R^6$, $R^7$ and $R^{8b}$, which may be the same or different, independently represents a hydrogen atom; a $C_1$-$C_{40}$ alkyl group which may optionally be substituted; a $C_2$-$C_{40}$ alkenyl group which may optionally be substituted; a $C_2$-$C_{40}$ alkynyl group which may optionally be substituted; provided that $R^6$ and $R^7$ may be cross-bridged with each other to form a $C_4$-$C_{40}$ saturated or unsaturated ring; and each of $R^4$ and $R^9$, which may be the same or different, independently represents a hydrogen atom; a $C_1$-$C_{40}$ alkyl group, a $C_2$-$C_{40}$ alkenyl group which may optionally be substituted, a $C_2$-$C_{40}$ alkynyl group which may optionally be substituted.

6. A process of producing the polyacene derivative represented by formula (I) below:

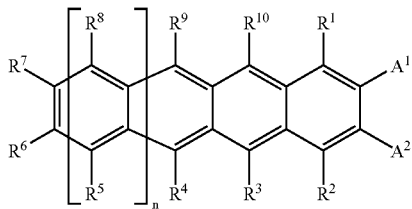

wherein each of $R^1$, $R^2$, $R^3$, $R^4$, $R^5$, $R^6$, $R^7$, $R^8$, $R^9$ and $R^{10}$, which may be the same or different, independently represents hydrogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; an amino group which may optionally be substituted; a hydroxy group; or a silyl group which may optionally be substituted; provided that $R^6$ and $R^7$ may be cross-bridged with each other to form a $C_4$-$C_{40}$ saturated or unsaturated ring, and the saturated or unsaturated ring may be intervened by oxygen atom, sulfur atom or a group shown by formula: —$N(R^{11})$— wherein $R^{11}$ is hydrogen atom or a hydrocarbon group, or may optionally be substituted;

each of $A^1$ and $A^2$, which may be the same or different, independently represents hydrogen atom; a halogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; a $C_7$-$C_{40}$ alkylaryloxy group which may optionally be substituted; a $C_2$-$C_{40}$ alkoxycarbonyl group which may optionally be substituted; a $C_7$-$C_{40}$ aryloxycarbonyl group which may optionally be substituted; cyano group —CN; carbamoyl group —C(=O)NH$_2$; a haloformyl group —C(=O)—X, wherein X represents a halogen atom; formyl group —C(=O)—H; isocyano group; isocyanate group; thiocyanate group or thioisocyanate group; provided that $A^1$ and $A^2$ may be cross-bridged with each other to form a ring shown by formula: —C(=O)—B—C(=O)— wherein B is oxygen atom or a group shown by formula —$N(B^1)$— wherein $B^1$ is hydrogen atom, a $C_1$-$C_{40}$ hydrocarbon group or a halogen atom; and, n is 1 or 2, which comprises aromatizing hydrocarbon condensed rings represented by formula (II) below:

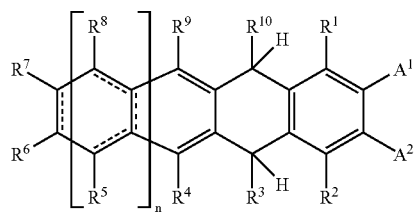

wherein $R^1$, $R^2$, $R^3$, $R^4$, $R^5$, $R^6$, $R^7$, $R^8$, $R^9$, $R^{10}$, $A^1$, $A^2$ and n have the same significance as defined above;

the bond shown by formula below represents a single bond or a double bond;

==== provided that when the bond is a single bond, hydrogen atom is further bound directly to the carbon atoms which are directly bound to $R^5$, $R^6$, $R^7$ and $R^8$;

in the presence of a dehydrogenation reagent comprising a combination of an alkyl lithium and an alkyl halide.

7. The process of producing the polyacene derivative according to claim 6, wherein the alkyl lithium is first added to the hydrocarbon condensed rings followed by adding the alkyl halide.

8. The process of producing the polyacene derivative according to claim 6, wherein at least 5 of $R^1$, $R^2$, $R^3$, $R^4$, $R^5$, $R^6$, $R^7$, $R^8$, $R^9$, $R^{10}$, $A^1$ and $A^2$ are groups other than hydrogen atom.

9. The process of producing the polyacene derivative according to claim 6, wherein at least 6 of $R^1$, $R^2$, $R^3$, $R^4$, $R^5$, $R^6$, $R^7$, $R^8$, $R^9$, $R^{10}$, $A^1$ and $A^2$ are groups other than hydrogen atom.

10. The process of producing the polyacene derivative according to claim 6, wherein the polyacene derivative is a pentacene derivative represented by formula (Ia):

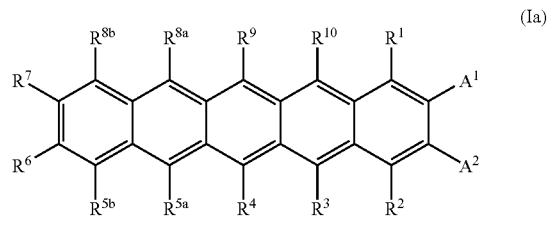

wherein each of $R^1$, $R^2$, $R^3$, $R^4$, $R^{5a}$, $R^{5b}$, $R^6$, $R^7$, $R^{8a}$, $R^{8b}$, $R^9$ and $R^{10}$, which may be the same or different, independently represents hydrogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; an amino group which may optionally be substituted; a hydroxy group; or a silyl group which may optionally be substituted; provided that $R^6$ and $R^7$ may be cross-bridged with each other to form a $C_4$-$C_{40}$ saturated or unsaturated ring, and the saturated or unsaturated ring may be intervened by oxygen atom, sulfur atom or a group shown by formula: —$N(R^{11})$— wherein $R^{11}$ is hydrogen atom or a hydrocarbon group, or may optionally be substituted;

each of $A^1$ and $A^2$, which may be the same or different, independently represents hydrogen atom; a halogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; a $C_7$-$C_{40}$ alkylaryloxy group which may optionally be substituted; a $C_2$-$C_{40}$ alkoxycarbonyl group which may optionally be substituted; a $C_7$-$C_{40}$ aryloxycarbonyl group which may optionally be substituted; cyano group —CN; carbamoyl group —C(=O)NH$_2$; a haloformyl group —C(=O)—X, wherein X represents a halogen atom; formyl group —C(=O)—H; isocyano group; isocyanate group; thiocyanate group or thioisocyanate group; provided that $A^1$ and $A^2$ may be cross-bridged with each other to form a ring shown by formula: —C(=O)—B—C(=O)— wherein B is oxygen atom or a group shown by formula —N($B^1$)— wherein $B^1$ is hydrogen atom, a $C_1$-$C_{40}$ hydrocarbon group or a halogen atom, and
at least 5 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom.

11. The process of producing the polyacene derivative according to claim 10, wherein at least 6 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom.

12. The process of producing the polyacene derivative according to claim 10, wherein at least 7 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom.

13. The process of producing the polyacene derivative according to claim 10, wherein at least 8 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom.

14. The process of producing the polyacene derivative according to claim 10, wherein at least 9 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom.

15. The process of producing the polyacene derivative according to claim 10, wherein at least 10 of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are groups other than hydrogen atom.

16. The process of producing the polyacene derivative according to claim 6, wherein any one of the combinations of $R^1$ and $R^2$, $R^3$ and $R^{10}$, $R^4$ and $R^9$, $R^5$ and $R^8$, $R^6$ and $R^7$, and $A^1$ and $A^2$ are the same substituents.

17. The process of producing the polyacene derivative according to claim 10, wherein any one of the combinations of $R^1$ and $R^2$, $R^3$ and $R^{10}$, $R^4$ and $R^9$, $R^{5a}$ and $R^{8a}$, $R^{5b}$ and $R^{8b}$, $R^6$ and $R^7$, and $A^1$ and $A^2$ are the same substituents.

18. The process of producing the polyacene derivative according to claim 6, wherein any one of $R^1$, $R^2$, $R^3$, $R^4$, $R^5$, $R^6$, $R^7$, $R^8$, $R^9$ and $R^{10}$ is a $C_1$-$C_{40}$ hydrocarbon group which may optionally be substituted, a $C_1$-$C_{40}$ alkoxy group which may optionally be substituted, or a $C_6$-$C_{40}$ aryloxy group which may optionally be substituted.

19. The process of producing the polyacene derivative according to claim 6, wherein any one of $R^1$, $R^2$, $R^3$, $R^4$, $R^{5a}$, $R^{5b}$, $R^6$, $R^7$, $R^{8a}$, $R^{8b}$, $R^9$ and $R^{10}$ is a $C_1$-$C_{40}$ hydrocarbon group which may optionally be substituted, a $C_1$-$C_{40}$ alkoxy group which may optionally be substituted, or a $C_6$-$C_{40}$ aryloxy group which may optionally be substituted.

20. The process of producing the polyacene derivative according to claim 6, wherein the case in which $R^1$, $R^2$, $R^3$, $R^4$, $R^5$, $R^6$, $R^7$, $R^8$, $R^9$, $R^{10}$, $A^1$ and $A^2$ are all hydrogen atoms in the formula (I) above, is excluded.

21. The process of producing the polyacene derivative according to claim 6, wherein, in the formula (I) above, when n is 1,
at least $R^1$, $R^2$, $R^4$ and $R^9$ are groups other than hydrogen atom,
or at least $R^3$, $R^5$, $R^8$ and $R^{10}$ are groups other than hydrogen atom, and
any one of $R^1$, $R^2$, $R^3$, $R^4$, $R^5$, $R^6$, $R^7$, $R^8$, $R^9$, $R^{10}$, $A^1$ and $A^2$ contains an aryl group, wherein the aryl group has a substituent(s), and
the cases of (a), (b), (c) and (d) below are excluded:
 (a) when $R^1$, $R^2$, $R^3$, $R^4$, $R^5$, $R^6$, $R^7$, $R^8$, $R^9$, $R^{10}$, $A^1$ and $A^2$ are all methyl groups;
 (b) when $R^3$, $R^4$, $R^9$ and $R^{10}$ are all aryl groups that may optionally be substituted;
 (c) when $R^1$, $R^2$, $R^4$ and $R^9$ are all alkoxy or aryloxy groups, and $R^3$, $R^5$, $R^6$, $R^7$, $R^8$, $R^{10}$, $A^1$ and $A^2$ are all hydrogen atoms; and
 (d) when $R^3$, $R^5$, $R^8$ and $R^{10}$ are all alkoxy or aryloxy groups, and $R^1$, $R^2$, $R^4$, $R^6$, $R^7$, $R^9$, $A^1$ and $A^2$ are all hydrogen atoms.

22. The process of producing the polyacene derivative according to claim 10, wherein the polyacene derivatives of the cases (a'), (b'), (c') and (d') below are excluded:

(a') a pentacene derivative represented by formula (Ia) below:

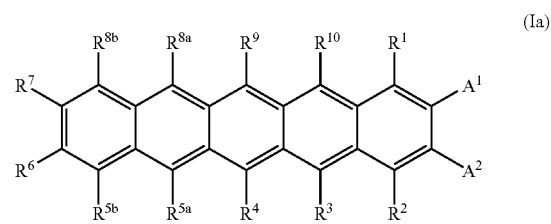

wherein $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ are all methyl groups; or $R^1$, $R^2$, $R^3$, $R^4$, $R^{5a}$, $R^{5b}$, $R^{8a}$, $R^{8b}$, $R^9$ and $R^{10}$ are all are all hydrogen atoms and at least one of $R^6$, $R^7$, $A^1$ and $A^2$ is an aryl group; or at least one of $R^1$, $R^2$, $R^3$, $R^4$, $R^{5a}$, $R^{5b}$, $R^6$, $R^7$, $R^{8a}$, $R^{8b}$, $R^9$, $R^{10}$, $A^1$ and $A^2$ is a diarylamine group;

(b') a pentacene derivative represented by formula (Ib) below:

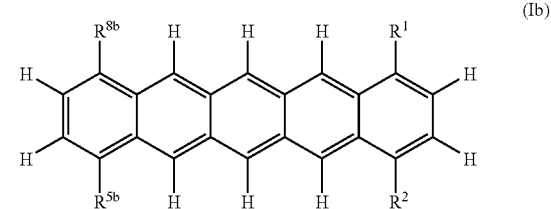

wherein $R^1$, $R^2$, $R^{5b}$ and $R^{8b}$ are all alkoxy or aryloxy groups;

(c') a pentacene derivative represented by formula (Ic) below:

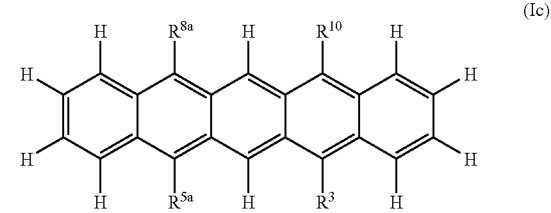

wherein at least 2 of $R^3$, $R^{5a}$, $R^{8a}$ and $R^{10}$ are aryl or arylalkynyl groups which may optionally be substituted; or at least one of $R^3$, $R^{5a}$, $R^{8a}$ and $R^{10}$ is an arylalkenyl group; or $R^3$, $R^{5a}$, $R^{8a}$ and $R^{10}$ are all alkoxy or aryloxy groups; and (d') a pentacene derivative represented by formula (Id) below:

$$\text{(Id)}$$

wherein $R^4$ and $R^9$ are hydrogen atom, a hydrocarbon group, an alkoxy group, an aryloxy group, a halogen atom or hydroxy group.

23. The process of producing the polyacene derivative according to claim 6, wherein when n is 1, $A^1$ and $A^2$ are a $C_2$-$C_{40}$ alkoxycarbonyl group which may optionally be substituted, and $R^1$, $R^2$, $R^4$ and $R^9$ are a $C_1$-$C_{40}$ alkyl group which may optionally be substituted or a $C_6$-$C_{18}$ aryl group which may optionally be substituted.

24. The process of producing the polyacene derivative according to claim 6, wherein when n is 1, $A^1$, $A^2$, $R^1$, $R^2$, $R^4$ and $R^9$ are a $C_1$-$C_{40}$ alkyl group which may optionally be substituted or a $C_6$-$C_{18}$ aryl group which may optionally be substituted.

25. The process of producing the polyacene derivative according to claim 6, wherein when n is 1, $A^1$ and $A^2$ are a halogen atom and $R^3$, $R^5$, $R^6$, $R^7$, $R^8$ and $R^{10}$ are a $C_1$-$C_{40}$ alkyl group which may optionally be substituted or a $C_6$-$C_{18}$ aryl group which may optionally be substituted.

26. The process of producing the polyacene derivative according to claim 10, wherein when the polyacene derivative is the pentacene derivative represented by the formula (Ia) above, $A^1$ and $A^2$ are a $C_2$-$C_{40}$ alkoxycarbonyl group which may optionally be substituted, and $R^1$, $R^2$, $R^4$, $R^{5b}$, $R^6$, $R^7$, $R^{8b}$ and $R^9$ are a $C_1$-$C_{40}$ alkyl group which may optionally be substituted or a $C_6$-$C_{18}$ aryl group which may optionally be substituted.

27. The process of producing the polyacene derivative according to claim 10, wherein when the polyacene derivative is the pentacene derivative represented by the formula (Ia) above, $A^1$, $A^2$, $R^1$, $R^2$, $R^4$, $R^{5b}$, $R^6$, $R^7$, $R^{8b}$ and $R^9$ are a $C_1$-$C_{40}$ alkyl group which may optionally be substituted or a $C_6$-$C_{18}$ aryl group which may optionally be substituted.

28. The process of producing the polyacene derivative according to claim 10, wherein when the polyacene derivative is the pentacene derivative represented by the formula (Ia) above, $A^1$ and $A^2$ are a halogen atom and $R^3$, $R^{5a}$, $R^{8a}$ and $R^{10}$ are a $C_1$-$C_{40}$ alkyl group which may optionally be substituted or a $C_6$-$C_{18}$ aryl group which may optionally be substituted.

29. A polyacene derivative represented by general formula (I) below:

$$\text{(I)}$$

wherein:

each of $R^3$, $R^5$, $R^6$, $R^7$, $R^8$ and $R^{10}$, which may be the same or different, independently represents hydrogen atom; a $C_1$-$C_{40}$ hydrocarbon group; a $C_1$-$C_{40}$ alkoxy group; a $C_6$-$C_{40}$ aryloxy group; an amino group; a hydroxy group; or a silyl group;

each of $R^1$, $R^2$, $R^4$ and $R^9$, which may be the same or different, independently represents a $C_1$-$C_{40}$ alkyl group, or a $C_6$-$C_{18}$ aryl group; each of $A^1$ and $A^2$, which may be the same or different, independently represents a $C_2$-$C_{40}$ alkoxycarbonyl group; and n is 1;

with proviso that the case of (b) below is excluded:

(b) $R^3$, $R^4$, $R^9$ and $R^{10}$ are all aryl groups that may optionally be substituted.

30. A resin composition comprising the polyacene derivative according to claim 29, and at least one synthetic organic polymer.

31. A polyacene derivative represented by general formula (I) below:

$$\text{(I)}$$

wherein:

each of $R^3$, $R^5$, $R^6$, $R^7$, $R^8$ and $R^{10}$, which may be the same or different, independently represents hydrogen atom; a $C_1$-$C_{40}$ hydrocarbon group; a $C_1$-$C_{40}$ alkoxy group; a $C_6$-$C_{40}$ aryloxy group; an amino group; a hydroxy group; or a silyl group;

each of $A^1$, $A^2$, $R^1$, $R^2$, $R^4$ and $R^9$, which may be the same or different, independently represents a $C_1$-$C_{40}$ alkyl group, or a $C_6$-$C_{18}$ aryl group; and n is 1;

with proviso that the cases of (a) and (b) below are excluded:

(a) $R^1$, $R^2$, $R^3$, $R^4$, $R^5$, $R^6$, $R^7$, $R^8$, $R^9$, $R^{10}$, $A^1$ and $A^2$ are all methyl groups; and (b) $R^3$, $R^4$, $R^9$ and $R^{10}$ are all aryl groups that may optionally be substituted.

32. A resin composition comprising the polyacene derivative according to claim 31, and at least one synthetic organic polymer.

33. A polyacene derivative represented by general formula (I) below:

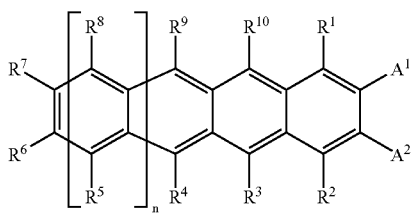

(I)

wherein:
  each of $R^1$, $R^2$, $R^4$ and $R^9$, which may be the same or different, independently represents hydrogen atom; a $C_1$-$C_{40}$ hydrocarbon group; a $C_1$-$C_{40}$ alkoxy group; a $C_6$-$C_{40}$ aryloxy group; an amino group; a hydroxy group; or a silyl group;
  each of $R^3$, $R^5$, $R^6$, $R^7$, $R^8$ and $R^{10}$, which may be the same or different, independently represents a $C_1$-$C_{40}$ alkyl group, or a $C_6$-$C_{18}$ aryl group;
  each of $A^1$ and $A^2$, which may be the same or different, independently represents a halogen atom;
  n is 1;
  with a proviso that $R^3$, $R^4$, $R^9$ and $R^{10}$ are not all aryl groups.

34. A resin composition comprising the polyacene derivative according to claim 33, and at least one synthetic organic polymer.

35. A polyacene derivative represented by formula (Ia) below:

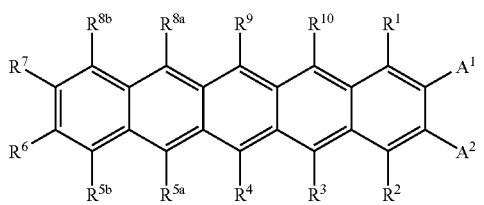

(Ia)

$A^1$ and $A^2$ are a $C_2$-$C_{40}$ alkoxycarbonyl group;
$R^1$, $R^2$, $R^4$, $R^{5b}$, $R^6$, $R^7$, $R^{8b}$ and $R^9$ are a $C_1$-$C_{40}$ alkyl group;
each of $R^3$, $R^{5a}$, $R^{8a}$ and $R^{10}$, which may be the same or different, independently represents hydrogen atom; a $C_1$-$C_{40}$ hydrocarbon group which may optionally be substituted; a $C_1$-$C_{40}$ alkoxy group which may optionally be substituted; a $C_6$-$C_{40}$ aryloxy group which may optionally be substituted; an amino group which may optionally be substituted; a hydroxy group; or a silyl group which may optionally be substituted; provided that $R^6$ and $R^7$ may be cross-bridged with each other to form a $C_4$-$C_{40}$ saturated or unsaturated ring, and the saturated or unsaturated ring may be intervened by oxygen atom, sulfur atom or a group shown by formula: —N($R^{11}$)— wherein $R^{11}$ is hydrogen atom or a hydrocarbon group, or may optionally be substituted; and
provided that the cases of (a') and (b') below are excluded:
  (a') at least one of $R^3$, $R^{5a}$, $R^{8b}$ and $R^{10}$ is a diarylamine group; and
  (b') $R^3$ and $R^{10}$ are both aryl groups which may optionally be substituted, or $R^{5a}$ and $R^{8a}$ are both aryl groups which may optionally be substituted.

36. A resin composition comprising the polyacene derivative according to claim 35, and at least one synthetic organic polymer.

37. A polyacene derivative represented by the formula (Ia),

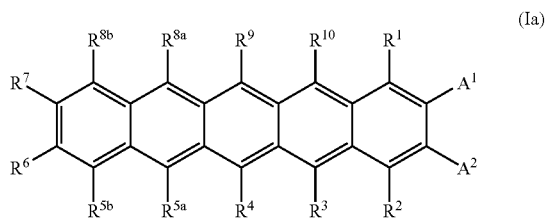

(Ia)

wherein:
  $A^1$ and $A^2$ are a halogen atom;
  $R^3$, $R^{5a}$, $R^{8a}$ and $R^{10}$ are a $C_1$-$C_{40}$ alkyl group;
  each of $R^1$, $R^2$, $R^{5b}$, $R^6$, $R^7$, and $R^{8b}$, which may be the same or different, independently represents a hydrogen atom; a $C_1$-$C_{40}$ alkyl group which may optionally be substituted; a $C_2$-$C_{40}$ alkenyl group which may optionally be substituted; a $C_2$-$C_{40}$ alkynyl group which may optionally be substituted; provided that $R^6$ and $R^7$ may be cross-bridged with each other to form a $C_4$-$C_{40}$ saturated or unsaturated ring; and
  each of $R^4$ and $R^9$, which may be the same or different, independently represents a hydrogen atom; a $C_1$-$C_{40}$ alkyl group, a $C_2$-$C_{40}$ alkenyl group which may optionally be substituted, a $C_2$-$C_{40}$ alkynyl group which may optionally be substituted.

38. A resin composition comprising the polyacene derivative according to claim 37, and at least one synthetic organic polymer.

39. A polyacene derivative selected from the group consisting of dimethyl 1,4,6,8,9,10,11,13-octapropylpentacene-2,3-dicarboxylate, dimethyl 1,4,6,11-tetrapropylnaphtacene-2,3-dicarbooxylate, dimethyl 1,4,6,8,9,10,11,13-octaethylpentacene-2,3-dicarbooxylate, 5,14-bis(p-bromophenyl)-7,12-dipropyl- 1,2,3,4-tetrahydropentacene, 2,3-diiodo-5,7,8,9,10,12-hexapropylnaphtacene, and 1,2,3,4,6,11-hexapropylnaphtacene.

40. A resin composition comprising the polyacene derivative according to claim 39, and at least one synthetic organic polymer.

* * * * *